United States Patent
Goodrich, Jr. et al.

(10) Patent No.: US 7,094,378 B1
(45) Date of Patent: *Aug. 22, 2006

(54) METHOD AND APPARATUS FOR INACTIVATION OF BIOLOGICAL CONTAMINANTS USING PHOTOSENSITIZERS

(75) Inventors: Raymond Paul Goodrich, Jr., Denver, CO (US); Dennis Hlavinka, Arvada, CO (US)

(73) Assignee: Gambro, Inc., Lakewood, CO (US)

( * ) Notice: Subject to any disclaimer, the term of this patent is extended or adjusted under 35 U.S.C. 154(b) by 1091 days.

This patent is subject to a terminal disclaimer.

(21) Appl. No.: 09/596,429

(22) Filed: Jun. 15, 2000

(51) Int. Cl.
*A61L 2/00* (2006.01)
*A01N 1/02* (2006.01)
*C12N 13/00* (2006.01)
*A61K 35/14* (2006.01)
*C07D 493/00* (2006.01)

(52) U.S. Cl. ......... 422/22; 422/186.3; 422/24; 422/28; 422/292; 435/2; 435/173.1; 435/238; 435/372; 435/173.5; 514/183; 514/297; 514/455; 514/457; 424/529; 424/530; 424/531; 424/532; 424/533; 424/534; 549/282; 549/283; 549/285; 549/289

(58) Field of Classification Search ......... 422/22, 422/24, 28, 186.3, 292; 435/2, 238, 173.1, 435/173.5, 372; 514/183, 297, 455, 457; 424/529–534; 549/282–283, 285, 289
See application file for complete search history.

(56) References Cited

U.S. PATENT DOCUMENTS

| | | | |
|---|---|---|---|
| 683,690 A | 10/1901 | Johnson | 604/20 |
| 1,733,239 A | 10/1929 | Roberts | 607/93 |
| 1,961,700 A | 6/1934 | Moehler | 167/3 |
| 2,056,614 A | 10/1936 | Moehler | 21/18 |
| 2,111,491 A | 3/1938 | Kuhn et al. | 260/29 |
| 2,212,230 A | 8/1940 | Goldmann | 250/11 |
| 2,212,330 A | 8/1940 | Thomas | 250/52 |
| 2,340,890 A | 2/1944 | Lang et al. | 250/429 |
| 2,340,980 A | 2/1944 | Lang et al. | 250/429 |

(Continued)

FOREIGN PATENT DOCUMENTS

EP 0 066886 6/1982

(Continued)

OTHER PUBLICATIONS

Uehara K. et al. "Effect of adenine on the riboflavin-sensitized photoreaction. II. Effect of adenine on the photodynamic inactivation of transforming deoxyribonucleic acid in the presence of riboflavin," The Journal of Biochemistry, vol. 71, No. 5, 1972, pp. 805-810.

(Continued)

*Primary Examiner*—Richard Crispino
*Assistant Examiner*—Monzer R. Chorbaji
(74) *Attorney, Agent, or Firm*—Greenlee, Winner and Sullivan, P.C.

(57) ABSTRACT

Methods and apparatuses for treating fluids to inactivate microorganisms which may be present therein, said fluid containing one or more components selected from the group consisting of protein, blood and blood constituents are provided. The methods comprise adjusting the percentage of plasma in said fluid to a desired value; mixing an inactivation-effective, substantially non-toxic amount of an endogenous photosensitizer or endogenously-based derivative photosensitizer to said fluid; exposing said fluid to photoradiation of sufficient wavelength and energy to activate the photosensitizer, whereby said microorganisms are inactivated.

108 Claims, 35 Drawing Sheets

U.S. PATENT DOCUMENTS

| | | | |
|---|---|---|---|
| 2,654,735 A | 10/1953 | Funk et al. ............... 260/211.3 |
| 2,825,729 A | 3/1958 | Petering et al. .......... 260/251.5 |
| 3,189,598 A | 6/1965 | Yagi et al. ............... 260/211.3 |
| 3,456,053 A | 7/1969 | Crawford ..................... 424/89 |
| 3,683,177 A | 8/1972 | Veloz ......................... 250/43 |
| 3,683,183 A | 8/1972 | Vizzini et al. ............... 250/44 |
| 3,705,985 A | 12/1972 | Manning et al. .......... 250/106 S |
| 3,776,694 A | 12/1973 | Leittl ....................... 21/102 R |
| 3,852,032 A | 12/1974 | Urbach ......................... 21/54 |
| 3,864,081 A | 2/1975 | Logrippo .................. 21/102 R |
| 3,894,236 A | 7/1975 | Hazelrigg ................... 250/435 |
| 3,920,650 A | 11/1975 | Spencer et al. .......... 260/251.5 |
| 3,926,556 A | 12/1975 | Boucher ..................... 21/54 R |
| 3,927,325 A | 12/1975 | Hungate et al. ............. 250/435 |
| 4,124,598 A | 11/1978 | Hearst et al. ........... 260/343.21 |
| 4,139,348 A | 2/1979 | Swartz ..................... 23/232 E |
| 4,169,204 A | 9/1979 | Hearst et al. ............... 546/270 |
| 4,173,631 A | 11/1979 | Graham et al. ............. 424/180 |
| 4,181,128 A | 1/1980 | Swartz ................. 128/207.21 |
| 4,196,281 A | 4/1980 | Hearst et al. ................ 536/25 |
| 4,312,883 A | 1/1982 | Baccichetti et al. ........ 424/279 |
| 4,321,918 A | 3/1982 | Clark, II ................. 128/124 R |
| 4,321,919 A | 3/1982 | Edelson .................. 128/124 R |
| 4,336,809 A | 6/1982 | Clark ........................ 128/665 |
| 4,398,031 A | 8/1983 | Bender et al. ............... 549/282 |
| 4,398,906 A | 8/1983 | Edelson .......................... 604/6 |
| 4,402,318 A | 9/1983 | Swartz .......................... 604/6 |
| 4,407,282 A | 10/1983 | Swartz ........................ 604/20 |
| 4,421,987 A | 12/1983 | Herold ..................... 250/492.1 |
| 4,424,201 A | 1/1984 | Valinsky et al. .............. 424/3 |
| 4,428,744 A | 1/1984 | Edelson .......................... 604/6 |
| 4,456,512 A | 6/1984 | Bieler et al. ............. 204/162 R |
| 4,464,166 A | 8/1984 | Edelson .......................... 604/6 |
| 4,467,206 A | 8/1984 | Taylor et al. ................ 250/435 |
| 4,481,167 A | 11/1984 | Ginter et al. ................. 422/29 |
| 4,493,981 A | 1/1985 | Payne ........................ 219/450 |
| 4,568,328 A | 2/1986 | King .............................. 604/6 |
| 4,573,960 A | 3/1986 | Goss ............................. 604/6 |
| 4,573,961 A | 3/1986 | King .............................. 604/6 |
| 4,573,962 A | 3/1986 | Troutner ....................... 604/6 |
| 4,576,143 A | 3/1986 | Clark, III ..................... 128/1 R |
| 4,578,056 A | 3/1986 | King et al. ..................... 604/6 |
| 4,596,547 A | 6/1986 | Troutner ....................... 604/4 |
| 4,604,356 A | 8/1986 | Blake, II .................... 435/194 |
| 4,608,255 A | 8/1986 | Kahn et al. .................. 424/101 |
| 4,612,007 A | 9/1986 | Edelson .......................... 604/5 |
| 4,613,322 A | 9/1986 | Edelson .......................... 604/6 |
| 4,614,190 A | 9/1986 | Stanco et al. ................ 128/395 |
| 4,623,328 A | 11/1986 | Hartranft ....................... 604/4 |
| 4,642,171 A | 2/1987 | Sekine et al. ................ 204/298 |
| 4,645,649 A | 2/1987 | Nagao ...................... 422/186.3 |
| 4,648,992 A | 3/1987 | Graf et al. ................... 540/124 |
| 4,649,151 A | 3/1987 | Dougherty et al. ......... 514/410 |
| 4,651,739 A | 3/1987 | Oseroff et al. ............... 128/395 |
| 4,683,195 A | 7/1987 | Mullis et al. .................. 435/6 |
| 4,683,202 A | 7/1987 | Mullis ........................... 435/91 |
| 4,683,889 A | 8/1987 | Edelson ....................... 128/395 |
| 4,684,521 A | 8/1987 | Edelson ....................... 424/101 |
| 4,693,981 A | 9/1987 | Wiesehahn et al. .......... 435/238 |
| 4,695,460 A | 9/1987 | Holme ........................ 424/101 |
| 4,708,715 A | 11/1987 | Troutner et al. ................ 604/6 |
| 4,726,949 A | 2/1988 | Miripol et al. ............... 424/101 |
| 4,727,027 A | 2/1988 | Wiesehahn et al. .......... 435/173 |
| 4,737,140 A | 4/1988 | Lee et al. ........................ 604/4 |
| 4,748,120 A | 5/1988 | Wiesehahn ................... 435/173 |
| 4,775,625 A | 10/1988 | Sieber ........................ 435/238 |
| 4,788,038 A | 11/1988 | Matsunaga .................... 422/22 |
| RE32,874 E | 2/1989 | Rock et al. .................. 424/101 |
| 4,831,268 A | 5/1989 | Fisch et al. ............... 250/432 R |
| 4,833,165 A | 5/1989 | Louderback ................ 514/694 |
| 4,861,704 A | 8/1989 | Reemtsma et al. ............. 435/1 |
| 4,866,282 A | 9/1989 | Miripol et al. ........... 250/455.1 |
| 4,878,891 A | 11/1989 | Judy et al. ....................... 604/5 |
| 4,880,788 A | 11/1989 | Moake et al. ............... 514/150 |
| 4,915,683 A | 4/1990 | Sieber ......................... 128/665 |
| 4,921,473 A | 5/1990 | Lee et al. ....................... 494/27 |
| 4,930,516 A | 6/1990 | Alfano et al. ................ 128/665 |
| 4,946,438 A | 8/1990 | Reemtsma et al. ............ 604/53 |
| 4,948,980 A | 8/1990 | Wedekamp ............. 250/504 R |
| 4,950,665 A | 8/1990 | Floyd ........................ 514/222.8 |
| 4,952,812 A | 8/1990 | Miripol et al. ........... 250/455.1 |
| 4,960,408 A | 10/1990 | Klainer et al. ................. 604/4 |
| 4,961,928 A | 10/1990 | Holme et al. ............... 424/533 |
| 4,978,688 A | 12/1990 | Louderback ................ 514/722 |
| 4,986,628 A | 1/1991 | Lozhenko et al. ........ 350/96.29 |
| 4,992,363 A | 2/1991 | Murphy ......................... 435/2 |
| 4,994,367 A | 2/1991 | Bode et al. ..................... 435/2 |
| 4,998,931 A | 3/1991 | Slichter et al. ................ 604/20 |
| 4,999,375 A | 3/1991 | Bachynsky et al. ......... 514/455 |
| 5,011,695 A | 4/1991 | Dichtelmuller et al. ..... 424/529 |
| 5,017,338 A | 5/1991 | Surgenor ....................... 422/41 |
| 5,020,995 A | 6/1991 | Levy .......................... 433/215 |
| 5,030,200 A | 7/1991 | Judy et al. ....................... 604/5 |
| 5,039,483 A | 8/1991 | Sieber et al. ................. 422/28 |
| 5,041,078 A | 8/1991 | Matthews et al. .............. 604/4 |
| 5,089,146 A | 2/1992 | Carmen et al. .............. 210/782 |
| 5,089,384 A | 2/1992 | Hale ............................ 435/2 |
| 5,092,773 A | 3/1992 | Levy .......................... 433/224 |
| 5,095,115 A | 3/1992 | Grimmer et al. ............ 544/244 |
| 5,114,670 A | 5/1992 | Duffey ........................ 422/24 |
| 5,114,957 A | 5/1992 | Hendler et al. .............. 514/356 |
| 5,120,649 A | 6/1992 | Horowitz et al. ............ 435/713 |
| 5,123,902 A | 6/1992 | Müller et al. ................. 604/21 |
| 5,133,932 A | 7/1992 | Gunn et al. ................... 422/24 |
| 5,147,776 A | 9/1992 | Koerner, Jr. .................. 435/2 |
| 5,150,705 A | 9/1992 | Stinson ....................... 128/396 |
| 5,166,528 A | 11/1992 | Le Vay .................. 250/455.11 |
| 5,184,020 A | 2/1993 | Hearst et al. ........... 250/455.11 |
| 5,185,532 A | 2/1993 | Zabsky et al. ......... 250/455.11 |
| 5,192,264 A | 3/1993 | Fossel .......................... 604/4 |
| 5,216,251 A | 6/1993 | Matschke ............. 250/455.11 |
| 5,229,081 A | 7/1993 | Suda .......................... 427/186 |
| 5,232,844 A | 8/1993 | Horowitz et al. ......... 435/173.1 |
| 5,234,808 A | 8/1993 | Murphy ......................... 435/2 |
| 5,236,716 A | 8/1993 | Carmen et al. ............. 424/532 |
| 5,247,178 A | 9/1993 | Ury et al. .................... 250/438 |
| 5,248,506 A | 9/1993 | Holme et al. ............... 424/533 |
| 5,258,124 A | 11/1993 | Bolton et al. ................ 210/748 |
| 5,269,946 A | 12/1993 | Goldhaber et al. ......... 210/767 |
| 5,273,713 A | 12/1993 | Levy .......................... 422/22 |
| 5,288,605 A | 2/1994 | Lin et al. .................... 435/902 |
| 5,288,647 A | 2/1994 | Zimlich, Jr. et al. ........ 436/174 |
| 5,290,221 A | 3/1994 | Wolf, Jr. et al. ................ 604/4 |
| 5,300,019 A | 4/1994 | Bischof et al. ................. 604/4 |
| 5,304,113 A | 4/1994 | Sieber et al. ................... 604/4 |
| 5,318,023 A | 6/1994 | Vari et al. .................... 128/633 |
| 5,340,716 A | 8/1994 | Ullman et al. ................. 435/6 |
| 5,342,752 A | 8/1994 | Platz et al. .................... 435/2 |
| 5,344,752 A | 9/1994 | Murphy ......................... 435/2 |
| 5,344,918 A | 9/1994 | Dazey et al. ................ 530/381 |
| 5,358,844 A | 10/1994 | Stossel et al. .................. 435/2 |
| 5,360,734 A | 11/1994 | Chapman et al. ........... 435/238 |
| 5,366,440 A | 11/1994 | Fossel .......................... 604/4 |
| 5,376,524 A | 12/1994 | Murphy et al. ................ 435/2 |
| 5,378,601 A | 1/1995 | Gepner-Puszkin ............. 435/2 |
| 5,418,130 A | 5/1995 | Platz et al. .................... 435/2 |
| 5,419,759 A | 5/1995 | Naficyn ........................ 604/5 |
| 5,427,695 A | 6/1995 | Brown ....................... 210/805 |
| 5,433,738 A | 7/1995 | Stinson ......................... 607/92 |
| 5,459,030 A | 10/1995 | Lin et al. ....................... 435/2 |
| 5,466,573 A | 11/1995 | Murphy et al. ................ 435/2 |
| 5,474,891 A | 12/1995 | Murphy ......................... 435/2 |
| 5,482,828 A | 1/1996 | Lin et al. ....................... 435/2 |
| 5,487,971 A | 1/1996 | Holme et al. .................. 435/2 |

| | | | |
|---|---|---|---|
| 5,498,520 A | 3/1996 | Chapman | 435/5 |
| 5,503,721 A | 4/1996 | Hearst et al. | 204/157.6 |
| 5,516,629 A | 5/1996 | Park et al. | 435/2 |
| 5,527,704 A | 6/1996 | Wolf, Jr. et al. | 435/283.1 |
| 5,536,238 A | 7/1996 | Bischof | 604/6 |
| 5,545,516 A | 8/1996 | Wagner | 435/2 |
| 5,547,635 A | 8/1996 | Duthie, Jr. | 422/24 |
| 5,550,111 A | 8/1996 | Suhadolnik et al. | 514/44 |
| 5,556,958 A | 9/1996 | Carroll et al. | 536/25.3 |
| 5,556,993 A | 9/1996 | Wollowitz et al. | 549/282 |
| 5,557,098 A | 9/1996 | D'Silva | 250/222.1 |
| 5,569,579 A | 10/1996 | Murphy | 435/2 |
| 5,571,666 A | 11/1996 | Floyd et al. | 435/2 |
| 5,587,490 A | 12/1996 | Goodrich, Jr. et al. | 549/282 |
| 5,593,823 A | 1/1997 | Wollowitz et al. | 435/2 |
| 5,597,722 A | 1/1997 | Chapman et al. | 435/238 |
| 5,607,924 A | 3/1997 | Magda et al. | 514/44 |
| 5,622,867 A | 4/1997 | Livesey et al. | 436/18 |
| 5,624,435 A | 4/1997 | Furumoto et al. | 606/10 |
| 5,628,727 A | 5/1997 | Hakky et al. | 604/6 |
| 5,639,376 A | 6/1997 | Lee et al. | 210/645 |
| 5,639,382 A | 6/1997 | Brown | 210/739 |
| 5,643,334 A | 7/1997 | Eckhouse et al. | 607/88 |
| 5,652,096 A | 7/1997 | Cimino | 435/6 |
| 5,653,887 A | 8/1997 | Wahl et al. | 210/745 |
| 5,654,443 A | 8/1997 | Wollowitz et al. | 549/282 |
| 5,658,530 A | 8/1997 | Dunn | 422/24 |
| 5,658,722 A | 8/1997 | Margolis-Nunno et al. | 435/2 |
| 5,683,661 A | 11/1997 | Hearst et al. | 422/186.3 |
| 5,683,768 A | 11/1997 | Shang et al. | 428/35.2 |
| 5,686,436 A | 11/1997 | Van Dyke | 514/171 |
| 5,688,475 A | 11/1997 | Duthie, Jr. | 422/186.3 |
| 5,691,132 A | 11/1997 | Wollowitz et al. | 435/2 |
| 5,698,524 A | 12/1997 | Mach et al. | 514/22 |
| 5,698,677 A | 12/1997 | Eibl et al. | 530/381 |
| 5,702,684 A | 12/1997 | McCoy et al. | 424/10.3 |
| 5,707,401 A | 1/1998 | Talmore | 607/88 |
| 5,709,653 A | 1/1998 | Leone | 604/20 |
| 5,709,991 A | 1/1998 | Lin et al. | 435/2 |
| 5,712,086 A | 1/1998 | Horowitz et al. | 435/2 |
| 5,714,328 A | 2/1998 | Magda et al. | 435/6 |
| 5,739,013 A | 4/1998 | Budowsky et al. | 435/91.1 |
| 5,756,553 A | 5/1998 | Iguchi et al. | 514/772.3 |
| 5,762,867 A | 6/1998 | D'Silva | 422/44 |
| 5,772,960 A | 6/1998 | Ito et al. | 422/41 |
| 5,789,150 A | 8/1998 | Margolis-Nunno et al. | 435/2 |
| 5,789,601 A | 8/1998 | Park et al. | 549/283 |
| 5,798,238 A | 8/1998 | Goodrich, Jr. et al. | 435/173.3 |
| 5,798,523 A | 8/1998 | Villenueve et al. | 250/234 |
| 5,811,144 A | 9/1998 | Bordeleau et al. | 426/330.4 |
| 5,817,519 A | 10/1998 | Zelmanovic et al. | 436/63 |
| 5,827,644 A | 10/1998 | Floyd et al. | 435/2 |
| 5,834,198 A | 11/1998 | Famulok et al. | 435/6 |
| 5,843,459 A | 12/1998 | Wang et al. | 424/231.1 |
| 5,846,961 A | 12/1998 | Van Dyke | 514/171 |
| 5,854,967 A | 12/1998 | Hearst et al. | 422/186.3 |
| 5,866,074 A | 2/1999 | Chapman et al. | 422/82.09 |
| 5,868,695 A | 2/1999 | Wolf, Jr. et al. | 604/4 |
| 5,869,701 A | 2/1999 | Park et al. | 549/283 |
| 5,871,900 A | 2/1999 | Wollowitz et al. | 435/2 |
| 5,876,676 A | 3/1999 | Stossel et al. | 422/12 |
| 5,891,705 A | 4/1999 | Budowsky et al. | 435/238 |
| 5,908,742 A | 6/1999 | Lin et al. | 435/2 |
| 5,922,278 A | 7/1999 | Chapman et al. | 422/22 |
| 5,935,092 A | 8/1999 | Sun et al. | 604/4 |
| 5,976,884 A | 11/1999 | Chapman et al. | 436/34 |
| 6,020,333 A | 2/2000 | Berque | 514/251 |
| 6,087,141 A | 7/2000 | Margolis-Nunno et al. | 435/173.3 |
| 6,187,572 B1* | 2/2001 | Platz et al. | |
| 6,235,508 B1* | 5/2001 | Sowemimo-Coker et al. | |
| 6,258,577 B1* | 7/2001 | Goodrich, Jr. et al. | |
| 6,268,120 B1* | 7/2001 | Platz et al. | |
| 6,277,337 B1* | 8/2001 | Goodrich, Jr. et al. | |
| 6,548,241 B1* | 4/2003 | McBurney et al. | |

FOREIGN PATENT DOCUMENTS

| | | |
|---|---|---|
| EP | 0 124 363 | 4/1984 |
| EP | 0 196 515 A1 | 3/1986 |
| EP | 0 196 515 | 8/1986 |
| EP | 0196515 | 10/1986 |
| EP | 0 491/757 | 9/1990 |
| EP | 0 525 138 B1 | 12/1991 |
| EP | 0 679 398 A | 2/1995 |
| EP | 0679398 | 11/1995 |
| EP | 0 801 072 A2 | 10/1997 |
| FR | 2674753 | 10/1992 |
| FR | WO 94/07499 | 4/1994 |
| FR | 2715303 | 7/1995 |
| FR | 2718353 | 10/1995 |
| WO | WO 89/06702 | 7/1989 |
| WO | WO 91/02529 | 3/1991 |
| WO | WO 92/11057 | 7/1992 |
| WO | WO 92/17173 | 10/1992 |
| WO | 94/07426 | 4/1994 |
| WO | WO 95/02325 | 1/1995 |
| WO | WO95/11028 | 4/1995 |
| WO | WO 95/12973 | 5/1995 |
| WO | WO 95/16348 | 6/1995 |
| WO | WO 96/14740 | 5/1996 |
| WO | WO 96/39816 | 12/1996 |
| WO | WO 97/07674 | 3/1997 |
| WO | WO 97/22245 | 6/1997 |
| WO | WO 97/36581 | 10/1997 |
| WO | WO 97/36634 | 10/1997 |
| WO | WO 97/46271 | 12/1997 |
| WO | WO 98/30545 | 7/1998 |
| WO | WO 98/31219 | 7/1998 |
| WO | WO 99/11305 | 3/1999 |
| WO | WO 00/04930 | 2/2000 |
| WO | WO 00/20045 | 4/2000 |
| WO | 01/28599 | 4/2001 |

OTHER PUBLICATIONS

Uehara K. et al. "Effect of adenine on the riboflavin-sensitized photoreaction. II. Effect of adenine on the photodynamic inactivation of yeast alcohol dehydrogenase in the presence of riboflavin," *The Journal of Vitaminology*, vol. 17, No. 3, 1971, pp. 148-154.

Reinhardt A. et al. "Virucidal activity of retinal," *Antimicrobial Agents and Chemotherapy*, vol. 16, No. 3, Sep. 1979, pp. 421-423.

U.S. Appl. No. 09/357,188, filed Jul. 20, 1999, Goodrich et al.

U.S. Appl. No. 09/119,666, filed Jul. 21, 1998, Goodrich et al.

U.S. Appl. No. 08/924,519, filed Sep. 5, 1997, Hannon.

Abdurashidova, G.G. et al., "Polynucleotide-protein itneractions in the translation system. Identification of proteins interacting with tRNA in the A- and P-sites of E. coli ribosomes," (1979) *Nucleic Acids Res.* 6(12):3891-3909.

Berezovskii, V.M. and Eremenko, T.V. (Nov. 1961), "Studies in the Allo- and Isoalloxazine Series. IV. New Synthesis of 2'-Desoxyriboflavin and Synthesis," *J. Gen. Chem. USSR* 31(11):3575-3578.

Bhatia, J. et al. (May/Jun. 1983), "Riboflavin Enhances Photo-oxidation of Amino Acids under Simulated Clinical Conditions," *J. Parenteral Enteral Nutr.* 7(3):277-279.

Brodie, A.F. and Watanabe, T., (1966), "Mode of action of vitamin K in microorganisms," *Vitam. Horm.* 24:447-463.

Budowsky, E.I. et al., (1986), "Induction of polynucleotide-protein cross-linkages by ultraviolet irradiation," *Eur. J. Biochem.* 159:95-101.

Budowsky, E.I. and Abdurashidova, G.G., (1989), "Polynucleotide-Protein Cross-Links Induced by Ultraviolet Light and Their Use for Structural Investigation of Nucleoproteins," *Progress in Nucleic Acid Res. and Mol. Biol.* 37:1-65.

Budowsky, E.I. (1991), "Problems and Prospects for Preparation of Killed Antiviral Vaccines," *Adv. Virus Res.* 39:255-290.

Budowsky, E.I. et al. (1991), "Principles of selective inactivation of viral genome. VI. Inactivation of the infectivity of the influenza virus by the action of β-propiolactone," *Vaccine* 9:398-402.

Budowsky, E.I. et al. (July 1991), "Principles of selective inactivation of viral genome. VII. Some peculiarities in determination of viral suspension infectivity during inactivation by chemical agents," *Vaccine* 9:473-476.

Budowsky, E.I. et al. (1993), "Principles of selective inactivation of viral genome. VIII. The influence of β-propiolactone on immunogenic and protective activities of influenza virus," *Vaccine* 11(3):343-348.

Budowsky, E.I. et al., "Preparation of cyclic 2',3'-monophosphates of oligoadenylates $(A2'p)_n A>p$ and $A3'p(A2'p)_{n-1} A>p$," (1994) *Eur. J. Biochem.* 220:97-104.

Cadet, J. et al. (1983), "Mechanisms and Products of Photosensitized Degradation of Nucleic Acids and Related Model Compounds," *Israel J. Chem.* 23:420-429.

Cairns, W.L. and Metzler, D.E. (Jun. 1971), "Photochemical Degradation of Flavins. VI. A New Photoproduct and Its Use in Studying the Photolytic Mechanism," *J. Am. Chem. Soc.* 93:2772-2777.

Cerman, J. and Hais, I.M. (Mar. 1972), Esters of 6,7-Dimethyl-9-hydroxymethylisoalloxazine as Photodegradation Products of Riboflavin and Formylmethylflavin in Media Containing Fatty Acids,: *J. AM. Chem. Soc.* 94(5):1741-1742.

Chastain, J.L. and McCormick, D.B. (1991) IN *Chemistry and Biochemistry of Flavoinzymes*, vol. I, Chapter 6, Muller, F. (ed.), CRC Press, Boston, pp. 195-200.

Chastain, J.L. and McCormick, D.B. (1987), "Clarification and Quantitation of Primary (Tissue) and Secondary (Microbial) Catabolites of Riboflavin That are Excreted in Mammalian (Rat) urine," *J. Nutr.*, pp. 468-475.

Chow, C.S. and Barton, J.K., (Jun. 1992), "Recognition of G-U mismatches by tris(4,7-diphenyl-1,10-phenanthroline)rhodium(III)," *Biochemistry* 31(24):5423-5429.

Deutsch, E., "Vitamin K in medical practice: adults," (1966) *Vitam. Horm.* 24:665-680.

Edwards, A.M. et al. (1994), "Visible light effects on tumoral cells in a culture medium enriched with tryptophan and riboflavin," *J. Photochem. Photobiol. B:Biol.* 24:179-186.

Ennever et al. (1983), "Potential for Genetic Damage from Multivitamin Solutions Exposed to Phototherapy Illumination," *Pediatr. Res.* 17:192-194.

Ennever, J.F. and Speck, W.T. (1983), "Short Communication. Photochemical Reactions of Riboflavin: Covalent Binding to DNA and to Poly (dA)·Poly (dT)," *Pediatr. Res.* 17:234-236.

Everett et al. (1952), "Aryl-2-halogenoalkylamines. Part XII. Some Carboxylic Derivatives of NN-Di-2-chloroethylaniline," *J. Chem. Soc.*, pp. 2386-2392.

Friedman et al., (1995), "Reducing the infectivity of blood components—what we have learned", *Immun. Invest.* 24(1&2):49-71.

Fritz et al. (1987), "Photochemical Properties of Flavin Derivatives," *Photochem. Photobiol.* 45(1):113-117.

Fritz et al. (1987), "Triplet Lifetimes of Some Flavins," *Photochem. Photobiol* 45(4):539-541.

Galston, A.W. (1949), "Riboflavin-sensitized Photooxidation of Indole-acetic Acid and Related Compounds," *Proc. Natl. Acad. Sci.* 35:10-17.

Ghiron, C.A. and Spikes, J.D., (1965), "The flavin-sensitized photoinactivation of trypsin", *Photochem. And Photobio.* 4:13-26.

Gomyo, T. and Fujimaki, M. (1970), "Studies on Changes of Protein by Dye Sensitized Photooxidation, Part III. On the Photodecomposition Products of Lysozyme," *Agr. Biol. Chem.* 34(2):302-309.

Goodrich, R.P. and Platz, M.S. (1997), "The design and development of selective, photoactivated drugs for sterilization of blood products," *Drugs of the Future* 22(2):159-171.

Gordon-Walker et al. (1970), "Excited States of Flavins Characterised by Absorption, Prompt and Delayed Emission Spectra," *Eur. J. Biochem.* 13:313-321.

Halwer, M. (Oct. 1951), "The Photochemistry of Riboflavin and Related Compounds," *J. Am. Chem. Soc.* 73:4870-4874.

Hanson, C.V., (Mar. 1979), "Photochemical Inactivation of Deoxyribonucleic and Ribonucleic Acid Viruses by Cholorpromazine," *Antimicrob. Agent Chemother*, 15(3):461-464.

Hemmerich, V.P. (1964), "Flavosemichinon-Metallchelate: Modelle zür Erklärung der "active site" in den mitochondrialen Flavoenzymen Zum Verhalten des Riboflavins gegen Metallionen III," *Helv. Chim. Acta* 47(55):464-465 (In German).

Herfeld et al. (1994), "Poly (pyrrolecarboxamides) linked to photacvtivable chromophore isoalloxazine. Synthesis, selective binding, and DNA cleaving properties," Bioconjugate chem. 5(1):67-76 (CAS Printout).

Herfeld et al. (1998), "Synthesis, DNA-binding properties and cytotoxic activity of flavin-oligopyrrolecarboxamide and flavin-oligoimidazolecarboxamide conjugates," *Anti-Cancer Drug Design* 13:337-359.

Herfeld et al. (1998), "Synthesis, DNA-binding properties and cytotoxic activity of flavin-oligopyrrolecarboxamide and flavin-oligoimidazolecarboxamide conjugates," *Anti-Cancer Drug Design* 13:337-359 (CAS Printout).

Hoffman, M.E. and Meneghini, R. (1979), "DNA Strand Breaks in Mammalian Cells Exposed to Light in the Presence of Riboflavin and Tryptophan," *Photochemistry and Photobiology* 29:299-303.

Holström (Mar. 1964), "Spectral studies of the photobleaching of riboflavin phosphate," *Arkiv för Kemi* 22(23):281-301.

Ito et al. (Jun. 1993), "Hydroxydeoxyguanosine Formation at the 5' Site of 5'-GG-3' Sequences in Double-stranded DNA by UV Radiation with Riboflavin," *J. Biol. Chem.* 285(18):13221-13227.

Ivanchenko, V.A. et al. (Aug. 1975), "The photochemistry of purine components of nucleic acids. I. The efficiency of photolysis of adenine and guanine derivatives in aqueous solution," *Nucleic Acids Res.* 2(8):1365-1373.

Joshi, P.C. (1985), "Comparison of the DNA-damaging property of photosensitized riboflavin via singlet oxygen ($^1O_2$) and superoxide radical ($O_i$) mechanisms," *Toxicology Letters* 26:211-217.

Kabuta, H. et al. (1978), "Inactivation of viruses by dyes and visible light," *Chem. Abstracts* 87(1), Abstract No. 400626.

Kale, H. et al. (1992), "Assessment of the genotoxic potential of riboflavin and lumiflavin; B. Effect of light," *Mutation Res.* 298:17-23.

Karrer, V.P. et al. (1934), "Weltere Synthesen Lactoflavin-ähnlicher Verbindungen II," *Helv. Chim. Acta* 16:1516-1522 (In German).

Kasai, S. et al. (1988), "Intestinal Absorption of Riboflavin, Studied by an In Situ Circulation System Using Radioactive Analogues," *J. Nutr. Sci. Vitaminol.* 34:265-280.

Kasai,, H. and Yamaizumi, Z. (1992), "Photosensitized Formation of 7,8-Dihydro-8-oxo-2'-deoxyguanosine (8-Hydroxy-2'-deoxyguanosine) in DNA by Riboflavin: A Non Singlet Oxygen Mediated Reaction," *J. Am. Chem. Soc.* 114:9692-9694.

Kasai, S. et al. (1990), "Purification, Properties, and Function of Flavokinase from Rat Intestinal Mucosa," *J. Biochem*.107(2):298-303.

Kawai, F. and Tanaka, K (1970), "Riboflavin -Indoles Interaction in Acid Solution," *J. Vitamin.* 16:215-218.

Kimmich, G.A. and McCormick, D.B. (1963), "Paper Chromatography of Flavin Analogues," *J. Chromatogr.* 12:394-400.

Kindack, D.G. et al. (1991), "Separation, identification and determination of lumichrome in swine feed and kidney," *Food Additives and Contaminants* 8(6):737-748.

Klebanoff, M.A. et al. (Sep. 1993), "The risk of childhood cancer after neonatal exposure to vitamin K," *New Eng.. J. Med.* 329(13):905-908.

Kobayashi et al. (1983), "The molecular mechanism of mutation. Photodynamic action of flavins on the RNA-synthesizing system," *Chem. Abstracts* 98(1), Abstract No. 1200.

Korycka-Dahl, M. and Richardson, T. (1980), "Photodegradation of DNA with fluorescent light in the presence of riboflavin, and photoprotection by flavin triplet-state quenchers," *Biochimica et Biophysica Acta* 610:229-234.

Kostenbauder, H.B. et al. (Sep. 1965), "Photobinding and Photoreactivity of Riboflavin in the Presence of Macromolecules," *J. Pharm. Sci.* 54(9):1243-1251.

Kovalsky, O.I. and Budowsky, E.I. (1990), "Laser (Two-Quantum) Photolysis of Polynucleotides and Nucleoproteins: Quantitative Processing of Results,", *Photochemistry and Photobiology* 51(6):659-665.

Koziol, J. (1991), "Synthesis of Alloxazine Derivatives by Dealkylation of Isoalloxazines at N-10," Bull. Pol. Acad. Sci. 39(1):37-39.

Kuratomi, K. and Kobayashi, Y. (1977), "Studies on the Interactions Between DNA and Flavins," *Biochemica et Biophysica Acta* 476:207-217.

Kurl, R. and Villee, C.A. (1985), "A Metabolite of Riboflavin Binds to the 2,3,7,8-Tetrachlorodibenzo-p-dioxin (TCDD) Receptor," *Pharmacology* 30:241-244.

Leontis, N.B. and Westhof, E. (1998), "The 5S rRNA loop E: chemical probing and phylogenetic data versus crystal structure," *RNA* 4:1134-1153.

Lim, A.C. and Barton, J.K. (1993), "Chemical probing of tDNA$^{Phe}$ with transition metal complexes: a structural comparison of RNA and DNA," *Biochemistry* 32(41):11029-11034.

Maddox, J. (Oct. 1991), "The working of vitamin K," *Nature* 353(6346):695.

Malik et al., (1990), "New trends in photobiology—bactericidal effects of photoactivated porphyrins—an alternative approach to antimicrobial drugs," *J. Photochem. Photobiol. Pt. B:Biology*, 5:281-293.

Mallesh, K. et al. (1989), "Synthesis and Biological Activities of Some New Substituted Alloxazines and Isoalloxazines: Part 1," *Acta Ciencia Indica* XV(2):67-74.

Matthews, J.L. et al. (1988), "Photodynamic therapy of viral contaminants with potential for blood banking applications," *Transfusion* 28(1):81-83.

McCord, E.F. (1984), "Chemically induced dynamic nuclear polarization studies of yeast," *Biochemistry* 23:1935-1939.

McCormick, D.B. (Apr. 1970), "Flavin Derivatives via Bromination of the 8-Methyl Substituent (1)," *J. Heter. Chem.* 7:447-450.

Merenstein, G.B. et al. (1993), (Vitamin K Ad Hoc Task Force), "Controversies concerning vitamin K and the newborn," *Pediatrics* 91(5):1001-1003.

Merrifield, L.S. and Yang, H.Y. (Sep. 1965), "Factors affecting the antimicrobial activity of vitamin K5," *Appl. Microbiol.* 13(5):766-770.

Merrifield, L.S. and Yang, H.Y. (Sep. 1965), "Vitamin $K_5$ as a fungistatic agent," *Applied Microbiol.* 13(5):660-662.

Mitsuda et al. (1970), "Riboflavin -Indoles Interaction in Acid Solution," *J. Vitamin.* 16:215-218.

Moonen, C.T.W. et al. (Nov. 1982), "A photo-CIDNP study of the active sites of *Megasphaera elsdenii* and *Clostridium MP* flavodoxins," *FEBS Lett.* 149(1):141-146.

Murata, A. et al. (1983), "Effect of vitamins other than vitamin C on viruses: virus-inactivating activity of vitamin K5," *J. Nutr. Sci. Vitaminol* (Tokyo) 29(6):721-724.

Murthy, Y.V.S.N. and Massey, V. (Dec. 1995), "Chemical Modification of the N-10 Ribityl Side Chain of Flavins," *J. Biol. Chem.* 270(48):28586-28594.

Naseem, I. et al. (1988), "Effect of alkylated and intercalated DNA on the generation of superoxide anion by riboflavin," *Bioscience Reports* 8(5):485-492.

Nogami, H. et al. (1970), "Pharmacokinetic Aspects of Biliary Excretion. Dose Dependency of Riboflavin in Rat," *Chem. Pharm. Bull.* 18:228-234.

North, J. et al. (1993), "New Trends in Photobiology (Invited Review)," *J. Photochem. Photobiol. B: Biol.* 17:99-108.

Ohkawa, H. et al. (Feb. 1983), "New Metabolites of Riboflavin Appeared in Rat Urine," *Biochem. Intl.* 6(2):239-247.

Oka, M. and McCormick, D.B. (1985), "Urinary Lumichrome-Level Catabolites of Riboflavin are due to Microbial and Photochemical Events and Not Rat Tissue Enzymatic Cleavage of the Ribityl Chain," *J. Nutr.*, 115:496-499.

Ono, S. et al. (Feb. 1986), "Effects of Aging on the Formation of Ester Forms of Riboflavin in the Rat Lens," *Internat. J. Vit. Nutr. Res.* 56:259-262.

Parks, O.W. and Allen, C. (1977), "Photodegradation of Riboflavin to Lumichrome in Milk Exposed to Sunlight," *J. Dairy Sci.* 60(7):1038-1041.

Peak, J.G. et al. (1984), "DNA Breakage Caused by 334-nm Ultraviolet Light is Enhanced by Naturally Occurring Nucleic Acid Components and Nucleotide Coenzymes," *Photochemistry and Photobiology* 39(5):713-716.

Piette, J. et al. (1981), "Alteration of Guanine Residues During Proflaving Mediated Photosensitization of DNA," *Photochemistry and Photobiology* 33:325-333.

Piette, J. et al. (1979), "Production of Breaks in Single- and Double-Stranded Forms of Bacteriophage φX174 DNA by Proflavine and Light Treatment," *Photochemistry and Photobiology* 30:369-378.

Pratt, R. et al. (Mar. 1950), "Vitamin $K_5$ as an Antimicrobial Medicament and Preservative," *J. Am. Pharm. Ass'n* 39(3):127-134.

Product advertisement for "Ultracure 100SS Plus Specifications," EFOS USA, Inc., Williamsville, NY, USA.

Radda, G.K. and Calvin, M. (Mar. 1964), "Chemical and Photochemical Reductions of Flavin Nucleotides and Analogs," *Biochem.* 3(3):384-393.

Rivlin, R.S. (Aug. 1970), "Riboflavin Metabolism," *New Engl. J. Med.* 283(9): 463-472.

Roughead, Z K. and McCormick, D.B. (1990), "Qualitative and Quantitative Assessment of Flavins in Cow's Milk," *J Nutr.*, pp. 382-388.

Salim-Hanna, M. et al. (Jan. 1987), "Obtention of a Photo-Induced Adduct Between a Vitamin and an Essential Aminoacid. Binding of Riboflavin to Tryptophan," *Internat. J. Vit. Nutr. Res.* 57:155-159.

Sato, K. et al. (Oct. 1995), "The Primary Cytotoxicity in Ultraviolet-A-Irradiated Riboflavin Solution is Derived from Hydrogen Peroxide," *J. Investig. Dermatol.* 105(4):608-612.

Scheindlin, S. et al. (Aug. 1952), "The Action of Riboflavin on Folic Acid," *J. Am. Pharm. Assn.* XLI:420-427.

Schoo, H.F.M. and Challa, G. (Jan. 1992), "Flavin-Containing Polyanions: Synthesis, Activity, and Immobilization in Polyelectrolye Complexes," *Macromolecules* 25:1633-1638.

Silva, E. et al. (1994), "Riboflavin-sensitized photoprocesses of tryptophan," *J. Photochem. Photobiol. B: Biol.* 23:43-48.

Silva, E. and Gaule, J. (1977), "Light-Induced Binding of Riboflavin to Lysozyme," *Rad. Environm. Biophys.* 14:303-310.

Silva, E. et al. (1991), "A light-Induced Tryptophan-Riboflavin Binding: Biological Implications," in *Nutritional and Toxicological Consequences of Food Processing*, Friedman, M. (ed.), Plenum Press, New York, pp. 33-48.

Shwartzman, G., "(1948)Antibacterial Properties of 4-Amino-2-Methyl-1-Naphthol Hydrochloride," *Proc. Soc. Exp. Biol. Med.* 67:376-378.

Simukova, N.A. and Budowsky, E.I., (1974)"Conversion of Non-Covalent Interactions in Nucleoproteins into Covalent Bonds: UV-Induced Formation of Polynucleotide-Protein Crosslinks in Bacteriophage Sd Virions," *FEBS Letters* 38(3):299-303.

Smith, E.C. and Metzler, D.E. (1963), "The Photochemical Degradation of Riboflavin," *J. Am. Chem. Soc.* 85:3285-3288.

Song, P-S. and Metzler, D.E. (1967), "Photochemical Degradation of Flavins—IV. Studies of the Anaerobic Photolysis of Riboflavin," *Photochem. Photobiol.* 6:691-709.

Spranger, J. (1993), "Does vitamin K cause cancer?" *Eur. J. Pediatr.* 152(2):174.

Speck, W.T. et al. (1976), "Further Observations on the Photooxidation of DNA in the Presence of Riboflavin," *Biochimica et Biphysica Acta* 435:39-44.

Steczko, J. and Ostrowski, W. (1975), "The Role of Tryptophan Residues and Hydrophobic Interaction in the Binding of Fiboflavin in Egg Yolk Flavoprotein," *Biochim. Biophys. Acta* 393:253-266.

Swinehart, J.H. and Hess, G.P. (1965), "Riboflavin-Tryptophan Complex Formation as a Criterion for "Buried" and "Exposed" Tryptophyl Residues in Proteins," *Biochem. Biophys. Acta* 104:205-213.

Tapia, G. and Silva, E. (1991), "Photo-induced riboflavin binding to the tryptophan residues of bovine and human serum albumins," *Radiat. Environ. Biophys.* 30:131-138.

Toyosaki, T. and Hayashi, A. (1993), "Structural analysis of the products of milk riboflavin photolysis," *Milchwissenschaft* 48(11):607-609.

Treadwell, G.E. et al. (1968), "Photochemical Degradation of Flavins. V. Chromatographic Studies of the Products of Photolysis of Riboflavin," *J. Chromatog.* 35:376-388.

Treadwell, G.E., Jr. and Metzler, D.E. (1972), "Photoconversion of Riboflavin to Lumichrome in Plant Tissues," *Plant Physiol.* 49:991-993.

Tsugita, A. et al. (1965), "Photosensitized inactivation of ribonucleic acids in the presence of riboflavin," *Biochim. Biophys. Acta* 103:360-363.

Tyrakowska et al. (Jan. 1993), "A Fluorescence Study of Lumichrome Phototautomerism in Dodecylammonium Propionate Reversed Micelles," *J. Photochem. Photobiol. A.* 72:235-241.

Van Schagen, C.G. et al. (1982), "Photochemically Induced Dynamic Nuclear Polarization Study on Flavin Adenine Dinucleotide and Flavoproteins," *Biochemistry* 21(2):402-407.

Vest, M. (1966), "Vitamin K in Medical Practice: Pediatrics," *Vitam. Horm.* 24:649-663.

Warburg, V.O. and Christian, W. (1932), "Über das neue Oxydationsferment," *Naturewiss* 20:980-981 (In German).

Webb, R.B. and Malina, M.M. (1967), "Mutagenesis in *Escherichia coli* by Visible Light," *Science* 156:1104-1105.

Woodcock, E.A. et al. (1982), "Riboflavin Photochemical Degradation in Pasta Measured by High Performance Liquid Chromatography," *J. Food Sci.* 47:545-549.

Yang, C.S. et al. (1964), "Microbiological and Enzymatic Assays of Riboflavin Analogues," *J. Nutrition* 64:167-172.

Yang, H.Y. et al. (Oct. 1958), "Vitamin $K_5$ as a Food Preservative," *Food Technology* 501-504.

\* cited by examiner

FIG. 31

METHOD AND APPARATUS FOR INACTIVATION OF BIOLOGICAL CONTAMINANTS USING PHOTOSENSITIZERS

BACKGROUND OF THE INVENTION

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, anti-thrombin III, cryoprecipitate, human plasma protein fraction, albumin, immune serum globulin, prothrombin complex, plasma growth hormones, and other components isolated from blood. Blood screening procedures may miss contaminants, and sterilization procedures which do not damage cellular blood components but effectively inactivate all infectious viruses and other microorganisms have not heretofore been available.

In addition, a system that uses the same chemistry to inactivate microorganisms in different fluids, for example separate blood components, is desired for many reasons, including ease of use in a blood bank setting. This type of system has not heretofore been available. It is also desired that the inactivation treatment be easily implemented in a blood bank setting, and produce inactivation in a short period of time.

Some methods of decontaminating blood have been described. Solvent detergent methods of blood component decontamination work by dissolving phospholipid membranes surrounding viruses such as HIV, and do not damage protein components of blood; however, if blood cells are present, such methods cannot be used because of damage to cell membranes.

The use of photosensitizers, compounds which absorb light of a defined wavelength and transfer the absorbed energy to an energy acceptor, has been proposed for blood component sterilization. For example, European Patent application 196,515 published Oct. 8, 1986, suggests the use of non-endogenous photosensitizers such as porphyrins, psoralens, acridine, toluidines, flavine (acriflavine hydrochloride), phenthiazine derivatives, and dyes such as neutral red and methylene blue, as blood additives. Protoporphyrin, which occurs naturally within the body, can be metabolized to form a photosensitizer; however, its usefulness is limited in that it degrades desired biological activities of proteins. Chlorpromazine is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. No. 5,607,924 issued Mar. 4, 1997 and U.S. Pat. No. 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The mechanism of action of such photosensitizers is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of such photosensitizers is that they attack cell membranes of desirable components of fluids to be decontaminated, such as red blood cells, and the singlet oxygen also attacks desired protein components of fluids being treated. U.S. Pat. No. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued Jun. 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses the problem of prevention of damage to other blood components.

Photosensitizers which attack nucleic acids are known to the art. U.S. Pat. No. 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. This patent fails to disclose an apparatus for decontaminating blood on a flow-through basis. U.S. Pat. No. 5,798,238 to Goodrich, Jr., et al., discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin (7,8-dimethyl-10-ribityl isoalloxazine) has been reported to attack nucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217. Hoffmann, M. E., et al. (1979), "DNA Strand Breaks in Mammalian Cells Exposed to Light in the Presence of Riboflavin and Tryptophan," Photochemistry and Photobiology 29:299–303 describes the use of riboflavin and tryptophan to induce breaks in DNA of mammalian cells after exposure to visible fluorescent light or near-ultraviolet light. The article states that these effects did not occur if either riboflavin or tryptophan was omitted from the medium. DNA strand breaks upon exposure to proflavine and light are reported in Piette, J. et al. (1979), "Production of Breaks in Single- and Double-Stranded Forms of Bacteriophage ΦX174 DNA by Proflavine and Light Treatment," Photochemistry and Photobiology 30:369–378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325–333.

J. Cadet, et al. (1983), "Mechanisms and Products of Photosensitized Degradation of Nucleic Acids and Related Model Compounds," Israel J. Chem. 23:420–429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. Riboflavin is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229–234 also discloses that active oxygen species are not directly involved in DNA scission by riboflavin. Peak, J. G., et al. (1984), "DNA Breakage Caused by 334-nm Ultraviolet Light is Enhanced by Naturally Occurring Nucleic Acid Components and Nucleotide Coenzymes," Photochemistry and Photobiology 39:713–716 further explores the mechanism of action of riboflavin and other photosensitizers. However, no suggestion is made that such photosensitizers be used for decontamination of medical fluids.

Apparatuses for decontamination of blood have been described in U.S. Pat. No. 5,290,221 issued Mar. 1, 1994 to Wolfe, Jr., et al. and U.S. Pat. No. 5,536,238 issued Jul. 16, 1996 to Bischof. U.S. Pat. No. 5,290,221 discloses the irradiation of fluid in a relatively narrow, arcuate gap. U.S. Pat. No. 5,536,238 discloses devices utilizing optical fibers extending into a filtration medium. Both patents recommend as photosensitizers benzoporphryin derivatives which have an affinity for cell walls.

U.S. Pat. No. 5,527,704 issued Jun. 18, 1996 to Wolf, Jr., et al. discusses an apparatus to inactivate viruses contained in a body fluid in a container using methylene blue as a photosensitizer. The body fluid is maintained in a static state within the container during irradiation. U.S. Pat. No. 5,868,695 issued Feb. 9, 1999 to Wolf, Jr. et al. discloses a system where blood containing a photoactive material is directed in a predetermined flow path such as a serpentine in a narrow gap in a treatment chamber. PCT published application No. WO 96/06647 discloses irradiating a product in an array of light emitting diodes surrounded by a fluid used to prevent overheating of the diodes.

U.S. Pat. No. 5,360,734 issued Nov. 1, 1994 to Chapman et al. and U.S. Pat. No. 5,597,722 issued Jan. 28, 1997 to Chapman et al. discuss treating a blood component containing red blood cells and plasma proteins with a photoactive agent such as pyrrolic macrocycles, psoralens or methylene blue after removing a portion of the plasma proteins. The treated blood component is required to be prevented from contacting plasma proteins for a period of time (three to eighteen hours) after treatment to prevent bonding of the treated cells with IgG proteins in the plasma. The presence of IgG has various negative effects, including interference with commonly used serological and diagnostic testing procedures.

U.S. patent application Ser. No. 09/119,666 and continuation-in-part application Ser. No. 09/357,188, both hereby incorporated by reference to the extent not inconsistent with the disclosure herein, disclose the use of endogenous and endogenously-based photosensitizers including 7,8-dimethyl-10-ribityl isoalloxazine to inactivate microorganisms in a variety of fluids, including blood and blood products, but do not disclose removing plasma from the fluids.

U.S. patent application Ser. No. 09/420,652 hereby incorporated by reference to the extent not inconsistent with the disclosure herein, discloses isoalloxazine derivatives to neutralize microorganisms, but does not disclose removing plasma from the fluids.

BRIEF SUMMARY OF THE INVENTION

Methods and apparatuses are provided for treating a fluid to inactivate at least some of the microorganisms and/or white cells that may be present therein or thereon, said fluid containing one or more components selected from the group consisting of protein, (e.g. biologically active protein such as a therapeutic protein), blood and blood constituents. One such method comprises:

(a) adjusting the percentage of plasma in said fluid to a desired value;
(b) mixing an inactivation-effective, substantially non-toxic amount of an endogenous photosensitizer or endogenously-based derivative photosensitizer with said fluid; and
(c) exposing said fluid to photoradiation of sufficient wavelength and energy to activate the photosensitizer, whereby said microorganisms are inactivated.

It has been discovered that reducing the level of plasma in the fluid enhances the microorganism inactivation using endogenous or endogenously-based derivative photosensitizers, requiring a lower level of photosensitizer to achieve the same level of microorganism inactivation, reducing the time required for a desired level of inactivation, reducing the light dose required for a desired level of inactivation, and reducing the need for ultraviolet light to achieve a desired level of inactivation.

The adjusting step may be any method useful to adjust the amount of plasma present in a sample, or any method useful to reduce the amount of a particular component of plasma in a sample. One method suitable for the adjusting step is diluting the fluid with a diluting solution. This will reduce the level of all plasma constituents. The diluting solution used to bring the level of plasma to a desired value may be one of many different solutions, including saline; a buffer, which may comprise a variety of different substances; a solution containing glucose, phosphate or both, which may or may not act as a buffer; a solution containing nutrients for a component of the sample; a cryopreservative; an anticoagulant; a cell storage solution known to the art or developed to provide cells with suitable additives to enable them to be stored or infused; or other suitable solution. The solution should not substantially interfere with the inactivation of microorganisms or substantially destroy the biological activity of the fluid. As long as any interference the solution has with the inactivation process is not so great as to prevent inactivation from occurring at a desired level, the solution does not "substantially interfere." As long as the fluid is useful for its intended or natural purpose, the solution does not "substantially destroy" the biological activity. Selected proteins in plasma may be reduced selectively by proper selection of reagents and filtration. Such reagents and methods of filtering are known in the art. One such filter is a hollow fiber filter. The adjusting step may also be carried out using a mechanical means such as by centrifuging the fluid to separate the components, collecting the desired component or components and resuspending the desired component or components in a suitable solution. The process may be carried out more than once, to achieve the desired level of plasma adjustment. The process may also be carried out using gravity to separate the components. The adjusting step may also comprise washing the fluid one or more times, as known in the art. Washing is generally adding a solution to reduce the level of plasma in extracellular space between the cells. The fluid may be washed with a detergent solution or saline, for example.

In one embodiment of the invention, the amount of one component of plasma, for example, bilirubin or albumin, may be reduced selectively. The amount of bilirubin in a sample may be reduced by filtration through resin cartridges or washing or pre-irradiation with 447 nm light to break down the bilirubin, or any other method known to the art. Alternatively, the amount of the total plasma in the sample may be reduced. Both of these embodiments are intended to be encompassed by terms such as "reducing the percentage of plasma" and the like.

The mixing step may occur before, after or simultaneously with the adjusting step.

The photosensitizer may be a photo-activatable compound whose photolytic products (if any) are of low or no toxicity to humans or animals. The most preferred photosensitizer is 7,8-dimethyl-10-ribityl isoalloxazine.

The percentage of plasma in the fluid in the methods of the invention may be adjusted to any desired level that provides the effect of measurably improving the inactivation of microorganisms as compared to a fluid of the same composition if the percentage of plasma had not been reduced. Improving the inactivation of microorganisms means the light dose required for a desired level of inactivation is lower, the wavelength range of light required to inactivate a desired number of microorganism is narrower, the level of photosensitizer required is lower, the time required for a desired level of microorganism inactivation is shorter than required in a fluid of the same composition if the percentage of plasma had not been reduced, or a combination of these effects.

Photoradiation may comprise light in the visible spectrum, the ultraviolet spectrum, or light in both the visible and ultraviolet spectra. Any suitable wavelength or wavelengths of light may be used in any proportion and energy that produces the desired level of inactivation of microorganisms. For example, about half the light may be in the visible spectrum and about half the light may be in the ultraviolet spectrum. Alternatively, about one third of light may be in one spectral range and the other two thirds of light in the other spectral range. In one embodiment of the invention, two light sources (or two arrays of light sources) are used, to provide two wavelengths of light. As used herein, "wavelength" does not necessarily mean one discrete wavelength. Wavelength may comprise a range of about ±100 nm centered around one wavelength. Preferably, if ultraviolet light is used, the amount of ultraviolet light is kept to a level that minimizes damage to desired fluid components. Generally, this is provided by using 50% or less ultraviolet light relative to the total light energy delivered.

The fluid containing the photosensitizer is exposed to photoradiation of the appropriate wavelength to activate the photosensitizer, using an amount of photoradiation sufficient to activate the photosensitizer as described herein, but less than that which would cause non-specific damage to the biological components or substantially interfere with biological activity of other proteins present in the fluid. The wavelength used will depend on the photosensitizer selected and composition of the fluid, as is known to the art or readily determinable without undue experimentation following the teachings disclosed herein. Nonspecific damage is damage that damages all components.

The photoradiation in both the ultraviolet and visible spectra may be supplied concurrently or sequentially, with the visible portion preferably being supplied first. The photoradiation source may be a simple lamp or may consist of multiple lamps radiating at differing wavelengths. The photoradiation source should be capable of delivering a sufficient amount of light to activate the photosensitizer, preferably from about 100 to at least about 200 J/cm$^2$.

Also provided is an apparatus for inactivating microorganisms which may be present in a fluid with an endogenous or endogenously-based derivative photosensitizer, comprising:
  (a) a source of light that emits light of a suitable wavelength and intensity to activate the endogenous or endogenously-based derivative photosensitizer;
  (b) means for maintaining the fluid and an effective amount of an endogenous or endogenously-based derivative photosensitizer in the light path for a sufficient time to achieve the desired level of inactivation.

The means for maintaining the fluid and an effective amount of an endogenous or endogenously-based derivative photosensitizer in the light path may comprise a support surface substantially parallel to said source of light; a cuvette and flow-through system; or other means known in the art.

Also provided is a system for treating a fluid to inactivate microorganisms which may be present therein with an endogenous or endogenously based derivative photosensitizer comprising:
  (a) a container comprising said fluid having a desired level of plasma, at least an effective amount of an endogenous photosensitizer or endogenously-based derivative photosensitizer, and optionally one or more additives, said container having a photopermeable surface sufficient to allow exposure of the fluid therein to an amount of photoradiation sufficient to activate the photo sensitizer;
  (b) at least one photoradiation source in light communication with said container, said source capable of generating a suitable wavelength and intensity to activate the endogenous photosensitizer or endogenously-based derivative photosensitizer whereby microorganisms present are inactivated.

Also provided is a system for inactivation of microorganisms in a fluid containing such microorganisms comprising:
  (a) means for adjusting the plasma content of said fluid;
  (b) means for mixing an effective amount of an endogenous photosensitizer or endogenously-based derivative photosensitizer with said fluid;

(c) a photopermeable container for said fluid in fluid communication with said means for adding photosensitizer and said means for adjusting the plasma content having a depth and length selected to allow exposure of the fluid of step (b) therein to an amount of photoradiation sufficient to activate the photosensitizer at a selected flow rate;

(d) means for producing said selected flow rate of said fluid through said container; and (e) at least one photoradiation source for providing sufficient photoradiation to the fluid in said container of a type and amount selected to activate the photosensitizer.

Also provided is a system for treating a fluid to inactivate microorganisms which may be present therein comprising:

(a) means for adjusting the percentage of plasma in said fluid;

(b) a photosensitizer in powdered form;

(c) a photopermeable container for containing said fluid and photosensitizer;

(d) means for agitating said container;

(e) at least one photoradiation source in light communication with said container, said source capable of providing sufficient photoradiation to the fluid in said container of a type and amount selected to activate the photosensitizer whereby microorganisms are inactivated.

The photopermeable container may be a transparent plastic bag, a transparent plastic container with rigid walls, or other containers as known to the art. The agitation may be provided by a shaker table, or other means for agitating known to the art.

Also provided is a method for collecting a fluid with reduced levels of microorganisms that may be present therein, said fluid containing one or more members of the group consisting of: blood and blood components, comprising:

(a) placing said fluid in a photopermeable container;

(b) adding an endogenous or endogenously-based derivative photoactive material;

(c) adjusting the level of plasma in the blood or blood component to a desired level;

(d) exposing said fluid to radiation of a sufficient wavelength and intensity to inactivate microorganisms which may be present in said blood or blood component.

Also provided is an apparatus for collecting a fluid with reduced levels of microorganisms that may be present therein, said fluid containing one or more members of the group consisting of: blood and blood components, comprising:

(a) a photopermeable container containing an endogenous or endogenously-based derivative photoactive material and a suitable volume of a solution for adjusting the level of plasma in the blood or blood component to a desired level;

(b) a light source that emits light of a suitable wavelength and intensity to inactivate microorganisms which may be present in said fluid.

As used herein, the term "inactivation of a microorganism" means totally or partially preventing the microorganism from replicating, either by killing the microorganism or otherwise interfering with its ability to reproduce.

Microorganisms include viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include $\Phi$X174, $\Phi$6, $\lambda$, R17, $T_4$, and $T_2$. Exemplary bacteria include *P. aeruginosa, S. aureus, S. epidermis, L. monocytogenes, E. coli, K. pneumonia* and *S. marcescens*.

Inactivation of white blood cells may be desirable when suppression of immune or autoimmune response is desired, e.g., in processes involving transfusion of red cells, platelets or plasma when donor white blood cells may be present. The process disclosed may be used to inactivate white blood cells.

Materials which may be treated by the methods of this invention include any materials which are adequately permeable to photoradiation to provide sufficient light to achieve microorganism inactivation, or which can be suspended or dissolved in fluids which have such permeability to photoradiation. Examples of such materials are whole blood and aqueous compositions containing biologically active proteins derived from blood or blood constituents. Packed red cells, platelets and plasma (fresh or fresh frozen plasma) are exemplary of such blood constituents. In addition, therapeutic protein compositions containing proteins derived from blood, such as fluids containing biologically active protein useful in the treatment of medical disorders, e.g. factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. The activity of a biologically-active protein in said fluid is at a biologically-active level after said exposing step. A therapeutic protein present in said fluid remains able to perform a therapeutic function after the exposing step. Other fluids which could benefit from the treatment of this invention are peritoneal solutions used for peritoneal dialysis which are sometimes contaminated during connection, leading to peritoneal infections.

The term "biologically active" means capable of effecting a change in a living organism or component thereof. "Biologically active" with respect to "biologically active protein" as referred to herein does not refer to proteins which are part of the microorganisms being inactivated. Similarly, "non-toxic" with respect to the photosensitizers means low or no toxicity to humans and other mammals, and does not mean non-toxic to the microorganisms being inactivated. "Substantial destruction" of biological activity means at least as much destruction as is caused by porphyrin and porphyrin derivatives, metabolites and precursors which are known to have a damaging effect on biologically active proteins and cells of humans and mammals. Similarly, "substantially non-toxic" means less toxic than porphyrin, porphyrin derivatives, metabolites and precursors that are known for blood sterilization.

The term "blood product" as used herein includes blood constituents and therapeutic protein compositions containing proteins derived from blood as defined above. Fluids containing biologically active proteins other than those derived from blood may also be treated by the methods of this invention.

Decontamination methods of this invention using endogenous photosensitizers and endogenously-based photosensitizer derivatives do not substantially destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid. So long as fluid components retain sufficient biological activity to be useful for their intended or natural purposes, their biological activities are not considered to be "substantially destroyed."

Photosensitizers are known to be useful for inactivating microorganisms. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect.

Non-endogenous photosensitizers based on endogenous structures, such as those described in U.S. patent application Ser. No. 09/420,652 are also included. These non-endogenous photosensitizers and endogenously-based derivative photosensitizers are referred to herein as endogenously-based derivative photosensitizers.

As used herein, "powder" means dried medium, including powder or pill. When a dried medium of a substance is described herein, it is also intended that a solution or suspension of the powder in a suitable solvent may be used, and vice versa.

The method of this invention requires mixing the photosensitizer with the material to be decontaminated. "Adding" is intended to include mixing the fluid with the photosensitizer. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate microorganisms therein, but less than a toxic (to humans or other mammals) or insoluble amount. Excess photosensitizer may be used as long as the concentration is not so high that the photosensitizer prevents light from passing to the desired depth at a useful intensity. As taught herein, optimal concentrations for desired photosensitizers may be readily determined by those skilled in the art without undue experimentation. Preferably the photosensitizer is used in a concentration of at least about 1 micromolar. The optimum concentration of photosensitizer will vary depending on the blood component being treated and the level to which plasma is removed. If red blood cells are being treated, a higher concentration of photosensitizer is desired than if plasma or platelets are being treated. If red blood cells are being treated with riboflavin, a useful concentration of riboflavin is about 1–200 micromolar, and a preferred concentration of riboflavin is about 50 to 150 micromolar when the plasma content is about 0 to 5% of the total volume of the solution. If plasma or platelets are being treated, a useful concentration of riboflavin is about 1–100 micromolar, and a preferred concentration of riboflavin is about 10 to 30 micromolar when the plasma content is about 10–90% of the total volume of the solution.

The activated photosensitizer is capable of inactivating the microorganisms present, such as by interfering to prevent their replication. Specificity of action of the photosensitizer is conferred by the close proximity of the photosensitizer to the nucleic acid of the microorganism and this may result from binding of the photosensitizer to the nucleic acid. "Nucleic acid" includes ribonucleic acid (RNA) and deoxyribonucleic acid (DNA). Other photosensitizers may act by binding to cell membranes or by other mechanisms. The photosensitizer may also be targeted to the microorganism to be inactivated by covalently coupling to an antibody, preferably a specific monoclonal antibody to the microorganism.

The fluid containing the photosensitizer may be flowed into a photopermeable container for irradiation. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ Spectra™ and apheresis systems of GAMBRO, Inc., have been used to exemplify another embodiment involving batch-wise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosensitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings herein, and together with the flow rate of fluid through the container, the intensity of the photoradiation and the absorptivities of the fluid components, e.g., plasma, platelets, red blood cells, will determine the amount of time the fluid needs to be exposed to photoradiation.

In another embodiment involving batch-wise treatment, the fluid to be treated is placed in a photopermeable container which is agitated and exposed to photoradiation for a time sufficient to substantially inactivate the microorganisms. The photopermeable container is preferably a blood bag made of transparent or semitransparent plastic, and the agitating means is preferably a shaker table. The photopermeable container may be any other container, such as a rigid plastic container. The photosensitizer may be added to the container in powdered or liquid form and the container agitated to mix the photosensitizer with the fluid and to adequately expose all the fluid to the photoradiation to ensure inactivation of microorganisms.

Photosensitizer may be added to or flowed into the photopermeable container separately from the fluid being treated or may be added to the fluid prior to placing the fluid in the container. In one embodiment, photosensitizer is added to anticoagulant and the mixture of photosensitizer and anticoagulant are added to the fluid.

After treatment, the blood or blood product may be delivered to a patient, concentrated, or infused directly.

Enhancers may also be added to the fluid to make the process more efficient and selective. Such enhancers include antioxidants or other agents to prevent damage to desired fluid components or to improve the rate of inactivation of microorganisms and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof. These enhancers may be added in dried medium, including powder or pill form or in the form of liquids.

This invention also comprises fluids comprising biologically active protein, blood or blood constituents and also containing endogenous photosensitizer, endogenously-based derivative photosensitizer, or photoproduct thereof made by the inactivation methods described herein. The fluid may also contain inactivated microorganisms.

In addition to decontamination of whole blood, fluids containing blood products and biologically active proteins, this method is useful for treating other fluids including fluids which are meant for nourishment of humans or animals such as water, fruit, juices, milk, broths, soups and the like. The method is also useful for treating peritoneal or parenteral solutions.

In decontamination systems of this invention, the photoradiation source may be connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., especially when the amount of fluid exposed to the light is small, which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Cooling mechanisms include flow of air or fluid, as well as other mechanisms known to the art. Preferably, the temperature is kept between about 0° C. and about 45° C., more preferably between about 22° C. and about 45° C., and preferably about 40° C., depending on the composition of the fluid.

Any means for adding the photosensitizer to the fluid to be decontaminated and for placing the fluid in the photopermeable container known to the art may be used, such means typically including flow conduits, ports, reservoirs, sterile docking, valves, and the like. The system may include means such as pumps or adjustable valves for controlling the flow of the photosensitizer into the fluid to be decontaminated so that its concentration may be controlled at effective levels as described herein. In one embodiment, photosensitizer is mixed with the anticoagulant feed to a blood apheresis system. For endogenous photosensitizers and derivatives having sugar moieties, the pH of the solution is preferably kept low enough, as is known to the art, to prevent detachment of the sugar moiety. Preferably the photosensitizer is added to the fluid to be decontaminated in a pre-mixed aqueous solution, e.g., in water or storage buffer solution.

The photosensitizer and any optional desired additives may be placed in a container as dried medium, including powder or pill form, or as a solution. Desired additives include nutrients or other materials such as acetate, glucose, dextrose, citrate, pyruvate, which allow the components to retain biological activity or improve the storage lifetime. It may be desirable for platelets to be provided nutrients when the plasma concentration is less than about 20% of the total volume of the sample in order for the platelets to remain active. Desired additives and the photosensitizer may be sterilized as powders. In one embodiment, the powders desired are placed in the container prior to introduction of the fluid.

If the photosensitizer and any desired additives are placed in the container as one or more solutions, the volume and composition of the solution(s) may produce the desired percentage of plasma in the sample, without further additions of solution, or the percentage of plasma may be adjusted before, during or after placing said fluid in said container. Adjustment of the percentage of plasma after placing the fluid in the container may occur by the introduction of a suitable solution after the fluid is in the container. Adjustment of the percentage of plasma may occur during introduction of the fluid in a container by the introduction of a suitable solution as the fluid is being placed in the container.

The photopermeable container for the flow-through system may be a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

In another embodiment the fluid is placed in a photopermeable container such as a blood bag, e.g. used with the apheresis system described in U.S. Pat. No. 5,653,887, and agitated while exposing to photoradiation. Suitable bags include collection bags as described herein. Collection bags used in the Spectra™ system or Trima™ apheresis system of GAMBRO Inc. are especially suitable. Shaker tables are known to the art, e.g. as described in U.S. Pat. No. 4,880,788. The bag is equipped with at least one port or opening for adding fluid thereto. In one embodiment the photosensitizer, preferably 7,8-dimethyl-10-ribityl-isoalloxazine, is added to the fluid-filled bag as dried medium, including powder or pill form. The bag is then placed on a shaker table and agitated under photoradiation until substantially all the fluid has been exposed to the photoradiation. Alternatively, the bag may be prepackaged with the powdered photosensitizer contained therein. The fluid to be decontaminated may then be added through the appropriate port.

Decontamination systems as described above may be designed as stand-alone units or may be easily incorporated into existing apparatuses known to the art for separating or treating blood being withdrawn from or administered to a patient. For example, such blood-handling apparatuses include the GAMBRO Spectra™ or TRIMA® apheresis systems, available from GAMBRO Inc., Lakewood, Colo., or the apparatuses described in U.S. Pat. No. 5,653,887 and U.S. Ser. No. 08/924,519 filed Sep. 5, 1997 (PCT Publication No. WO 99/11305) of GAMBRO, Inc. as well as the apheresis systems of other manufacturers. The decontamination system may be inserted just downstream of the point where blood is withdrawn from a patient or donor, just prior to insertion of blood product into a patient, or at any point before or after separation of blood constituents. The plasma may be adjusted at any point before fluid is exposed to irradiation. The photosensitizer is added to blood components along with anticoagulant in a preferred embodiment, and separate irradiation sources and cuvettes are placed downstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In other embodiments, decontamination systems of this invention may be used to process previously collected and stored blood products.

When red blood cells are present in the fluid being treated, as will be appreciated by those skilled in the art, to compensate for absorption of light by the cells, the fluid may be thinned, exposed to higher energies of radiation for longer periods, agitated for longer periods or presented to photoradiation in shallower containers or conduits than necessary for use with other blood components.

The endogenous photosensitizers and endogenously-based derivative photosensitizers disclosed herein can be used in pre-existing blood component decontamination systems as well as in the decontamination system disclosed herein. For example, the endogenous photosensitizers and endogenously-based derivative photosensitizers of this invention can be used in the decontamination systems described in U.S. Pat. Nos. 5,290,221, 5,536,238, 5,290,221 and 5,536,238.

Platelet additive solutions comprising endogenous photosensitizers and endogenously-based derivative photosensitizers as described above are also provided herein. Platelet additive solutions known to the art may be used for this purpose and include those disclosed in U.S. Pat. Nos. 5,908,742; 5,482,828; 5,569,579; 5,236,716; 5,089,146; and 5,459,030. Such platelet additive solutions may contain physiological saline solution, buffer, preferably sodium phosphate, and other components including magnesium chloride and sodium gluconate. The pH of such solutions is preferably between about 7.0 and 7.4. These solutions are useful as carriers for platelet concentrates to allow maintenance of cell quality and metabolism during storage, reduce plasma content and extend storage life. The photosensitizer may be present in such solutions at any desired concentration from about 1 µM to the solubility of the photosensitizer in the solution, and preferably between about 10 µM and about 100 µM, more preferably about 10 µM. In a preferred embodiment, the platelet additive solution also comprises enhancers as described above. A preferred platelet additive solution comprises sodium acetate, sodium chloride, sodium gluconate, 1.5 micromolar magnesium chloride, 1 micromolar sodium phosphate 14 µM 7,8-dimethyl-10-ribityl-isoalloxazine and preferably also 6 micromolar ascorbate. These platelet additive solutions may be added in a desired volume to a fluid so that the level of plasma is at a desired level before irradiation, or platelet additive solutions may be used to resuspend a pellet. Other uses for platelet additive solutions are known to the art.

A photoradiation enhancer, such as a reflective surface may also be provided in any method or apparatus of the invention. The light may be guided to impinge on the fluid in any desired manner, including positioning the fluid in the light path of the light source, using a light guide, or other methods. The apparatuses of the invention may also comprise components such as a temperature monitor, temperature controller, means for flowing said fluid into and out of said container, means for agitating said fluid in said container, and other desired components to control various aspects of the system. The temperature controller may be a fan directed toward the light source, directed on the fluid, or both. One or more temperature controllers may be used to cool different components to different levels.

BRIEF DESCRIPTION OF THE FIGURES

FIG. 31 shows inactivation of BVDV in red blood cells with 35–40% hematocrit with 447 nm light at varying energies.

DETAILED DESCRIPTION OF THE INVENTION

The decontamination method of this invention using endogenous photosensitizers and endogenously-based derivative photosensitizers is exemplified herein using 7,8-dimethyl-10-ribityl isoalloxazine as the photosensitizer, however, any photosensitizer may be used which is capable of being activated by photoradiation to cause inactivation of microorganisms. The photosensitizer must be one which does not substantially destroy desired components of the fluid being decontaminated, and also preferably which does not break down as a result of the photoradiation into products which significantly destroy desired components or have significant toxicity. The wavelength at which the photosensitizer is activated is determined as described herein, using literature sources or direct measurement. Its solubility in the fluid to be decontaminated or in a combination of carrier fluid and fluid to be contaminated is also so determined. The ability of photoradiation at the activating wavelength to penetrate the fluid to be decontaminated must also be determined as taught herein. The desired level of plasma in the fluid is also determined as described herein. Appropriate temperatures for the reaction of the photosensitizer with its substrate are determined, as well as the ranges of temperature, photoradiation intensity and duration and photosensitizer concentration which will optimize microbial inactivation and minimize damage to desired proteins and/or cellular components in the fluid.

Figure 6:
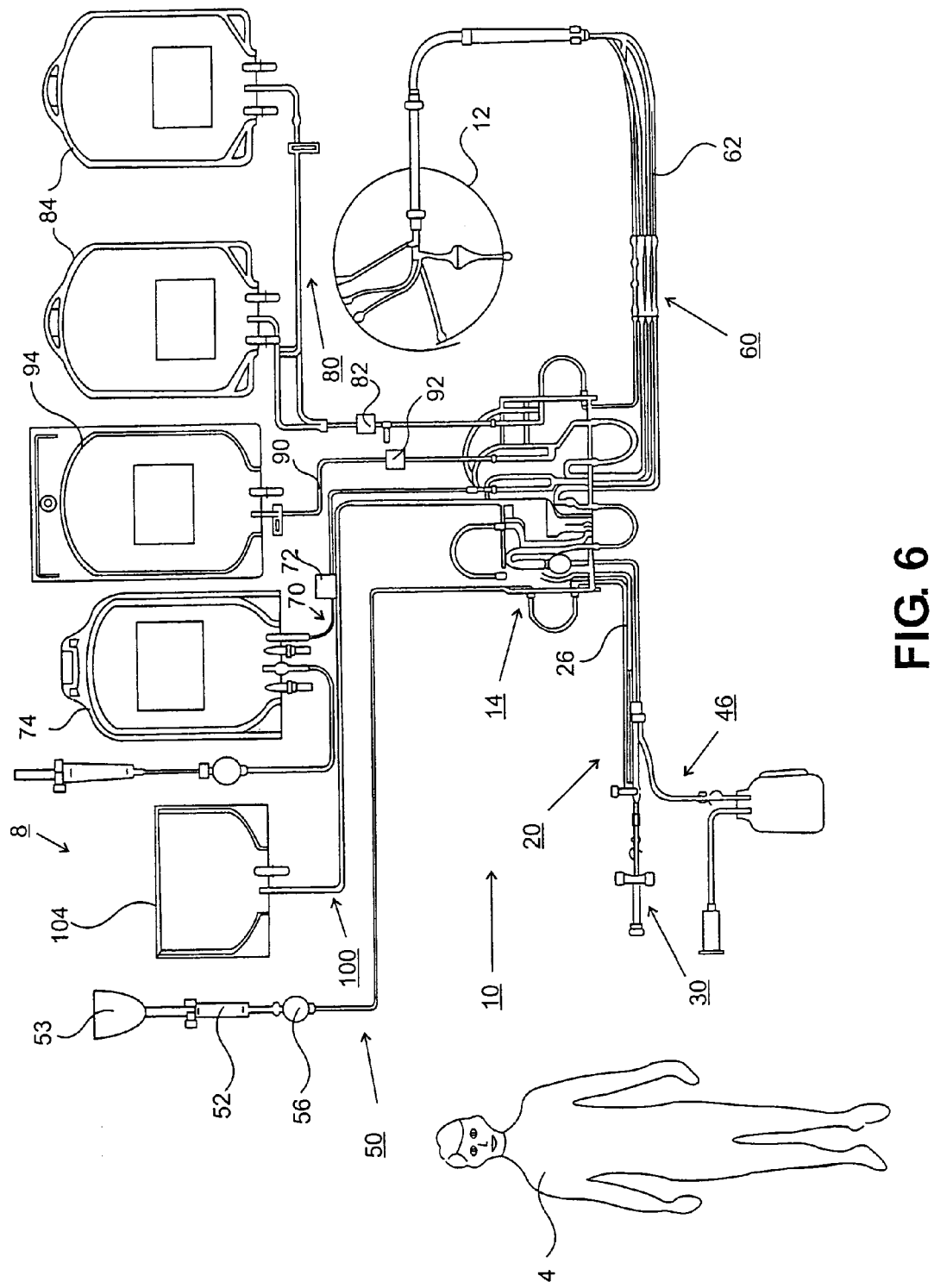
FIG. 6 depicts a blood separation apparatus incorporating the photoradiation device of this invention.
Figure 7:
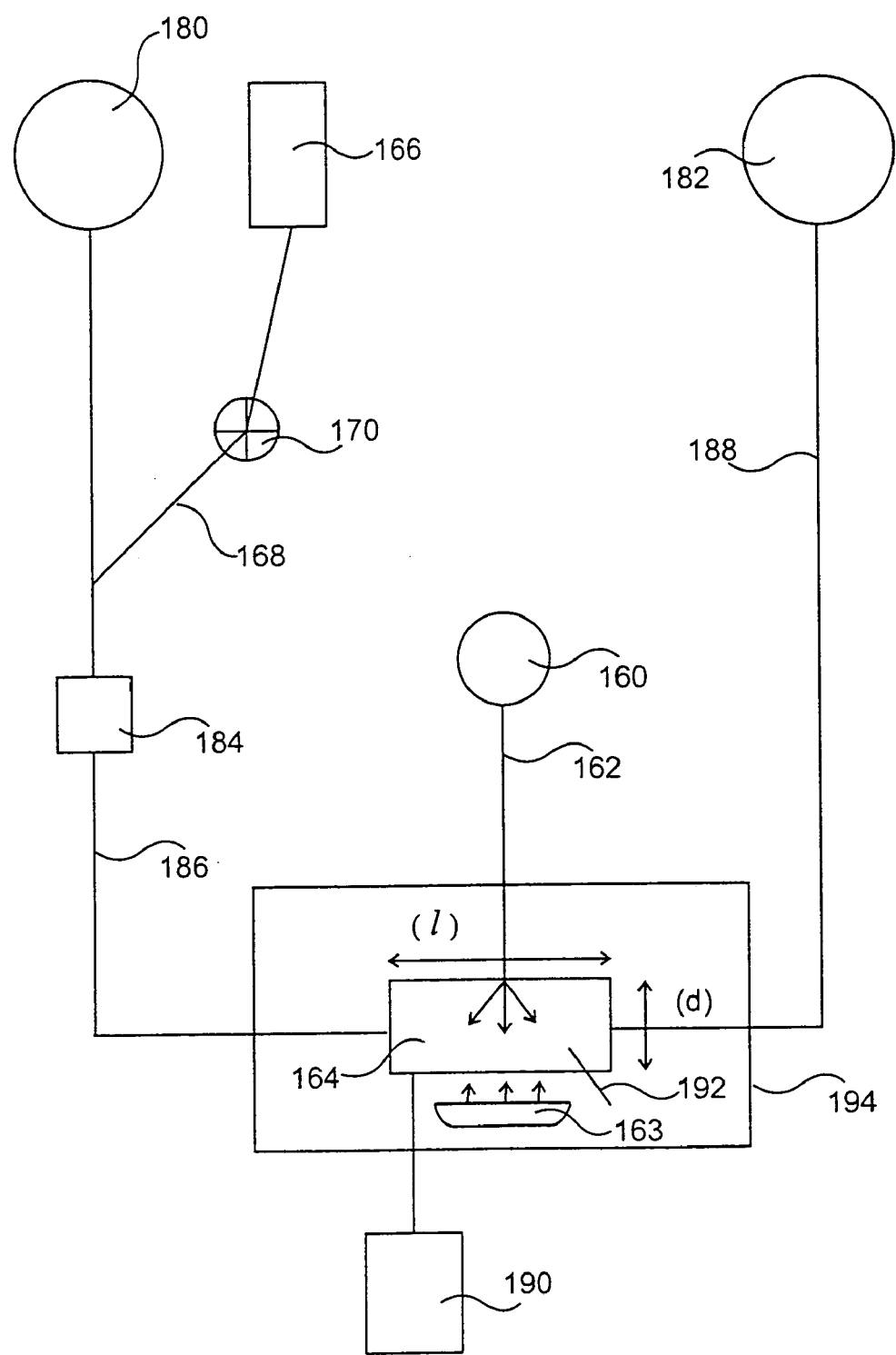
FIG. 7 depicts the decontamination assembly of this invention.

Once such system requirements have been determined for flow-through systems, apparatuses may be designed which provide the correct flow rates, photopermeabilities, plasma contents, light wavelengths and light intensities to cause inactivation of microorganisms present in the fluid, as is taught herein. In one embodiment, the plasma content of a fluid to be decontaminated is adjusted, the fluid is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopermeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature. FIG. 6 depicts a decontamination system of this invention as part of an apparatus for separating blood components, and FIG. 7 provides details of a preferred decontamination system.

For batch systems, it is preferred to place the fluid to be decontaminated along with photosensitizer in bags which are photopermeable or at least sufficiently photopermeable to allow sufficient radiation to reach their contents to activate the photosensitizer. Sufficient photosensitizer is added to each bag to provide inactivation, and the bag is preferably agitated while irradiating, for a period of time to ensure exposure of substantially all the fluid to radiation. The photosensitizer may be added in powdered form.

The method preferably uses endogenous photosensitizers, including endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate the effects of 7,8-dimethyl-10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8-dimethyl-10-ribityl isoalloxazine allows greater selectivity in its action than is the case with compounds such as psoralens which possess significant Type II chemistry.

7,8-dimethyl-10-ribityl isoalloxazine (Riboflavine or vitamin B2) absorbs light from about 200 to 500 nm. The ring system core of 7,8-dimethyl-10-ribityl isoalloxazine is resistant to photodegradation but the ribityl side chain of riboflavin undergoes photodegradation. Photolysis of 7,8-dimethyl-10-ribityl isoalloxazine may form lumichrome (7,8-dimethylalloxazine) depending on conditions. 7,8-dimethylalloxazine strongly absorbs ultraviolet (UV) light and only weakly absorbs visible light.

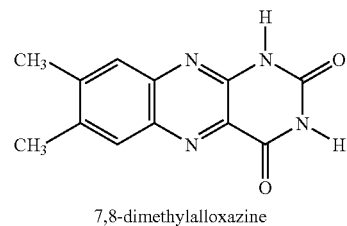

7,8-dimethylalloxazine

As a result of the degradation of 7,8-dimethyl-10-ribityl isoalloxazine upon exposure to light, a combination of visible and ultraviolet light is preferred in decontamination procedures using 7,8-dimethyl-10-ribityl isoalloxazine. Since UV light has a higher energy per photon than visible light, and because UV light is absorbed more strongly than visible light by useful compounds in the biological fluid, more damage to the useful components in the biological fluid containing the contaminants will occur when ultraviolet light is used in combination with visible light than when visible light can be used alone.

FIG. 6 shows a blood apparatus device and apheresis system incorporating the photoradiation devices of this invention. Whole blood is withdrawn from a donor/patient 4 and is provided to an apheresis system or blood component separation device 8 where the blood is separated into the various component types and at least one of these blood component types is removed from the device 8. These blood components may then be provided for subsequent use by another or may undergo a therapeutic treatment and be returned to the donor/patient 4.

In the blood component separation device 8, blood is withdrawn from the donor/patient 4 and directed through an extracorporeal tubing circuit 10 and a blood-processing vessel 12, defining a completely closed and sterile system. The blood component separation device 8 is connected to a pump (not shown). Blood flows from the donor/patient 4 through the extracorporeal tubing circuit 10 and into rotating blood processing vessel 12. The blood within the blood processing vessel 12 is separated into various blood component types, and these component types (platelets, plasma, red blood cells) are continually removed from the blood processing vessel 12. Blood components which are not being retained for collection or for therapeutic treatment (e.g., red blood cells, white blood cells, plasma) are also removed from the blood processing vessel 12 and returned to the donor/patient 4 via the extracorporeal tubing circuit 10.

Operation of the blood component separation device is preferably controlled by one or more computer processors included therein.

Extracorporeal tubing circuit 10 comprises a cassette assembly 14 and a number of tubing assemblies 20, 50, 60, 80, 90, 100 interconnected therewith. Blood removal/return tubing assembly 20 provides a single needle interface between a donor/patient 4 and cassette assembly 14, and blood inlet/blood component tubing subassembly 60 provides the interface between cassette assembly 14 and blood processing vessel 12. An anticoagulant tubing assembly 50, platelet collection tubing assembly 80, plasma collection tubing assembly 90, red blood cell collection tubing assembly 70 and vent bag tubing subassembly 100 are also interconnected with cassette assembly 14.

The blood removal/return tubing assembly 20 includes a needle subassembly 30 interconnected therewith and anticoagulant tubing 26 connecting to anticoagulant tubing assembly 50 through cassette assembly 14.

Cassette assembly 14 includes front and back molded plastic plates that are hot-welded together to define a rectangular cassette member having integral fluid passageways. The cassette assembly 14 further includes a number of outwardly extending tubing loops interconnecting various integral passageways. The integral passageways are also interconnected to the various tubing assemblies.

Specifically, cassette assembly 14 interconnects with anticoagulant tubing 26 of the blood removal/return tubing assembly 20 and with anticoagulant tubing assembly 50. The anticoagulant tubing assembly 50 includes a spike drip chamber 52 connectable to anticoagulant and photosensitizer source 53 and a sterilizing filter 56. During use, the anticoagulant tubing assembly 50 supplies anticoagulant mixed with photosensitizer to the blood removed from donor/patient 4 to reduce or prevent any clotting in the extracorporeal tubing circuit 10. Many anticoagulants are known to the art, e.g. as disclosed in Chapter 3 of the AABB Technical Manual, 11th edition, 1993, including ACD-A, CPD, CP2D, CPDA-1 and heparin. These as well as cell storage solutions, AS-1, AS-3 and AS-5, are all compatible with the endogenous photosensitizers and endogenously-based derivative photosensitizers described herein.

Cassette assembly 14 also includes an interconnection with blood removal tubing of the blood removal/return tubing assembly 20. Blood passes through pressure sensors, and an inlet filter in cassette assembly 14 and thence to blood inlet tubing 62. Blood inlet tubing 62 is also interconnected with blood processing vessel 12 to provide whole blood thereto for processing.

To return separated blood components to cassette assembly 14, the blood inlet/blood component tubing assembly 60 further includes red blood cell (RBC)/plasma outlet tubing, platelet outlet tubing and plasma outlet tubing interconnected with corresponding outlet ports on blood processing vessel 12. The red blood cell (RBC)/plasma outlet tubing channels the separated red blood cell (RBC)/plasma component through cassette assembly 14 to red blood cell collection tubing assembly 70 through first decontamination system 72. The platelet outlet tubing channels separated platelets through cassette assembly 14 to platelet collection tubing assembly 80 through second decontamination system 82. The plasma outlet tubing channels separated plasma through cassette assembly 14 to plasma collection tubing assembly 90 through third decontamination system 92. After irradiation in the decontamination systems 72, 82 and 92, to activate the photosensitizer and inactivate microorganisms present, the blood components are collected in red blood cell collection bag 74, platelet collection bags 84, and plasma collection bag 94. Vent bag 104 may be used to vent gases within the system. The plasma level of the fluids may be adjusted at any convenient point in the process.

FIG. 7 depicts a stand-alone version of the decontamination assembly of this invention. Blood product 180 (which may be recently collected blood or blood component or stored blood) is connected to blood product line 186 which leads through pump 184 to decontamination cuvette 164. Photo sensitizer reservoir 166 is connected to photosensitizer input line 168 equipped with input pump 170, and leads into blood product line 186 upstream from decontamination cuvette 164. Decontamination cuvette 164 is a photopermeable cuvette of a depth (d) and a length (l) selected to ensure decontamination. Cooling system 190 combined with temperature monitor 192 are connected with decontamination cuvette 164 for controlling the temperature of the fluid. Decontamination cuvette 164 is connected via light guide 162 to photoradiation source 160. A photoradiation enhancer 163 is placed adjacent to (either touching or spaced apart from) decontamination cuvette 164 to increase the amount of photoradiation reaching the blood product in the cuvette. Decontaminated blood product line 188 leads from decontamination cuvette 164 to decontaminated blood product collection 182.

In operation, blood product 180 is conducted into blood product line 186 where it is joined by photosensitizer from photosensitizer reservoir 166 flowing at a rate controlled by photosensitizer input pump 170 in photosensitizer input line 68 which joins blood product line 186. The flow rate in blood product line 186 is controlled by pump 184 to a rate selected to ensure decontamination in decontamination cuvette 164. Temperature monitor 192 measures the temperature of fluid in cuvette 164 and controls cooling system 190 which keeps the temperature in the cuvette within a range required for optimal operation. The blood product in decontamination cuvette 164 is irradiated by photoradiation from photoradiation source 160 conducted in light guide 162. The photoradiation source may comprise two or more actual lights. The arrows indicate photoradiation from the end of light guide 162 propagating in the blood product inside transparent decontamination cuvette 164. Adjacent to decontamination cuvette 164 is photoradiation enhancer 163 which may be an additional source of photoradiation or a reflective surface. The arrows from photoradiation enhancer 163 pointing toward decontamination cuvette 164 indicate photoradiation from photoradiation enhancer 163 shining on the blood product material in cuvette 164. Decontaminated blood product exits decontamination cuvette 164 via decontaminated blood product line 188 and is collected at decontaminated blood product collection 182.

In one embodiment using 7,8-dimethyl-10-ribityl isoalloxazine from Sigma Chemical Company as the photosensitizer, a light guide from EFOS Corporation, Williamsville, N.Y. composed of optical fibers is used. The system is capable of delivering a focused light beam with an intensity of 6,200 mW/cm$^2$ in the region of 355–380 nm. It is also possible to use interchangeable filters with the system to achieve outputs of 4,700 mW/cm$^2$ in the spectral region of 400–500 nm. In both cases, the output of light in the region of 320 nm and lower is negligible. Light guides of varying dimensions (3, 5 and 8 mm) are available with this system. The light exits the light guide tip with a 21 degree spread. The 8 mm light guide is appropriate, correctly placed, to adequately illuminate the face of the preferred decontamination cuvette which is a standard cuvette used on GAMBRO Spectra™ disposables sets from Industrial Plastics, Inc., Forest Grove, Oreg.

The flow rate is variable and is determined by the amount of light energy intended to be delivered to the sample. The flow rate is controlled by means of a peristaltic pump from the Cole-Parmer Instrument Company, Vernon Hills, Ill. Flow rates and type of input stream may be controlled via a computer processor as is known to the art.

Figure 23:
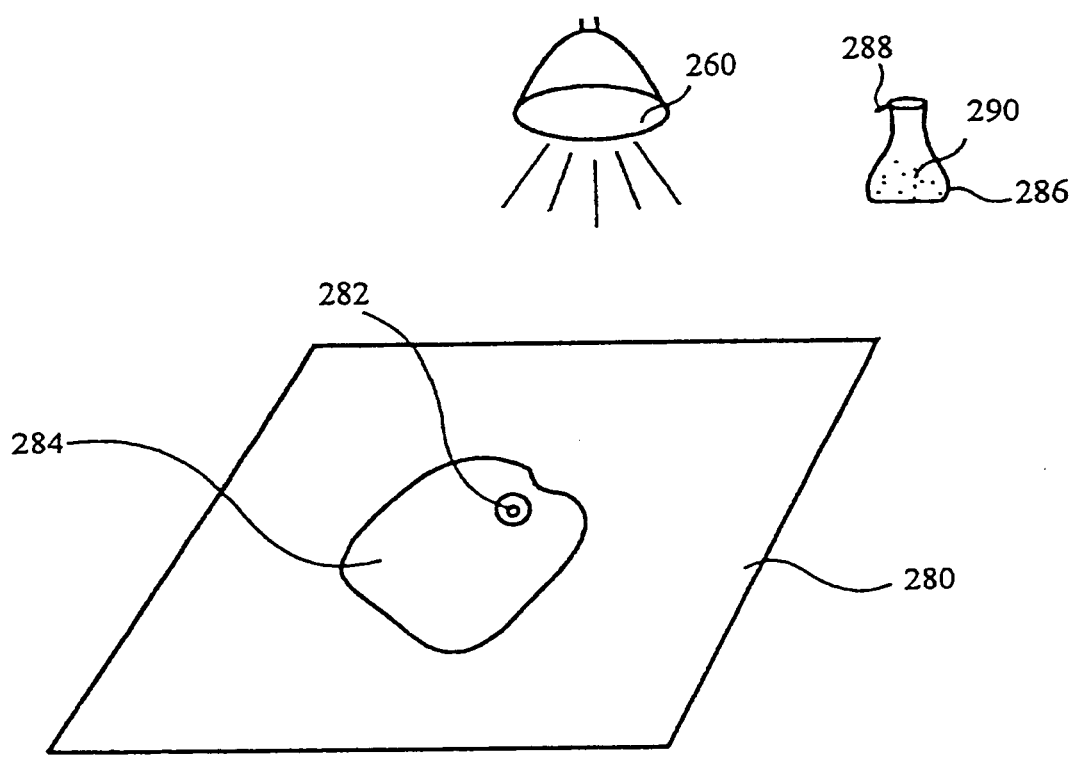
FIG. 23 shows an embodiment of this invention using a blood bag to contain the fluid being treated and photosensitizer and a shaker table to agitate the fluid while exposing to photoradiation from a light source.

FIG. 23 depicts an embodiment of this invention in which fluid to be decontaminated is placed in a blood bag 284 equipped with an inlet port 282, through which photosensitizer in powder or solution form 284 is added from flask 286 via pour spout 288. The fluid may have had the plasma reduced prior to inlet into the bag, the bag may contain appropriate dilution solutions, the appropriate diluting solutions may be added to the bag after the fluid has been added, or the level of plasma may be reduced by any other means. Shaker table 280 is activated to agitate the bag 284 to mix or dissolve photosensitizer 290 while photoradiation source 260 is activated to irradiate the fluid and photosensitizer in bag 284. Alternatively, the bag can be provided prepackaged to contain photosensitizer and any desired additives and the fluid is thereafter added to the bag.

The methods of this invention do not require the use of enhancers such as "quenchers" or oxygen scavengers, however these may be used to enhance the process by reducing the extent of non-specific cell or protein-damaging chemistry or enhancing the rate of pathogen inactivation. Further preferred methods using non-toxic endogenous photosensitizers and endogenously-based derivative photosensitizers do not require removal of photosensitizers from the fluid after photoradiation. Test results show little or no damage to other blood components, e.g. platelets remain biologically active five days post-treatment.

Effect of Lower Plasma Content on Microorganism Inactivation

Human blood platelets are typically stored at 20–24° C. under gentle agitation in a gas permeable plastic container. The platelets are typically suspended in autologous plasma which may be supplemented with various formulations of additive solutions which provide nutrients, buffers and essential salts. Under these conditions, platelets may be held for 5 days or more before transfusion to a patient. Over the course of this storage period, all platelets undergo a deterioration in their metabolic status (indicated by the use of fuels and oxygen, and accumulation of lactic acid), and deterioration of their functional capacity as indicated by the loss or response to agonists, release of storage vesicles, appearance of neo-activation antigens on the plasma membrane, loss of plasma membrane molecular receptors, loss of lipid asymmetry, and/or appearance or microparticles. Previous efforts to minimize the in vitro damage to platelets and maintain their full functional capacity over time have been: change in storage temperature from 4° C. to 22° C., use of storage containers with improved gas permeability for $O_2$ entry and $CO_2$ egress, exogenous fuel sources such as activation signal pathways with chemicals such as $PGE_1$ and cytochalasin, and light crosslinking of the cell with fixatives such as paraformaldehyde.

Lower plasma content in the microorganism inactivation methods of the invention improves the kinetics of microorganism inactivation and the cell quality because, for example, the time of irradiation and the light dose applied is reduced, and the need for ultraviolet light is reduced. Blood or blood components having lowered plasma content treated by the methods of this invention also have a enhanced storage time over blood or blood components that do not have lower plasma content.

In deactivation processes using photoactivated riboflavin, it has been determined that a large percent, typically about forty percent of riboflavin added to whole blood binds to plasma. This results in less riboflavin available to perform inactivation functions. Addition of more riboflavin to the sample does not provide more available riboflavin in a linear manner, due to at least two competing effects. First, the binding sites on the plasma cannot be saturated in whole blood and second, internal quenching of riboflavin occurs. Internal quenching occurs when the free riboflavin concentration causes an increase in the optical density of the solution.

With high protein concentrations, visible light activation of riboflavin yields a constant but relatively low level of inactivation of microorganisms. Addition of more visible light does not produce any additional inactivation because the riboflavin has been converted to lumichrome, which does not absorb visible light. Addition of ultraviolet light will produce additional inactivation, due to activation of lumichrome. However, as described elsewhere, ultraviolet light damages mitochondria and cell membranes. If the plasma content of a solution is decreased, visible light activation alone will produce a large inactivation without the use of ultraviolet light.

The preferred parameters for inactivating microorganisms in fluids including wavelength of activation, light dose, photosensitizer concentration and plasma percentage vary depending on the composition of the fluid being treated. Methods for optimizing these parameters for a given fluid composition are given herein, or known to those of ordinary skill in the art without undue experimentation.

To inactivate microorganisms in red blood cells with riboflavin as the photosensitizer, it is preferred that a wavelength range of between about 420 and about 500 nm is used. The most preferred wavelength is about 470 nm. Riboflavin in a concentration range of between about 50 and about 150 micromolar is preferred, with a concentration of about 100 micromolar most preferred for the preferred plasma content. A plasma content of between about 0 and about 50 percent of the total volume of the fluid is preferred, with a plasma content less than 20 percent by volume more preferred, with a plasma content less than about 10 percent of the total volume of the fluid being most preferred. The use of a storage and dilution solution such as CPD (Fenwal Labs, Deerfield, Ill.) or AS-1,2,3 (Fenwal Labs, Deerfield, Ill.) is preferred. A light intensity range of between about 40 and 100 mW/cm$^2$ of visible light is preferred, with as high a light intensity as possible being most preferred. 100 to 500 J/cm$^2$ of light is preferred, with 50 to 200 J/cm$^2$ being most preferred. A sufficient level of additives may be added to the fluid so that one or more components present in said fluid remain biologically active after exposing the fluid to photoradiation. The components of various diluting solutions and additive solutions are shown in the following tables.

|  | Molecular Weight | PAS II | | PSM1-pH | | PlasmaLyte A | |
|---|---|---|---|---|---|---|---|
|  |  | Concentration (mMol/L) | g/300 mLs | Concentration (mMol/L) | g300 mLs | Concentration (mMol/L) | g/300 mLs |
| Sodium Chloride | 58.44 | 115.5 | 2.02 | 98 | 1.72 | 90 | 1.58 |
| Potassium Chloride | 74.55 |  | 0.00 | 5 | 0.11 | 5 | 0.11 |
| Calcium Chloride | 111 |  | 0.00 |  | 0.00 |  | 0.00 |
| Magnesium Chloride | 95.21 |  | 0.00 |  | 0.00 | 3 | 0.09 |
| Magnesium Sulfate | 120.4 |  | 0.00 |  | 0.00 |  | 0.00 |

-continued

| | | | | | | | |
|---|---|---|---|---|---|---|---|
| Tri-Sodium Citrate | 294.1 | 10 | 0.88 | 23 | 2.03 | 23 | 2.03 |
| Citric Acid | 192.1 | | 0.00 | | 0.00 | | 0.00 |
| Sodium Bicarbonate | 84.01 | | 0.00 | | 0.00 | | 0.00 |
| Sodium Phosphate | 142 | | 0.00 | 25 | 1.07 | | 0.00 |
| Sodium Acetate | 82.03 | 30 | 0.74 | | 0.00 | 27 | 0.66 |
| Sodium Gluconate | 218.1 | | 0.00 | | 0.00 | 23 | 1.50 |
| Glucose | 180.2 | | 0.00 | | 0.00 | | 0.00 |
| Maltose | 360.3 | | 0.00 | | 0.00 | | 0.00 |
| Total Mass (grams) | | | 3.65 | | 4.92 | | 5.97 |

| | | SetoSol | | PAS III | | PAS | |
|---|---|---|---|---|---|---|---|
| | Molecular Weight | Concentration (mMol/L) | g/300 mLs | Concentration (mMol/L) | g/300 mLs | Concentration (mMol/L) | g/300 mLs |
| Sodium Chloride | 58.44 | 90 | 1.58 | 77 | 1.35 | 110 | 1.93 |
| Potassium Chloride | 74.55 | 5 | 0.11 | | 0.00 | 5.1 | 0.11 |
| Calcium Chloride | 111 | | 0.00 | | 0.00 | 1.7 | 0.06 |
| Magnesium Chloride | 95.21 | 3 | 0.09 | | 0.00 | | 0.00 |
| Magnesium Sulfate | 120.4 | | 0.00 | | 0.00 | 0.8 | 0.03 |
| Tri-Sodium Citrate | 294.1 | 17 | 1.50 | 12.3 | 1.09 | 15.2 | 1.34 |
| Citric Acid | 192.1 | | 0.00 | | 0.00 | 2.7 | 0.16 |
| Sodium Bicarbonate | 84.01 | | 0.00 | | 0.00 | 35 | 0.88 |
| Sodium Phosphate | 142 | 25 | 1.07 | 28 | 1.19 | 2.1 | 0.09 |
| Sodium Acetate | 82.03 | 23 | 0.57 | 42 | 1.03 | | 0.00 |
| Sodium Gluconate | 218.1 | | 0.00 | | 0.00 | | 0.00 |
| Glucose | 180.2 | 23.5 | 1.27 | | 0.00 | 38.5 | 2.08 |
| Maltose | 360.3 | 28.8 | 3.11 | | 0.00 | | 0.00 |
| Total Mass (grams) | | | 9.29 | | 4.66 | | 6.68 |

Note: Assumes that all salts are anhydrous

Anticoagulant Preservative Solutions

| | | CPD | | | CP2D | | | CPDA-1 | | |
|---|---|---|---|---|---|---|---|---|---|---|
| | Molecular Weight | Conc. (mMol/L) | mg/63 ml | mg/100 ml | Conc. (mMol/L) | mg/63 ml | mg/100 ml | Conc. (mMol/L) | mg/63 ml | mg/100 ml |
| Sodium Citrate | 294.1 | 89.59 | 1660.00 | 2634.92 | 89.59 | 1660.00 | 2634.92 | 89.59 | 1660.00 | 2634.92 |
| Citric Acid | 192.1 | 15.53 | 188.00 | 298.41 | 15.53 | 188.00 | 298.41 | 15.53 | 188.00 | 298.41 |
| Dextrose | 180.2 | 141.82 | 1610.00 | 2555.56 | 283.64 | 3220.00 | 5111.11 | 177.05 | 2010.00 | 3190.48 |
| Monobasic Sodium phosphate | 120 | 18.52 | 140.00 | 222.22 | 18.52 | 140.00 | 222.22 | 18.52 | 140.00 | 222.22 |
| Adenine | 135.1 | 0.00 | 0.00 | 0/00 | 0.00 | 0.00 | 0.00 | 2.03 | 17.30 | 27.46 |
| Total Mass (grams) | | | 3.60 | 5.71 | | 5.21 | 8.27 | | 4.02 | 6.37 |

Additive Solutions

| | | AS-1 (Adsol) | | AS-3 (Nutricel) | | AS-5 (Optisol) | | SAGM | | MAP | |
|---|---|---|---|---|---|---|---|---|---|---|---|
| | Molecular Weight | Conc. (mMol/L) | mg/100 ml | Conc. (mMol/L) | MG/100 ml | Conc. (mMol/L) | mg/100 ml | Conc. (mMol/L) | mg/100 ml | Conc. (mMol/L) | mg/100 ml |
| Dextrose | 180.2 | 122.09 | 2200.00 | 61.04 | 1100.00 | 49.94 | 900.0 | 49.94 | 900.00 | 0.00 | 0.00 |
| Adenine | 135.1 | 2.00 | 27.00 | 2.22 | 30.00 | 2.22 | 30.00 | 1.25 | 16.90 | 0.10 | 1.30 |
| Monobasic Sodium phosphate | 120 | 0.00 | 0.00 | 23.00 | 276.00 | 0.00 | 0.00 | 0.00 | 0.00 | 7.80 | 93.60 |
| Mannitol | 182.2 | 41.16 | 750.00 | 0.00 | 0.00 | 28.81 | 525.00 | 28.81 | 525.00 | 79.91 | 1456.00 |
| Sodium Chloride | 58.45 | 153.98 | 900.00 | 70.15 | 410.00 | 150.04 | 877.00 | 150.04 | 877.00 | 85.03 | 497.00 |
| Sodium Citrate | 294.1 | 0.00 | 0.00 | 19.99 | 588.00 | 0.00 | 0.00 | 0.00 | 0.00 | 6.00 | 176.40 |
| Glucose | 180.2 | 0.00 | 0.00 | 0.00 | 0.00 | 0.00 | 0.00 | 0.00 | 0.00 | 39.96 | 720.00 |

-continued

| | | Additive Solutions | | | | | | | | |
|---|---|---|---|---|---|---|---|---|---|---|
| | | AS-1 (Adsol) | | AS-3 (Nutricel) | | AS-5 (Optisol) | | SAGM | | MAP |
| | Molecular Weight | Conc. (mMol/L) | mg/100 ml | Conc. (mMol/L) | MG/100 ml | Conc. (mMol/L) | mg/100 ml | Conc. (mMol/L) | mg/100 ml | Conc. (mMol/L) | mg/100 ml |
| Citric Acid | 192.1 | 0.00 | 0.00 | 2.19 | 42.00 | 0.00 | 0.00 | 0.00 | 0.00 | 0.00 | 0.00 |
| Total Mass (grams) | | | 3.88 | | 2.45 | | 2.33 | | 2.32 | | 2.94 |

| | | Anticoagulants for Apheresis | | | |
|---|---|---|---|---|---|
| | | ACD-A | | ACD-B | |
| | Molecular Weight | Conc. (mMol/L) | mg/100 ml | Conc. (mMol/L) | mg/100 ml |
| Dextrose | 180.2 | 135.96 | 2450.00 | 81.58 | 1470.00 |
| Adenine | 135.1 | 0.00 | 0.00 | 0.00 | 0.00 |
| Monobasic sodium phosphate | 120 | 0.00 | 0.00 | 0.00 | 0.00 |
| Mannitol | 182.2 | 0.00 | 0.00 | 0.00 | 0.00 |
| Sodium Chloride | 58.45 | 0.00 | 0.00 | 0.00 | 0.00 |
| Sodium Citrate | 294.1 | 74.80 | 2200.00 | 44.88 | 1320.00 |
| Citric Acid | 192.1 | 41.64 | 800.00 | 24.99 | 480.00 |
| Total Mass (grams) | | | 5.45 | | 3.27 |

It is preferred that a wavelength range of between about 400 and about 500 nm is used to inactivate the microorganisms in a solution consisting mainly of platelets. The most preferred wavelength is 419 nm. Riboflavin in a concentration range of between about 10 and about 30 micromolar is preferred, with a concentration of about 10 micromolar most preferred when a preferred level of plasma is present. A plasma content of between about 0 and about 50 percent of the total volume of the fluid is preferred, with a plasma content less than 25 percent by volume more preferred, with a plasma content less than about 15 percent of the total volume of the fluid being most preferred. It is preferred that platelets be stored and diluted in a solution such as SETOsol (Terumo) or PASIII (Fenwal Labs, Deerfield, Ill.). A light intensity range of between about 40 and 100 mW/cm$^2$ of visible light is preferred, with as high a light intensity as possible being most preferred. A light dose of between about 100 and about 500 J/cm$^2$ is preferred, with between about 100 and about 200 J/cm$^2$ most preferred. A sufficient level of additives may be added to the fluid so that one or more proteins present in said fluid remains biologically active.

It is preferred that a wavelength range of between about 300 and about 500 nm is used to inactivate the microorganisms in fluid consisting mainly of plasma. Both ultraviolet and visible light is currently required. It is presently preferred that a combination of 365, 419 and 447 nm be used. A plasma content between about 50 and 100 percent of the total volume of said fluid is preferred, with a plasma content of about 90 percent of the total volume of said fluid being currently most interesting. A sufficient level of additives may be added to the fluid so that one or more protein present in said fluid remains biologically active after said exposing step. Riboflavin in a concentration range of between about 10 and about 100 micromolar is preferred, with a concentration of about 50 micromolar most preferred for a fluid with the preferred level of plasma. If the plasma is diluted, it is preferably diluted in 0.9% saline. A light intensity of between about 80 and 100 mW/cm$^2$ of visible+ultraviolet light is preferred, with as high a light intensity as possible being most preferred. A light dose of 100 to 500 J/cm$^2$ of light is preferred, with 100 to 200 J/cm$^2$ being most preferred.

Apparatus Design.

The methods of the invention may be used in a variety of devices. The devices generally comprise: a light source producing light having sufficient wavelength and power to induce inactivation of microorganisms which may be present in a sample; and means for positioning the sample so that it receives energy of sufficient wavelength and power to induce inactivation of microorganisms.

The system preferably includes means for producing movement in the sample. Movement provides many benefits including improving the efficiency of the inactivation reactions by helping mix the photosensitizer with the fluid to be deactivated and providing turnover of sample at the container-light interface, for example. An agitator, such as a Helmer flatbed agitation system (Helmer) may be used. This agitator provides oscillatory motion. Other types of agitators may be used to provide motion normal to the bag. If a bag is used as a container, in combination with a source of movement, a pin or other structure may be placed across or within the bag to provide turbulent eddies in the fluid. The agitator may be connected to a computer or other controller in an inactivation system. Some parameters that may be controlled or monitored include temperature of the fluid, energy output of the lights, agitation motion, light control, timing control or monitoring, and other parameters. The light source and fluid being treated may both move to provide agitation of the fluid, or only the fluid being treated may move while the light source remains stationary.

One particular embodiment of the apparatus is an enclosed photoradiation system where the sample would be placed in an apparatus similar to the Bio-Genic irradiator (Vilber-Lourmat, Cedex, France) that uses the appropriate wavelength or wavelengths. Another embodiment is a conveying apparatus used in a large-scale operation to carry samples through a light field or series of light fields.

Means for positioning the sample so that it receives energy of sufficient wavelength and power to induce inactivation of microorganisms include a shelf or tray for the sample to be disposed upon; a gap between two supports which may be a light or light arrays, where the sample is positioned between the supports; or other means as known in the art. The shelf or tray may move, as in a conveyer line. Fluid-holding shelves may be transparent to one or more of the wavelength(s) of light applied.

The sample may be placed in a suitable container on a support surface between two or more sources of photoradiation, like a sandwich. Alternatively, one of the photoradiation-sources may be a reflective material, to allow the light to contact both sides of the sample. Alternatively, or in combination, the sample may be placed on a support and light may impinge on one surface, with agitation, to allow different portions of the sample to be in contact with the light.

Different sources of photoradiation may be used, depending on the wavelength desired and the power desired at the desired wavelength.

Some examples of light sources that may be used include the following. A 20 watt Philips "Blacklight" F20T12/BL emits wavelengths from about 350 nm to about 400 nm. A Philips "Special Blue" F20T12/BB 20 watt light emits wavelengths from about 400 to 500 nm. Ultraviolet Resources International's URI FR20T12 super actinic/VHO-1 CE U123 lamp emits wavelengths from about 400 nm to about 450 nm. Custom Sea Life "Power Compact" 7100K Blue 28 watt Twin Tube emits wavelengths from about 400 nm to about 520 nm. The Sylvania "Blue" F20T12B 20 watt bulb has a broad emission from about 400 nm to about 640 nm. Other representative light sources that may be used include the Armatron "Bug Lights" BF190 8077 Black Light. Mercury lamps may also be used, and have a spectral range from about 300 nm to about 400 nm. Lamps used in tanning booths generally have a spectral range from about 300 to 400 nm. Super Actinic lamps generally have a spectral range from about 400 to about 440 nm, with a peak at 420 nm. Bilirubin lights used to treat infants suffering from jaundice may also be used. For example, a light from Philips Lighting having a peak output at 447 nm and a range of about 420–460 nm may be used.

Lights that emit in the blue spectral range come from various sources. Lamps with peak emissions around 420 to 450 nm may be purchased from LCD Lighting, Orange, Conn.; Bulbtronic, Farmingdale, N.Y.; National Biological Corp., Twinsburg, Ohio; The Fluorescent Co., Saugus, Calif.; Tek-West, Los Angeles, Calif.; or Southern NE UV, Bransford, Conn., for example. LED (light emitting diodes) may also be used. These LEDs may use a variety of materials to produce the desired spectral output, including silicon carbide (bandwidth around 100 nm; peak spectral output near 466 nm) or gallium nitride (bandwidth around 30–35 nm; peak spectral output near 470 nm). Also, lights made from a combination of different materials can generate different wavelengths of light. For example, gallium nitride on a silicon carbide substrate can generate 430 nm. These LEDs are manufactured or distributed by Panasonic, Chicago Miniature, Nichia, Toyoda Gosei, Hewlett Packard, LEDTronics, for example. LED lights typically do not require any outside cooling.

The lights may be used in different ways, depending the particular apparatus. For example, diodes may be duty cycled to emit light when the sample arrives in a flow cell light path. Arrays of diodes may surround the fluid in any desired configuration. In a flat bed apparatus, light arrays may surround the fluid from top or bottom, or both.

Filters, such as color glass filters, may be used to isolate a desired band of the spectrum. Single wavelength or narrow band sources may also be used.

One embodiment of an apparatus useful in the methods of the invention includes banks of interchangeable lights that produce the desired wavelength of light for the particular fluid being treated. Preferred embodiments include using a HID light source to produce 365 nm light that is useful to inactivate microorganisms in plasma. An HID light source is high intensity discharge. A super actinic lamp or a blue LED may be used to produce 419 nm light that is useful in inactivating microorganisms in platelets. A coral or aquarium light may be used to produce wavelengths between 440 and 470 nm that is useful in inactivating microorganisms in red blood cells. The lamps may be provided with separate power supplies to control the level of light output. These lamps may be sequentially placed in position to impinge light on the sample, or the sample may travel through lights of different wavelengths. Different LEDs emitting each desired wavelength may be combined in one array.

Active (cooling through some applied means) or passive (air cooling) cooling may be used if necessary to cool either the lamps or the blood. Fans may provide cooling. One set of fans may be used to cool both the lamps and blood, or different fans may be used to provide different levels of cooling to both the lamps and the blood. A photopermeable fluid may surround the sample and/or lights to provide active cooling. This fluid may be optionally temperature controlled.

EXAMPLES

Example 1

Absorbance Profile of 7,8-dimethyl-10-ribityl isoalloxazine

Figure 1:
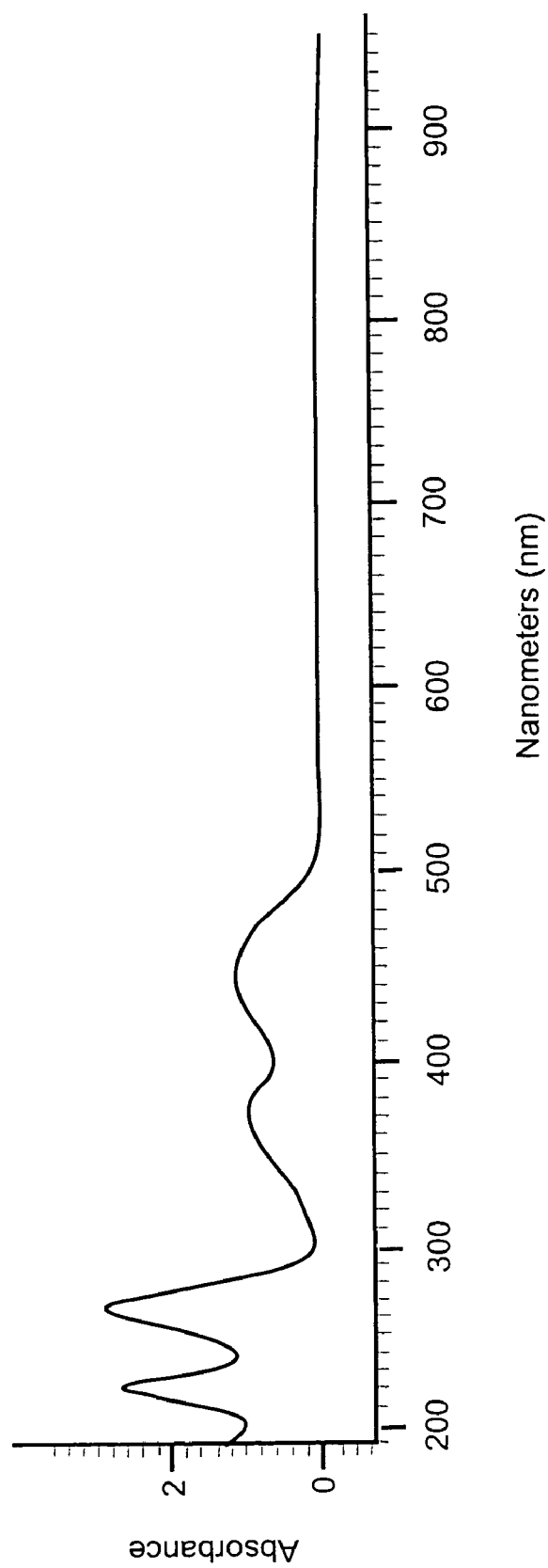
FIG. 1 depicts the riboflavin absorbance spectrum.

A sample of 7,8-dimethyl-10-ribityl isoalloxazine (98% purity) was obtained from Sigma Chemical Company. A portion of this sample was submitted for analysis using a scanning UV spectrophotometer. The range studied covered the region of 200 to 900 nm. For analysis, the sample was dissolved in distilled water. A sample spectrum from this analysis is shown in FIG. 1.

Results were consistent with those reported in the literature for the absorbance maxima and extinction coefficients for 7,8-dimethyl-10-ribityl isoalloxazine

| Literature $\lambda$max ($\epsilon$) | Measured $\lambda$max ($\epsilon$) |
|---|---|
| 267 (32,359) | 222 (30,965) |
|  | 265 (33,159) |
| 373 (10,471) | 373 (10,568) |
| 447 (12,303) | 445 (12,466) |

Appropriate wavelengths for irradiation are 373 and 445 nm. The extinction coefficients observed at these absorbance maxima is sufficient to ensure adequate activation of the sensitizer in solution.

Example 2

Solubility of 7,8-dimethyl-10-ribityl isoalloxazine

Solubility in Isolyte S, pH 7.4 Media

The maximum solubility of 7,8-dimethyl-10-ribityl isoalloxazine in Isolyte S media was determined as follows:

7,8-dimethyl-10-ribityl isoalloxazine was mixed with Isolyte S until a precipitate was formed. The mixture was agitated at room temperature for one hour and vortex mixed to ensure complete dissolution of the suspended material. Additional 7,8-dimethyl-10-ribityl isoalloxazine was added until a solid suspension remained despite additional vortex mixing. This suspension was then centrifuged to remove undissolved material. The supernatant from this preparation was removed and analyzed using a spectrophotometer. The absorbance values of the solution were determined at 447 nm and 373 nm. From the extinction coefficients that were determined previously, it was possible to estimate the concentration of the saturated solution Concentration (373)=110 μM=42 μg/mL Concentration (447)=109 μM=40.9 μg/mL Solubility in ACD-A Anticoagulant The same procedure described above was repeated using ACD-A Anticoagulant. The values obtained from these measurements were as follows:

Concentration (373)=166 μM=63 μg/mL

Concentration (447)=160 μM=60.3 μg/mL

The values obtained from these studies indicate an upper limit of solubility of the compound that may be expected.

Example 3

Figure 3:
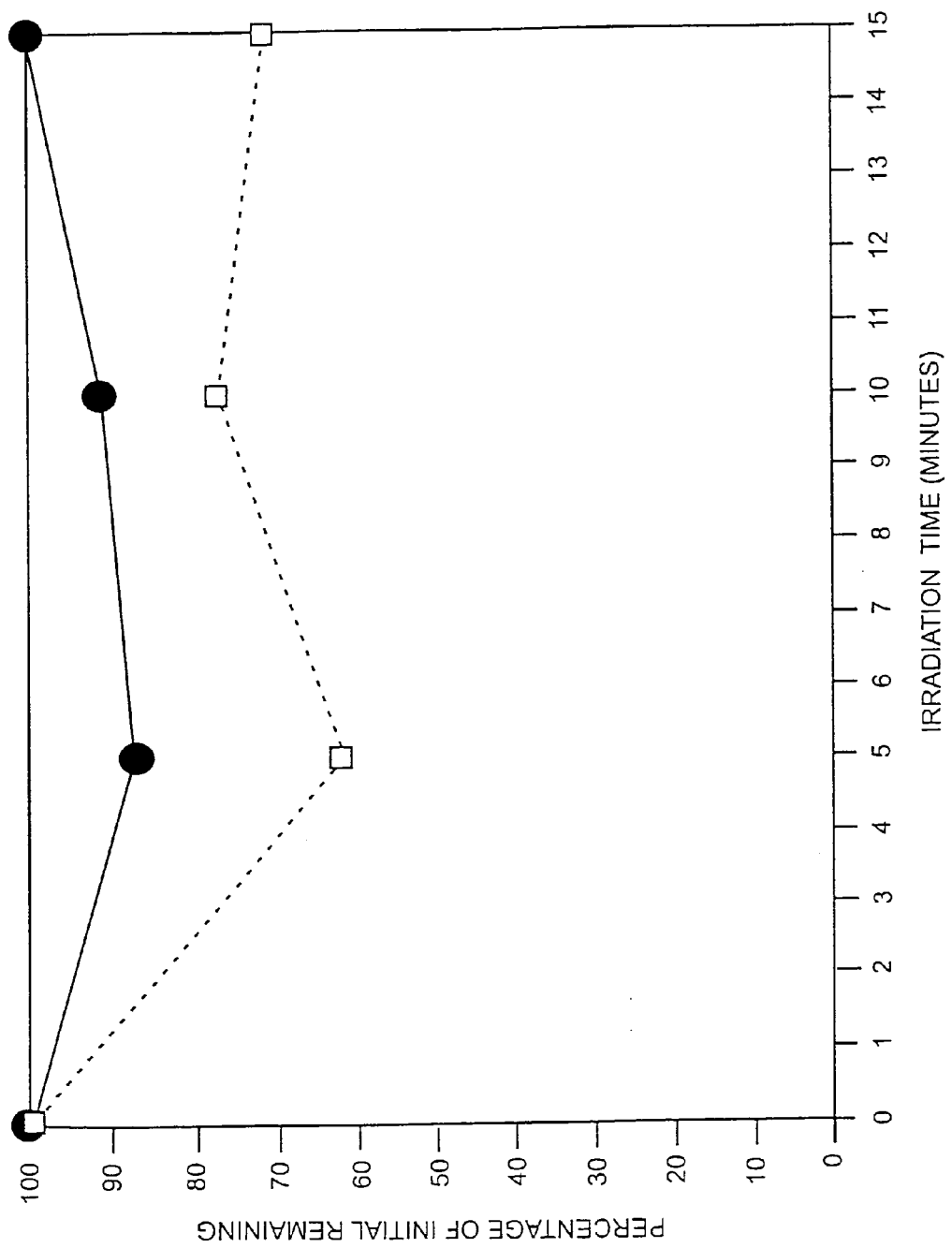
FIG. 3 depicts photodecomposition over time of riboflavin in anticoagulant Acid Citrate Dextrose (ACD) solution. The solid line with circles indicates percent of initial riboflavin remaining at 373 nm. The dotted line with squares indicates percent of initial riboflavin remaining at 447 nm.

Photodecomposition of 7,8-dimethyl-10-ribityl isoalloxazine in Aqueous Media A solution of 7,8-dimethyl-10-ribityl isoalloxazine in Sigma ACD-A was prepared at a concentration of 63 μg/mL. This preparation was taken up into a glass pipette and placed in the path of a UV light source (365 nm λmax with filters to remove light below 320 nm). The suspension was irradiated for specific intervals at which aliquots were removed for spectroscopic analysis. The absorbance of the dissolved 7,8-dimethyl-10-ribityl isoalloxazine was monitored at 373 and 447 nm at each time interval. The results are depicted in FIG. 3 and Table 1.

TABLE 1

Photodecomposition of 7,8-dimethyl-10-ribityl isoalloxazine
Upon Exposure to UV Light (365 nm) in Acid Solution

| Irradiation Time | % of Initial, 373 nm | % of Initial, 447 nm |
|---|---|---|
| 0 | 100 | 100 |
| 5 | 87.3 | 61.6 |
| 10 | 90.5 | 76.6 |
| 15 | 100 | 70 |

The absorption profile for the solution at 373 nm indicates that no significant decomposition of the reagent occurred over the entire irradiation period. The absorbance of light at this wavelength corresponds to n–π* electronic transitions. The absence of a decease in the intensity of this peak over time indicates that the ring structure of the molecule is intact despite prolonged irradiation under these conditions. The absorbance of the molecule at 447 nm is due to π–π* electronic state transitions. The decrease in the absorbance of the molecule at this wavelength with increasing irradiation times is indicative of subtle alterations in the resonance structure of the molecule. This change is most likely due to the loss of ribose from the ring structure of the 7,8-dimethyl isoalloxazine backbone and the formation of 7,8-dimethylalloxozine as a result. These changes are consistent with literature reports on the behavior of the molecule upon irradiation with UV light.

The apparent lack of decomposition of the ring structure of the molecule is in stark contrast to observations with psoralen based compounds under similar conditions. During irradiation, a significant fluorescence of the molecule in solution was observed. This behavior of the molecule is consistent with the resonance features of the ring structure and provides a means for the dissipation of energy in the excited state molecule in a nondestructive fashion.

Example 4

Flow System Concept Evaluation

Light Transmission Properties of Existing Spectra Cuvette

The existing Spectra cuvette is composed of polycarbonate. The light transmission properties of this cuvette were measured at 373 and 447 nm by placing the cuvette in the light path of a UV spectrophotometer. The values obtained were as follows:

| Wavelength of Light | % Transmittance |
|---|---|
| 373 nm | 66% |
| 447 nm | 80% |

Figure 4:
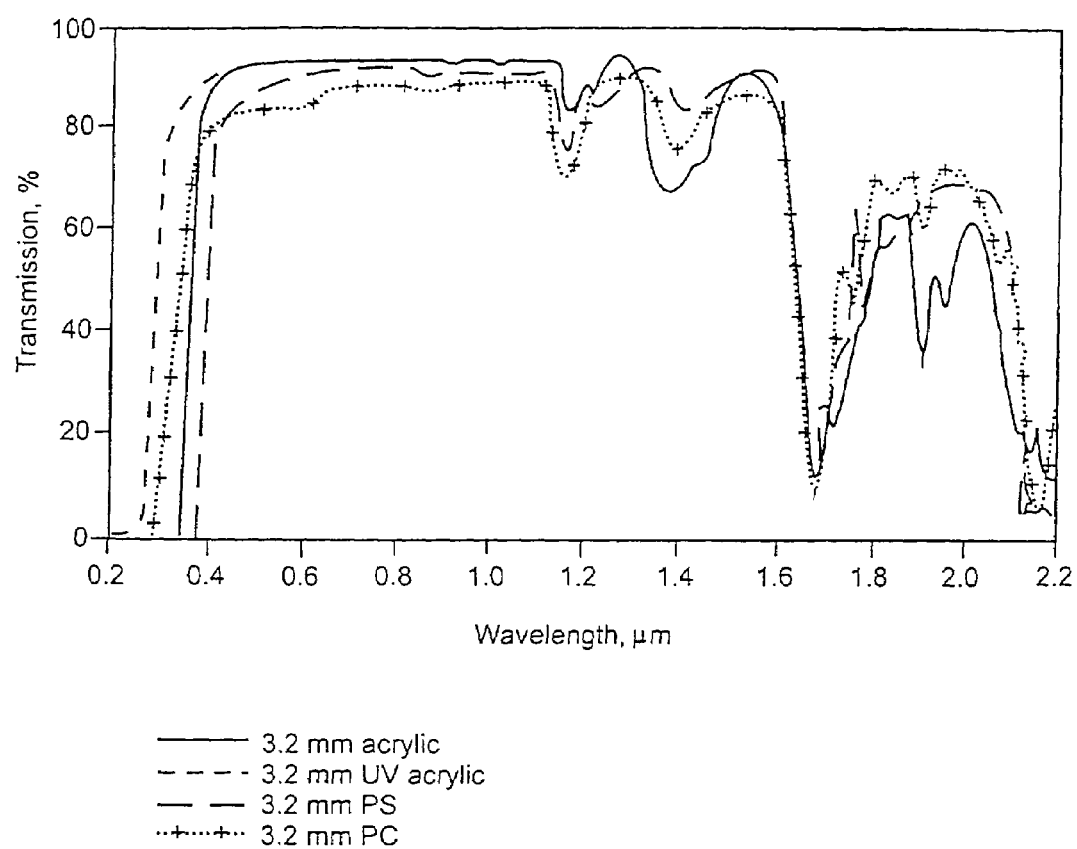
FIG. 4 depicts the transmission profile of various plastic cuvettes as a function of wavelength. The solid line represent a 3.2 mm acrylic cuvette. The dotted line (------) represents a 3.2 mm UV acrylic cuvette. The dashed line (— —) represents a 3.2 mm polystyrene (PS) cuvette, and the crossed line indicates a 3.2 mm polycarbonate (PC) cuvette.

These results are consistent with those reported in the literature for polycarbonate plastics (see FIG. 4). The literature values indicate a steep shoulder for the transmission of light through polycarbonates in the region of 300 nm. For the region above 350 nm, the light transmission properties are adequate for this application.

Light Flux Requirements Calculated as a Function of Flow Rates

In order for a flow system to be feasible, the sample must be provided with an adequate flux of light during its presence in the beam path. If the proposed Spectra cuvette were to serve this purpose, then it is possible to estimate the light flux requirements as a function of flow rates through the cuvette as follows:

The volume of solution present in the irradiation zone of the cuvette is ca. 0.375 mls. The transit time for a cell in this region of the cuvette can be determined from the following equation:

$$T = \frac{\text{Volume of Cuvette (mls)}}{\text{Flow Rate (mls/min)}}$$

At 100 mls per minute, the transit time (T) would be 0.00375 min=0.225 seconds.

The energy to which a sample is exposed is dependent on the flux according to the following equation:

$$\text{Energy } (E, \text{Joules/cm}^2) = \frac{\text{Flux } (\phi, \text{mW/cm}^2) * \text{Time}(T, \text{sec.})}{1000}$$

Figure 5:
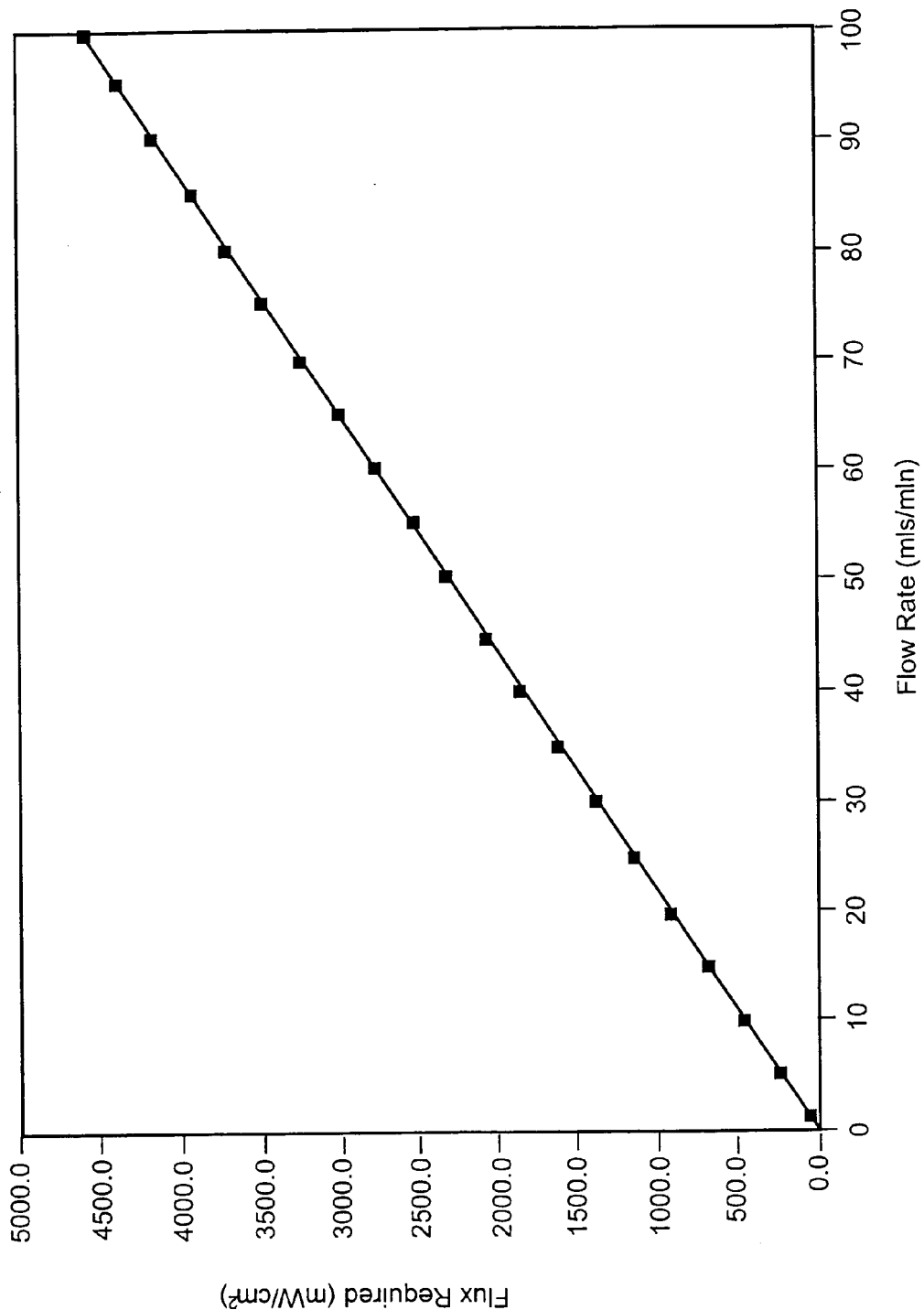
FIG. 5 depicts the light flux required in mW per cm² as a function of flow rate, i.e. the flux required to deliver one joule/cm² to a sample in the cuvette.

If we assume that 1 Joule/cm² is required to activate the sensitizer adequately and the transit time (T) is 0.22 seconds (i.e., flow rate of 100 mls/min through the cuvette), then the required Flux during the sample's transit through the cuvette is 4,545 mW/cm². A graph depicting the relationship of the required flux from the light source to flow rates through the cuvette is provided in FIG. 5.

These results indicate that, for a flow system to operate properly, UV sources with outputs in the region of Watts/cm² are required.

Figure 2:
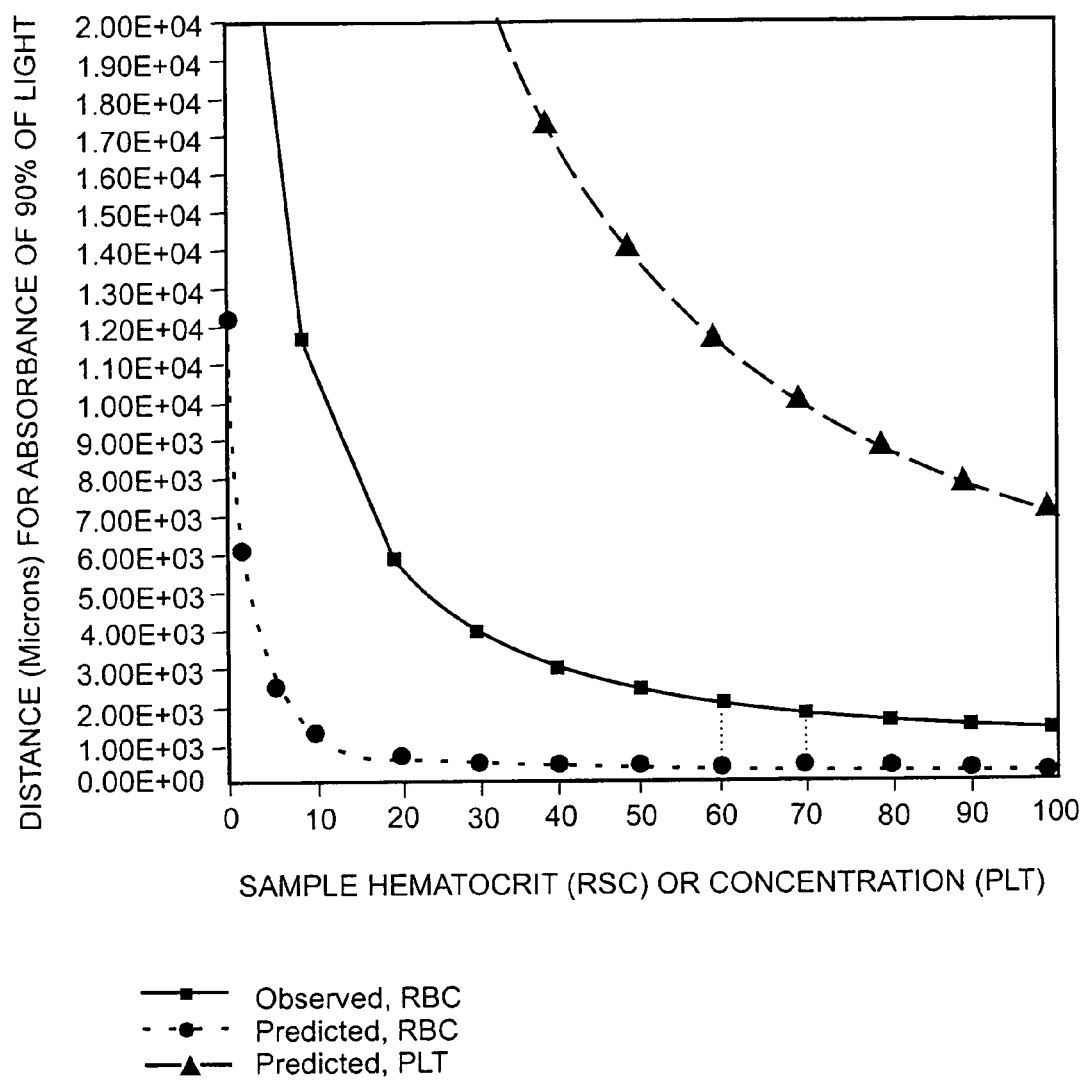
FIG. 2 depicts a correlation of light absorbance and hematocrit observed and predicted for red blood cells, and predicted for platelets.

FIG. 2 shows how absorbance should vary with concentration of platelets.

Example 5

Absorbance of Red Blood Cells

In order to evaluate the extent to which UV light can penetrate a red cell sample and the effects of sample thickness and hematocrit on the extent of light penetration, several preliminary experiments were carried out using chemical actinometry, a method for determining the actual amount of light intensity emanating from a source by measuring the ability and extent to which absorbed light can effect a chemical reaction. For these studies, a ferrioxalate solution was utilized in order to measure the source intensity relative to that observed for water. Details of the chemical reaction and the methods utilized for sample preparation are as taught in Gordon, A. J. and Ford, R. A. (1972), "The Chemist's Companion: Handbook of Practical Data, Techniques and References" (John Wiley & Sons), pp. 362–368.

Samples of iron (III) oxalate were prepared in the test material (water or blood product at varying red cell hematocrits) at a concentration of 0.15 M. These samples were then loaded into a standard Spectra cuvette and placed in the irradiation assembly. Samples were exposed for pre-determined time intervals corresponding to the desired energy dose level (1 J/cm²). The samples were then removed and the amount of conversion of $Fe^{3+}$ to $Fe^{2+}$ was determined by reading the absorbance of the test article in a 1,10-phenanthroline solution at 510 nm as described in Gordon, A. J. and Ford, R. A., supra. Higher absorbance values are indicative of greater light penetration into the sample. The absorbance value observed for water after exposure to 1 J/cm² UV radiation was used as the 100% Transmittance level. All values for red cell samples were relative to this standard.

TABLE 2

Absorbance Readings After Exposure of Samples to 1 J/cm² UVA Light. All Average Values Represent the Mean of 6 Experiments. % Transmittance Values Are Calculated Relative to Water Samples.

| Absorbance at 510 nm | Average | Standard Deviation | % Transmittance | Standard Deviation |
|---|---|---|---|---|
| Water | 2.40 | 0.04 | 100 | 0.0 |
| RBC, 1.3% Hematocrit | 2.40 | 0.10 | 99.5 | 4.8 |

TABLE 2-continued

Absorbance Readings After Exposure of Samples to 1 J/cm² UVA Light. All Average Values Represent the Mean of 6 Experiments. % Transmittance Values Are Calculated Relative to Water Samples.

| Absorbance at 510 nm | Average | Standard Deviation | % Transmittance | Standard Deviation |
|---|---|---|---|---|
| RBC, 3.7% Hematocrit | 1.46 | 0.38 | 60.6 | 15.4 |
| RBC, 5.07% Hematocrit | 0.20 | 0.26 | 8.3 | 10.8 |
| RBC, 6.0% Hematocrit | 0.13 | 0.09 | 5.2 | 3.9 |
| RBC, 10.2% Hematocrit | 0.23 | 0.19 | 9.7 | 7.9 |
| RBC, 16.3% Hematocrit | 0.25 | 0.11 | 10.4 | 4.6 |
| RBC, 21.8% Hematocrit | 0.09 | 0.06 | 3.6 | 2.6 |
| RBC, 80.2% Hematocrit | 0.01 | 0.11 | 0.3 | 4.4 |

Using these values, it is possible to calculate the penetration depth of UV light by using Beer's Law ($A = \epsilon \, b \, C$).

From Lambert's Law, $$\text{Absorbance} = \log (1/\text{Transmittance})$$

If we let the concentration (C) be equal to the hematocrit of the sample, and since b=0.3 cm (the path length of the Spectra cuvette), then it is possible to determine a pseudo-extinction coefficient for the samples ($\epsilon'$) by plotting the absorbance values for the red cell samples versus the product of the hematocrit times the path length. The extinction coefficient for the samples is represented by the slope of this line.

TABLE 3

Determination of Extinction Coefficient for Red Cell Samples.

| T | B | HCT | B*HCT | Absorbance log (1/T) | $\epsilon$ |
|---|---|---|---|---|---|
| 0.995 | 0.3 | 1.3 | 0.39 | 0.002 | .0051 |
| 0.606 | 0.3 | 3.7 | 1.11 | 0.218 | .196 |
| 0.0525 | 0.3 | 6 | 1.8 | 1.280 | .71 |
| 0.097 | 0.3 | 10.2 | 3.06 | 1.013 | .33 |
| 0.104 | 0.3 | 16.3 | 4.89 | 0.983 | .20 |
| 0.036 | 0.3 | 21.8 | 6.54 | 1.444 | .22 |
| 0.0033 | 0.3 | 80.2 | 24.06 | 2.481 | .10 |

Using the values obtained as described above, it was possible to determine a pseudo-extinction coefficient for these samples to be 0.08661.

The value for the extinction coefficient permits calculation of the penetration distance of UV light into red cell samples as a function of the sample hematocrit. For this estimation, the penetration depth of the sample in which 90% of the incident light would be absorbed was determined using the following equation:

$$A = \epsilon b C$$

A=1 (90% Absorbance of Incident Light), $\epsilon$=0.08661, C=Sample hematocrit, b=Path Length.

The values determined using actinometry were compared to those which were calculated previously using estimates taken from UV Spectrophotometric measurements of light absorbance in red cell and platelet samples.

FIG. 2 shows how absorbance and distance from the light source varies for red blood cells, comparing predicted with observed values. These results indicate that, for samples at hematocrits in the region of 80%, it is possible, using the

Example 6

Effects of Virus Inactivation Treatment on Platelet In Vitro Parameters

Effects of virus inactivation treatment on platelet in vitro parameters were evaluated. Platelet preparations were treated with 7,8-dimethyl-10-ribityl isoalloxazine in combination with UV light. Various in vitro parameters were used as monitors of platelet function in order to determine the extent of changes induced by the treatment conditions. Factors such as energy level of UV light exposure, dose of 7,8-dimethyl-10-ribityl isoalloxazine used, and sample processing conditions were examined for their impact on platelet quality post-treatment. Results from this study are used to establish an appropriate treatment window for inactivation of HIV-1 without compromising platelet function.

Samples were prepared with three different concentrations of 7,8-dimethyl-10-ribityl isoalloxazine. Platelets obtained from a standard Spectra LRS collection were used for these studies.

Starting samples were centrifuged to concentrate the platelet pellet. The pellet was resuspended in a 70:30 (Isolyte S, pH 7.4; McGaw, Inc. Media:Plasma) solution. 7,8-dimethyl-10-ribityl isoalloxazine at the specified concentration, was present in the plasma:media mixture. The platelet suspension was then passed through a UV irradiation chamber at one of three specified flow rates. The flow rates were directly correlated to the energy level of exposure for the cells/media mixture which passes through the irradiation chamber. After flowing through the irradiation chamber, samples were stored in a citrate plasticized sampler bag for subsequent analysis.

Following irradiation, in vitro measurements of platelet function, including hypotonic shock response (HSR), GMP-140 expression, pH, $pCO_2$, $pO_2$, platelet swirl, and cell count, were evaluated in order to determine the effects of the treatment protocol on cell quality.

Platelet quality was monitored as a function of irradiation conditions (sensitizer concentration and flow rates/Energy levels). The platelet quality includes parameters such as HSR response, GMP-140 activation, etc. The flow rates that are studied can be related to the Energy of exposure as follows:

$$\text{Transit Time }(T, \text{sec}) = \text{Exposure Time} = \frac{0.375 \text{ mls}}{(F_r/60)}$$

$F_r$ = Flow Rate (mls/min)

$$0.375 \text{ mls} = \text{Cuvette Volume (mls)} \therefore T(\text{sec}) = \frac{22}{F_r}$$

$$\text{Energy (Joules/cm}^2) = \frac{\text{Flux }(\phi, \text{mW/cm}^2) * T(\text{sec})}{1000}$$

$$E = \frac{\phi * 0.022}{F_r}$$

The effect of energy of UV exposure and concentration of 7,8-dimethyl-10-ribityl isoalloxazine on the stability and viability of treated platelets was evaluated. Three energy levels and three concentration levels were evaluated as follows:

| Energy Levels: | 1, 5, 9 J/cm² * |
|---|---|
| 7,8-dimethyl-10-ribityl isoalloxazine Concentrations: | 1, 50, 100 µM ** |

*Levels of total energy exposure were determined by the flow rate of the suspension through the irradiation chamber in accordance with the conversion chart of Table 4.
**Since the media is diluted 70:30 (Media:Plasma) the stock concentration of 7,8-dimethyl-10-ribityl isoalloxazine in media alone prior to mixing with the plasma was adjusted appropriately. This required starting concentrations in Isolyte S of 1.43, 71.4, and 143 µM.

TABLE 4

Energy Exposure Levels as a Function of Flow Rate Through the Irradiation Chamber

| Energy Delivered (J/cm²) | Flow Rate (mls/min) | Time to process 20 mls (minutes) |
|---|---|---|
| 1 | 16.90 | 1.18 |
| 2 | 8.45 | 2.37 |
| 3 | 5.83 | 3.55 |
| 4 | 4.22 | 4.73 |
| 5 | 3.38 | 5.92 |
| 6 | 2.82 | 7.10 |
| 7 | 2.41 | 8.29 |
| 8 | 2.11 | 9.47 |
| 9 | 1.88 | 10.65 |
| 10 | 1.69 | 11.84 |

Flux = 3640 mW/cm²; chamber volume = 0.117 mls.
Values for treated samples were compared to control groups. The control samples included the following:
Untreated Sample in Plasma (Historical Control) + Flow-UV-7,8-dimethyl-10-ribityl isoalloxazine

Procedure

A normal donor platelet apheresis product was obtained from an AABB accredited blood banking facility. The sample was collected using standard Spectra LRS procedures. All manipulations or procedures described below were performed with standard laboratory safety procedures and methods. The unit number and blood type were recorded. All samples were used within 24 hours of collection. Aseptic procedure was followed for all sample transfers and processing steps.

The sample was transferred to a 500 mls PVC transfer pack and centrifuged at 5000×g for five minutes to pack the platelets. Plasma was then removed from the platelet pellet using a standard plasma press. The plasma was retained for further use. The plasma removed from the cell pellet was then mixed with a stock solution of Isolyte S, pH 7.4; McGaw, Inc. This stock solution of media was prepared by adding a pre-determined amount of 7,8-dimethyl-10-ribityl isoalloxazine to Isolyte S to provide final concentrations of 1.43, 71.4, and 143 µM. Following addition of 7,8-dimethyl-10-ribityl isoalloxazine the stock solution was filtered through a 0.22 µM sterile filter. The stock solution was then mixed with autologous plasma in a 70:30 (v:v) ratio to provide final 7,8-dimethyl-10-ribityl isoalloxazine concentrations of 1, 50, and 100 µM respectively. During preparation of the 7,8-dimethyl-10-ribityl isoalloxazine stock solutions, care was taken to avoid exposure to light. Samples were prepared according as follows:

1 µM 2 samples
100 µM 2 samples
50 µM 1 sample

The platelet pellet was then resuspended in the plasma:media mixture to the original volume of the starting sample.

The sample was connected to a flow apparatus comprising a container for cells and photosensitizer, a container for media, said containers being connected via valved lines to a single line for mixed cells/sensitizer and media equipped with a pump. Mixed cells/sensitizer and media were flowed into a cuvette held in a holder with a mirrored wall, irradiated by a light source. This irradiation chamber was equipped with a temperature probe. After passing through the cuvette, fluid was collected in a product bag.

The tubing set was initially primed with Isolyte S media. Five minutes prior to the start of the test sample flow, the light source was activated. Temperature was monitored during this interval and kept lower than 32° C. in the irradiation chamber.

The flow rate for the sample through the irradiation chamber was determined by the chart of Table 4. Flow rates which provide total irradiation energy levels of 1, 5 and 9 J/cm$^2$ were utilized according to the following testing matrix:

Sample Run #1: 7,8-dimethyl-10-ribityl isoalloxazine Concentration=1 µM

A. +7,8-dimethyl-10-ribityl isoalloxazine+1 J/cm$^2$
B. +7,8-dimethyl-10-ribityl isoalloxazine+9 J/cm$^2$ Sample Run #2: 7,8-dimethyl-10-ribityl isoalloxazine=100 µM A. +7,8-dimethyl-10-ribityl isoalloxazine+1 J/cm$^2$
B. +7,8-dimethyl-10-ribityl isoalloxazine+9 J/cm$^2$ Sample Run #3: 7,8-dimethyl-10-ribityl isoalloxazine=50 µM A. +7,8-dimethyl-10-ribityl isoalloxazine+5 J/cm$^2$ Sample Run #4: Control Sample, 7,8-dimethyl-10-ribityl isoalloxazine=0 µM A. +Flow-UV-7,8-dimethyl-10-ribityl isoalloxazine All samples were identified by the run number and sample letter designation corresponding to treatment condition (i.e., 1A). Each sample set was run for a total of 2 replicates. The order in which samples were treated was determined by assignment according to a random number generator.

A sample volume of 20 mls per run condition was collected for each sample. These samples were collected into citrate plasticized sampling bags (53 mls total volume) and stored for analysis. The temperature of the sample and the irradiation chamber was noted at the start, mid-point, and end of each run.

An initial aliquot from each preparation was removed post-treatment for analysis. Parameters for analysis included cell count, pH, pCO$_2$, pO$_2$, platelet swirl, HSR, and GMP-140 analysis. The remaining portion of the sample was placed in an end-over-end platelet agitator in a +22 incubator and stored for five days post-treatment. On day 5, a second aliquot was removed and analyzed for the same in vitro parameters.

The following equipment was used: Nikon Labophot microscope; Serono-Baker System 9000 Hematology Analyzer; analytical balance; platelet incubator (+22 Celsius) and rotator; laboratory refrigerator (+4 Celsius); Mistral 3000i Centrifuge; Corning Blood Gas Analyzer; Becton-Dickinson FACSCALIBUR Flow Cytometer; UV irradiation chamber; UV radiometer (UVX Radiometer, UVP, Inc.); EFOS Ultracure 100SS Plus (365 nm maximum output and 340 nm bandpass filters); and temperature probe (thermocouple).

Results for each set of test variables were compared for the defined conditions of energy of exposure and concentration of 7,8-dimethyl-10-ribityl isoalloxazine. Direct comparison to the untreated control sample was made and significant differences defined by a probability p>0.05 from a paired, one-tailed, Student's T-Test analysis.

The results from these studies were summarized as follows:

4. At sensitizer concentrations in excess of 10 µM and platelet concentrations above 1.5E+06/µL, there was a drop in sample pH by day 2. The pH declined steadily beyond day 2 of storage reaching unacceptable levels (<6.5) by day 3 of storage. All other in vitro parameters followed the pattern observed with sample pH.
5. This decrease in sample pH occurred regardless of whether or not the sample was exposed to UV light.
6. At platelet concentrations of 5.4E+05/µL, there was no drop in sample pH after extended storage at any sensitizer concentration studied up to 100 µM.
7. At sensitizer concentrations up to 10 µM, platelet concentrations above 1.5E+06 µL, and UVA levels up to 10 J/cm$^2$, measured platelet properties were comparable to control, untreated cells. These remained comparable to control levels after five or more days of storage post-treatment.

These studies on platelet function post-treatment provided a clear window in which cell properties were maintained at levels comparable to untreated cells. The results also indicated that by varying the storage or treatment conditions for the cells this window can be expanded. The observed effect of 7,8-dimethyl-10-ribityl isoalloxazine with or without UV light on sample pH suggests a metabolic effect of this additive which may be moderated by changes in the storage or processing conditions of the samples.

Example 7

Measurements of Shear Stresses on Red Cells As a Function of Flow Rate and Sample Hematocrit The low levels of UV light penetration into red cell samples at high hematocrits raised the need to understand the effects of passing red cells through narrow openings in the light path. Reduction in sample thickness in the light path should increase delivery of UV dose at high sample hematocrits. In order to confirm this approach, several pressure drop measurements were undertaken using openings of varying dimensions. A pressure gauge was placed in line with a peristaltic pump both upstream and downstream from the narrowed openings. Whole blood of varying hematocrits was passed through the openings at controlled flow rates. Differences in the pressure readings at both locations permitted direct measurement of the pressure drop across the opening. Using this value and the dimensions of the opening, it was possible to determine the shear stress experienced by the red cells as they passed through the narrowed cell using the following equation:

$$\Delta P = \frac{8 \mu l Q}{g d^3 w} \quad \text{Pressure Drop}$$

$$\tau_w = \frac{4 \mu Q}{g w d^2} \quad \text{Shear Stress}$$

For blood,

μ=Viscosity=0.0125/(1-Hematocrit)
g=gravitational constant=981
Q=Flow Rate=mls/sec
l, w, d=Dimensions of opening in cm

TABLE 5

Measurement of Shear Stress on Red Cells
As Functions of Flow Rate and Sample Hematocrit

|  |  | 0.08 × 0.008 | Dpmeas (dynes/ $cm^2$) | 0.08 × 0010 | Dpmeas (dynes/ $cm^2$) | 0.08 × 0.012 | Dpmeas (dynes/ $cm^2$) |
|---|---|---|---|---|---|---|---|
| 41% HCT | Q = 3.38 | 1.5 | 95.9 | 1.0 | 77.6 | 0.0 | 0.0 |
| 64% HCT | Q = 3.38 | 4.0 | 255.8 | 3.0 | 232.9 | 2.0 | 182.1 |
| 41% HCT | Q = 16.9 | 9.7 | 618.4 | 7.0 | 543.4 | 4.7 | 425.3 |
| 61% HCT | Q = 16.9 | 20.7 | 1321.9 | 12.3 | 957.2 | 8.7 | 789.6 |

|  |  | 0.10 × 0.008 | Dpmeas (dynes/ $cm^2$) | 0.1 × 0.010 | Dpmeas (dynes/ $cm^2$) | 0.1 × 0.012 | Dpmeas (dynes/ $cm^2$) |
|---|---|---|---|---|---|---|---|
| 41% HCT | Q = 3.38 | 2.0 | 93.7 | 1.0 | 60.3 | 1.0 | 73.5 |
| 64% HCT | Q = 3.38 | 4.5 | 210.8 | 3.0 | 180.9 | 2.0 | 146.9 |
| 41% HCT | Q = 16.9 | 12.7 | 593.6 | 7.0 | 422.1 | 4.7 | 343.0 |
| 61% HCT | Q = 16.9 | 23.3 | 1093.0 | 14.7 | 884.6 | 12.0 | 881.4 |

|  |  | 0.15 × 0.008 | Dpmeas (dynes/ $cm^2$) | 0.15 × 0.010 | Dpmeas (dynes/ $cm^2$) | 0.15 × 0.012 | Dpmeas (dynes/ $cm^2$) |
|---|---|---|---|---|---|---|---|
| 41% HCT | Q = 3.38 | 3.0 | 97.4 | 1.2 | 49.2 | 1.0 | 49.0 |
| 64% HCT | Q = 3.38 | 6.5 | 211.0 | 3.5 | 143.5 | 2.0 | 97.9 |
| 41% HCT | Q = 16.9 | 15.3 | 497.7 | 8.3 | 341.6 | 5.7 | 277.6 |
| 61% HCT | Q = 16.9 | 35.7 | 1158.5 | 18.0 | 738.1 | 12.7 | 620.4 |

In previous experiments, it was determined that shear stresses of 1,000–2,000 dynes/cm² for intervals of 1–10 minutes or levels of 5,000–7,000 dynes/cm² for intervals of approximately 10 msec were sufficient to induce red cell hemolysis. Only in the case of the highest sample hematocrit (61%) and highest flow rate (16.9) did values exceed 1,000 dynes/cm². This occurred only for openings of the narrowest width (0.008 inches).

Values for the light penetration depth using the proposed configuration indicate that delivery in sufficient UV energy to drive virus inactivation processes is achievable even for samples with high hematocrits.

Results from shear stress analysis on red cell samples subjected to flow indicate that flow path dimensions may be significantly reduced and high flow rates maintained without risking red cell hemolysis.

Example 8

A platelet concentrate was mixed with the platelet additive solution Isolyte S at a ratio of 20:80 platelet concentrate: Isolyte S. Mixtures of platelet concentrates and platelet additive solutions are referred to herein as in "media." Platelet concentrate without additive solution is referred to herein as in "plasma." Both were spiked with *Listeria monocytogenes*. Vitamin K5 was then added to each in the amount of 300 μg/mL B. Each was then exposed to UV, visible or room light in the cuvette apparatus of FIG. 7 with the results shown in Table 6.

TABLE 6

|  | Log Inactivation (cfu/mL) | |
|---|---|---|
|  | K5 in Media | K5 in Plasma |
| UV, 40 J/cm² | 4.2 Logs | 0.1 Logs |
| VIS, 40 J/cm² | 4.2 Logs | 0.1 Logs |
| Room Light | 0 Logs | 0 Logs |

UV Light = 365 nm
VIS Light = 419 nm

UV Light=365 nm
VIS Light=419 nm
Pathogen=*Listeria monocytogenes*
Concentration of K5=300 μg/mL Example 9

Media and plasma as described above containing vitamin K5 were spiked with bacteria and irradiated or exposed to room light only (K5-light) as shown in Table 7, and growth evaluated after three days of incubation. Inactivation of some species was seen in the absence of irradiation.

TABLE 7

|  |  | Media | | Plasma | |
|---|---|---|---|---|---|
|  | Spike Level (cfu/mL) | K5+ Light | K5− Light | K5+ Light | K5− Light |
| *P. aeruginosa* | 3.4 Logs | − | − | − | − |
| *S. aureus* | 2.1 Logs | − | − | + | + |
| *S. epidermidis* | 3.2 Logs | − | + | − | − |
| *L. monocytogenes* | 3.5 Logs | − | − | + | + |
| *E. coli* | 3.1 Logs | − | − | + | − |

UV Light = 365 nm, 40 J/cm²
+ = Growth detected after three days incubation
− = No Growth detected after three days incubation
Concentration of K5 = 300 μg/mL Example 10

Figure 8:
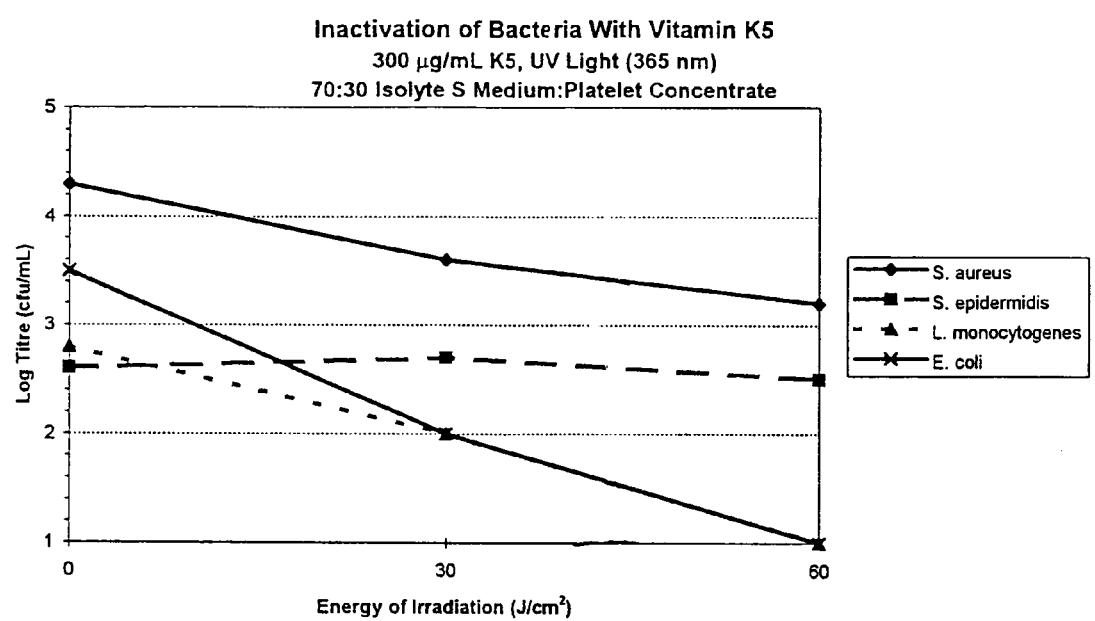
FIG. 8 depicts inactivation of bacteria in platelet preparations using vitamin K5 as the photosensitizer as a function of energy of irradiation.

Media made using a platelet concentrate as described in Example 8 and Isolyte S at a ratio of Isolyte S:platelet concentrate of 70:30 and containing 300 μg/mL vitamin K5 was spiked with several species of bacteria and irradiated at energy levels of 30 and 60 J/cm². Inactivation as a function of energy of irradiation is set forth in Table 8 and FIG. 8.

TABLE 8

| Energy (J/cm²) | *S. aureus* | *S. epidermidis* | *L. monocytogenes* | *E. coli* |
|---|---|---|---|---|
| 0 | 4.3 | 2.6 | 2.8 | 3.5 |
| 30 | 3.6 | 2.7 | 2 | 2 |
| 60 | 3.2 | 2.5 | 1 | 1 |

Example 11

To platelet concentrate as described in Example 8 and to 70:30 media as described in Example 10 was added 10 μM of 7,8-dimethyl-10-ribityl isoalloxazine. The platelet concentrate and media were spiked with *S. aureus* or *S. epider-*

Figure 9:
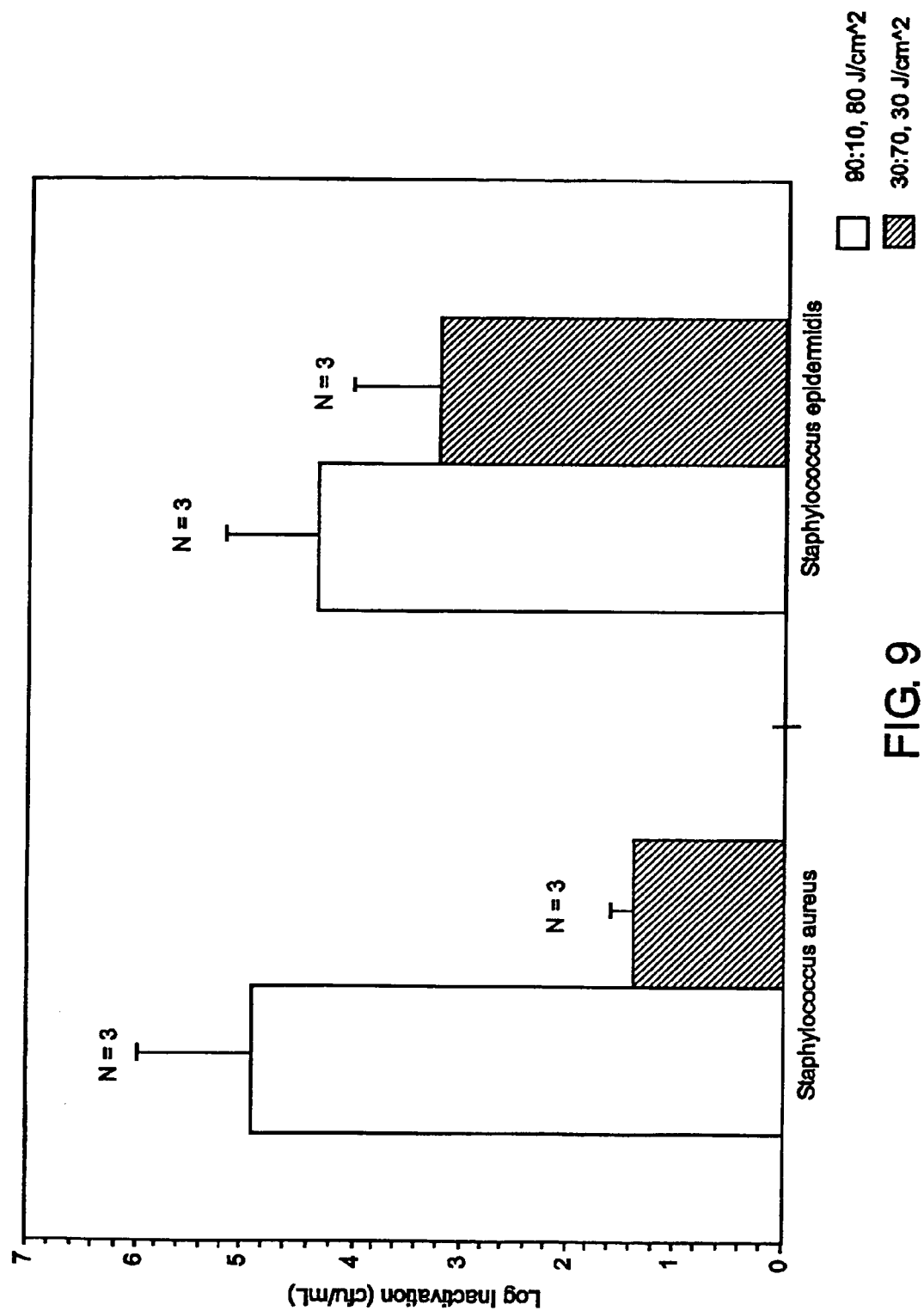
FIG. 9 depicts inactivation of bacteria as a function of platelet preparation and energy of irradiation, using 90% platelets and 10% platelet additive solution (90:10) and 30% platelets with 70% additive solution (30:70).

*midis*, and irradiated at 80 J/cm² and 30 J/cm² and inactivation measured as above. Results are shown in FIG. 9.

Example 12

To plasma concentrate as described in Example 8 contained in a standard blood bag was added 25 μM 7,8-dimethyl-10-ribityl isoalloxazine in powder form. The bag was spiked with bacteria as shown in Table 9, agitated and exposed to 120 J/cm² radiation. Inactivation results are set forth in Table 9.

TABLE 9

| Pathogen | Log Inactivation (cfu/mL) |
|---|---|
| S. aureus | 1.7 Logs |
| S. epidermidis | 3.5 Logs |
| P. aeruginosa | 3.6 Logs |
| E. coli | 4.1 Logs |

Example 13

To platelet concentrate as described in Example 8 was added 7,8-dimethyl-10-ribityl isoalloxazine, alloxazine mononucleotide, or 7-8-dimethyl alloxazine, followed by spiking with S. aureus or S. epidermidis, and irradiation at 80 J/cm². Inactivation results are shown in Table 10.

TABLE 10

|  | Log Inactivation (cfu/mL) | |
|---|---|---|
|  | Staphylococcus aureus | Staphylococcus epidermidis |
| 7,8-dimethyl-10-ribityl isoalloxazine, 10 μM | 1.9 Logs | 4.1 Logs |
| alloxazine mononucleotide, 10 μM | 1.6 Logs | 5.6 Logs |
| 7-8-dimethyl alloxazine, 7 μM | 1.6 Logs | 2.9 Logs |

Example 14

Figure 10:
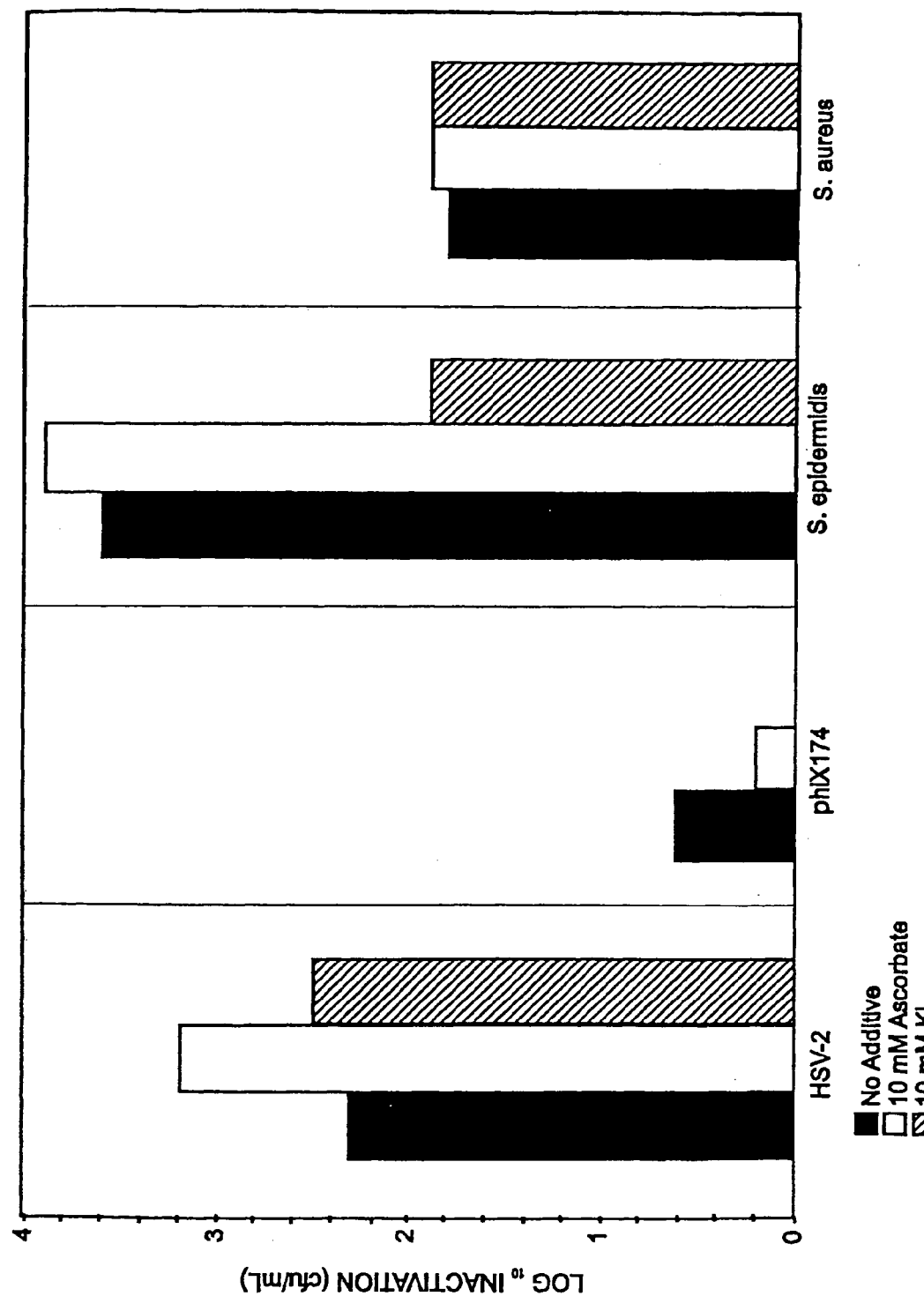
FIG. 10 shows the effect on inactivation of virus, bacteriophage and bacteria of adding antioxidants to platelet concentrate.

To platelet concentrate of Example 8 was added 10 μM 7,8-dimethyl-10-ribityl-isoalloxazine. Aliquots contained no additive, 10 micromolar ascorbate or 10 micromolar KI as a "quencher" or antioxidant. The solutions were spiked with HSV-2, ΦX174, S. epidermidis or S. aureus and irradiated at 80 J/cm². Results are shown in FIG. 10.

Example 15

Figure 11:
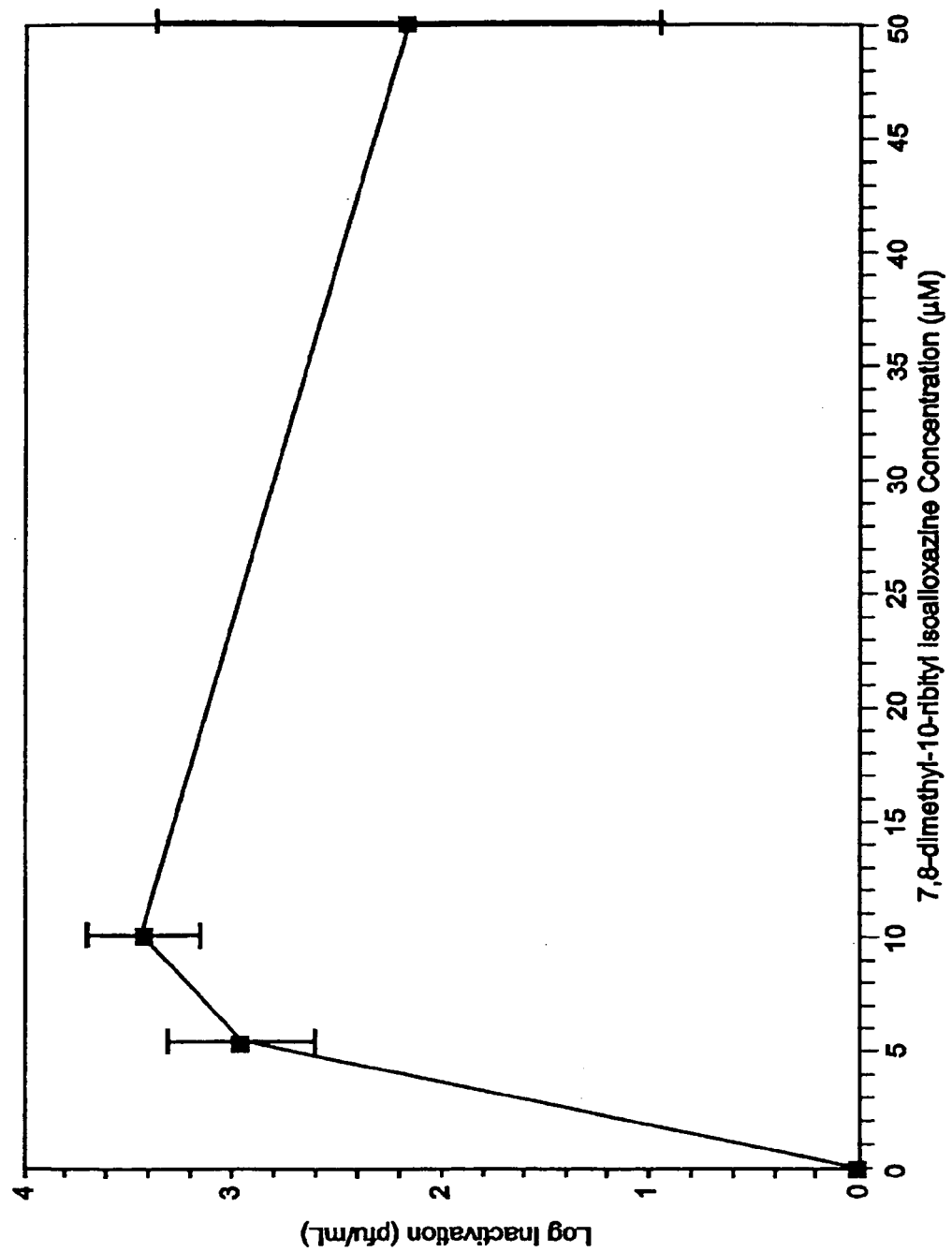
FIG. 11 shows the inactivation curve for Herpes Simplex type II virus as a function of concentration of photosensitizer at an energy of irradiation of 20 J/cm² using half ultraviolet and half visible light.

To platelet concentrates of Example 8 were added varying concentrations of 7,8-dimethyl-10-ribityl-isoalloxazine. These solutions were spiked with herpes simplex virus type II (HSV-II), a double-stranded DNA envelope virus. Irradiation was done at 80 J/cm². The experiment was replicated three times. In all three trials complete inactivation was achieved. Results are shown in FIG. 11.

Example 16

Figure 12:
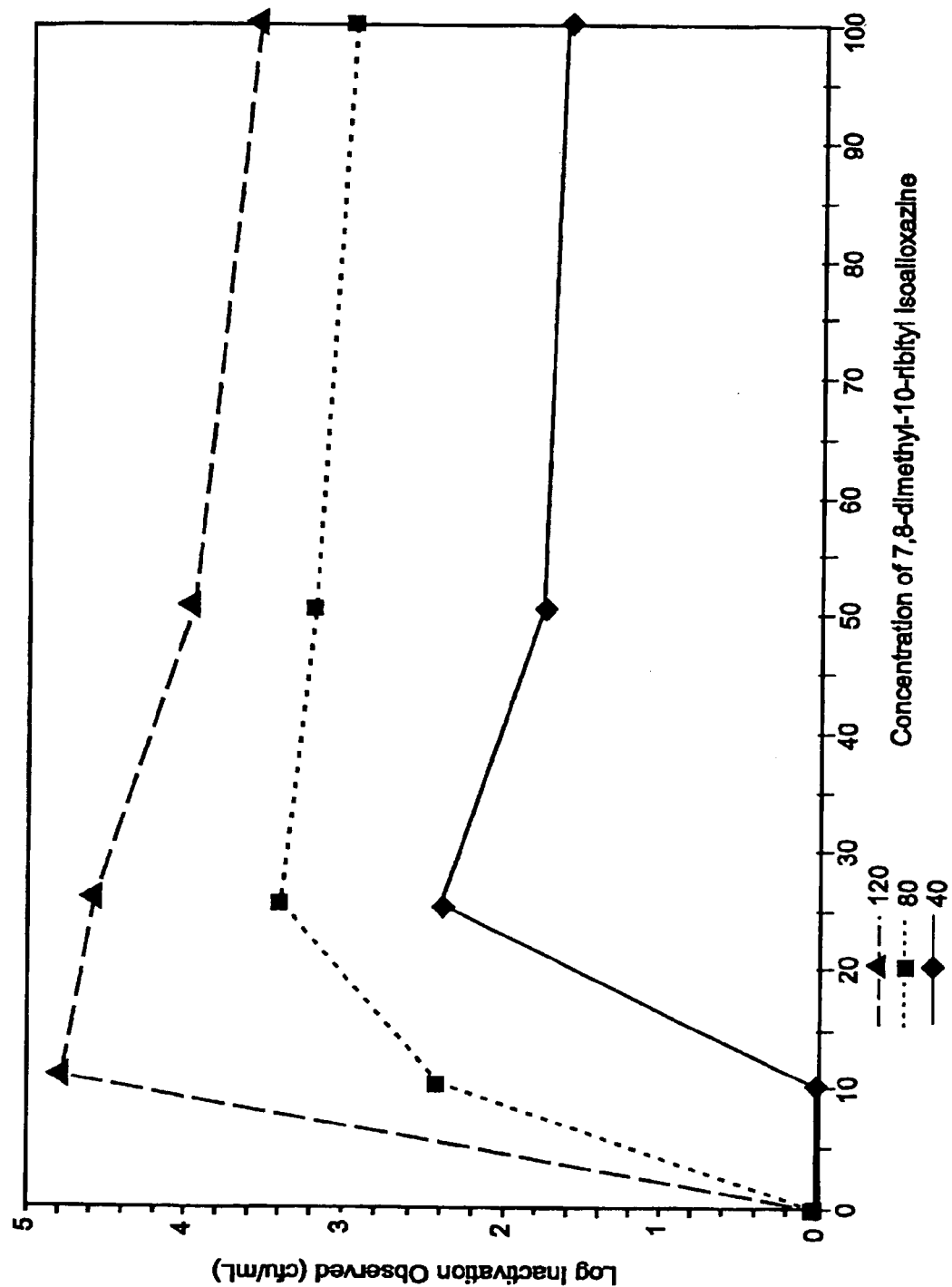
FIG. 12 shows inactivation of S. epidermidis at varying concentrations of photosensitizer and energies of irradiation.

The protocol of Example 15 was followed using S. epidermidis instead of HSV II at energies of irradiation of 40, 80 and 120 J/cm². Inactivation results are shown in FIG. 12.

Example 17

Figure 13:
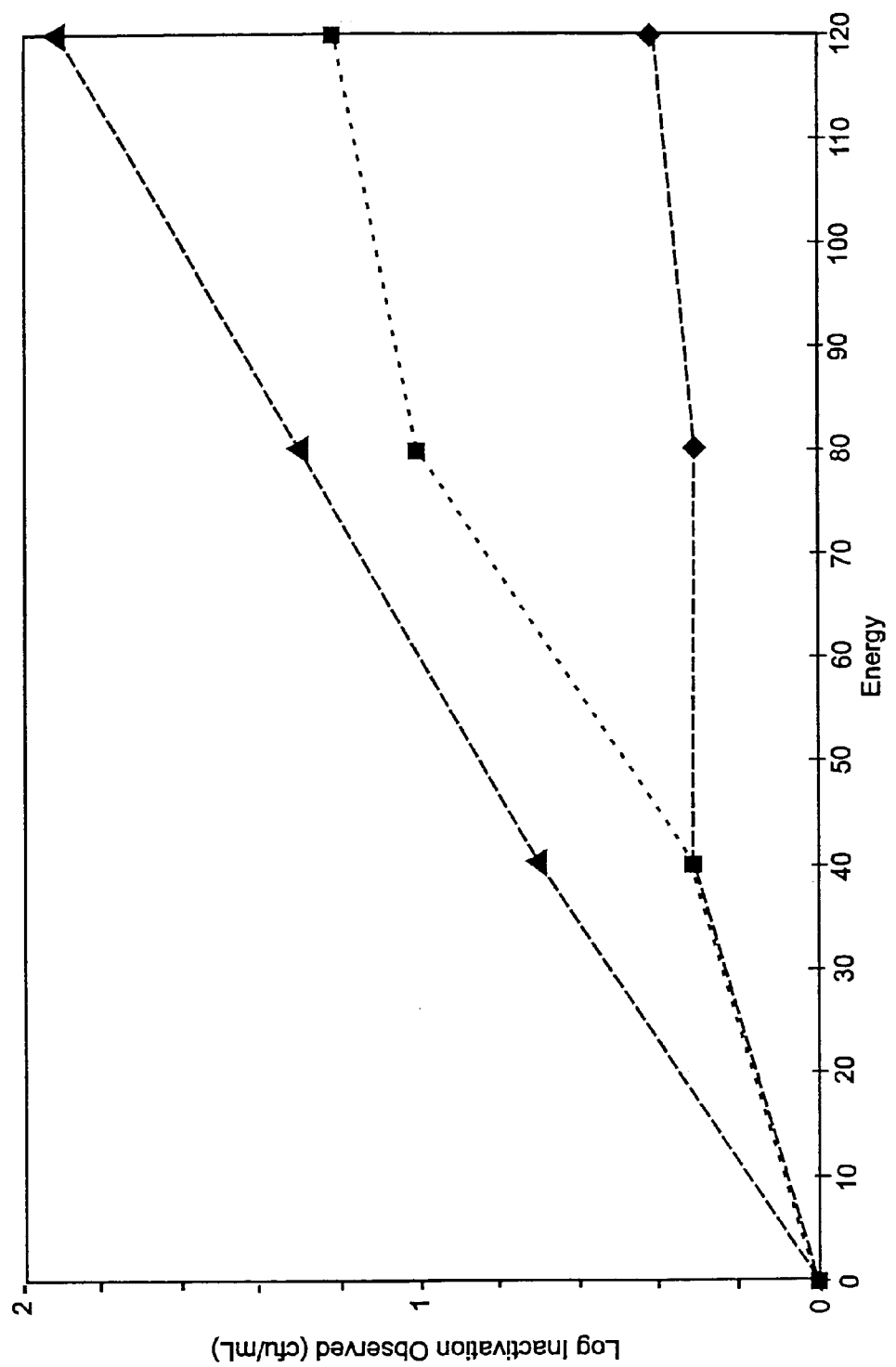
FIG. 13 shows inactivation of ΦX174 at varying concentrations of photosensitizer and energies of irradiation.

The protocol of Example 15 was followed using ΦX174, a single stranded DNA bacteriophage, at varying concentrations of 7,8-dimethyl-10-ribityl-isoalloxazine and energies of irradiation. Inactivation results are shown in FIG. 13.

Example 18

Figure 14:
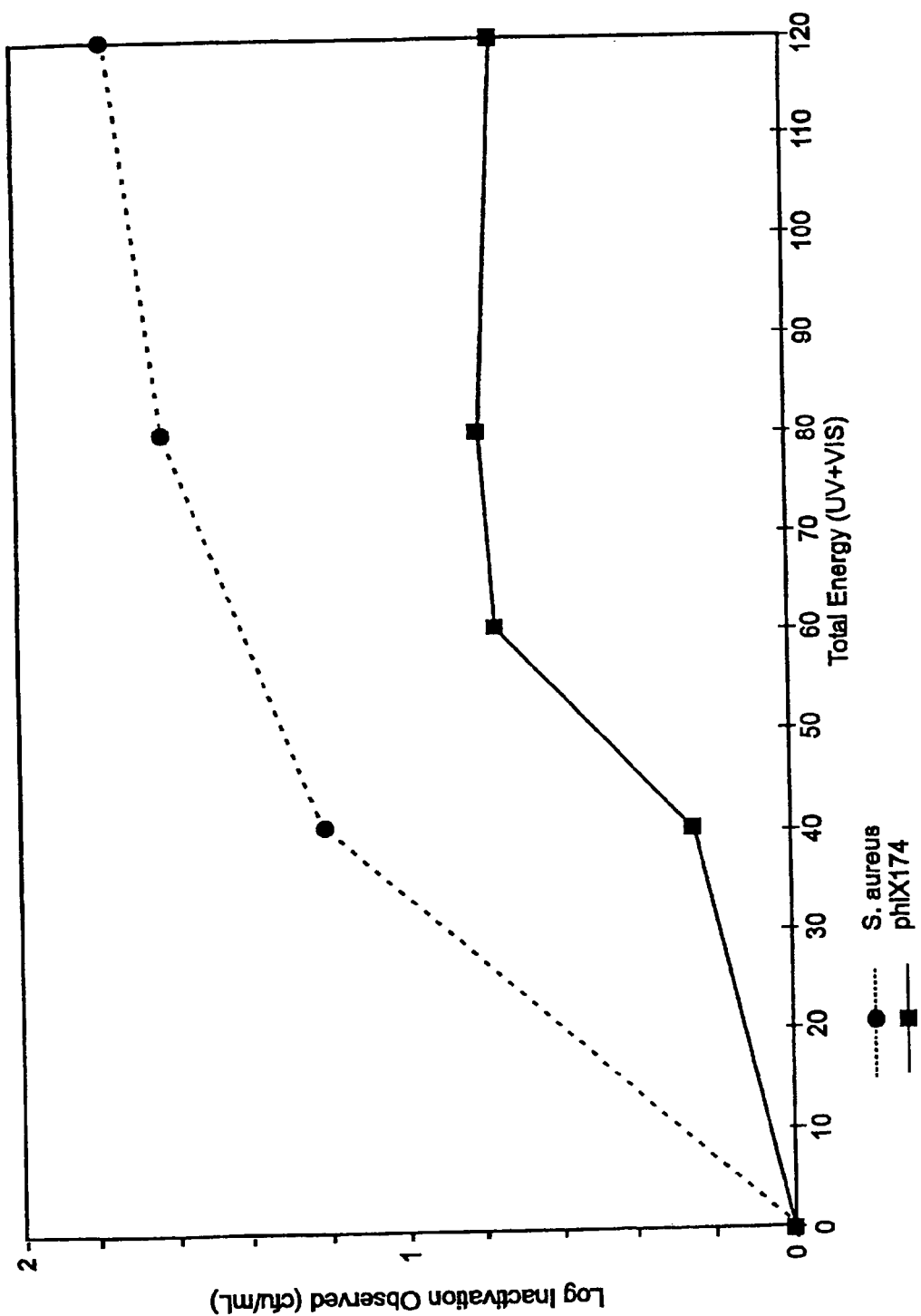
FIG. 14 shows inactivation of S. aureus and ΦX174 at varying energies of irradiation using a 50:50 mixture of ultraviolet and visible light.

To platelet concentrates of Example 8 was added 10 μM 7,8-dimethyl-10-ribityl-isoalloxazine. These were spiked with S. aureus or ΦX174 and irradiated at varying energies of irradiation with a 50:50 mixture of visible and ultraviolet light. Inactivation results are shown in FIG. 14.

Example 19

Figure 15:
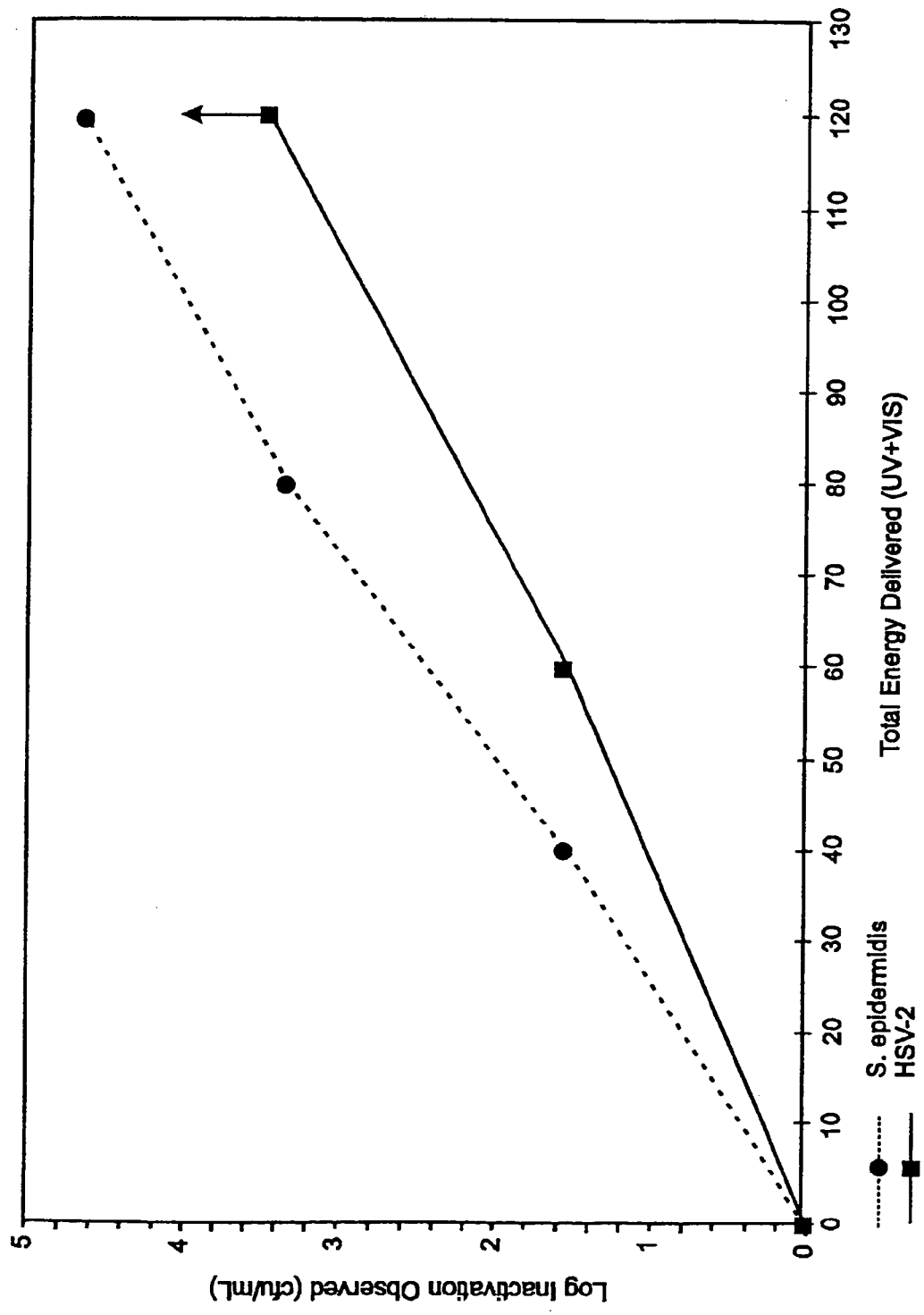
FIG. 15 shows inactivation of S. epidermidis and HSV-II at varying energies of irradiation using a 50:50 mixture of ultraviolet and visible light.

The protocol of Example 18 was followed using S. epidermidis and HSV-II as the microorganisms. A 50:50 mixture of ultraviolet and visible light was supplied by DYMAX light source. Inactivation results are shown in FIG. 15.

Example 20

Figure 16:
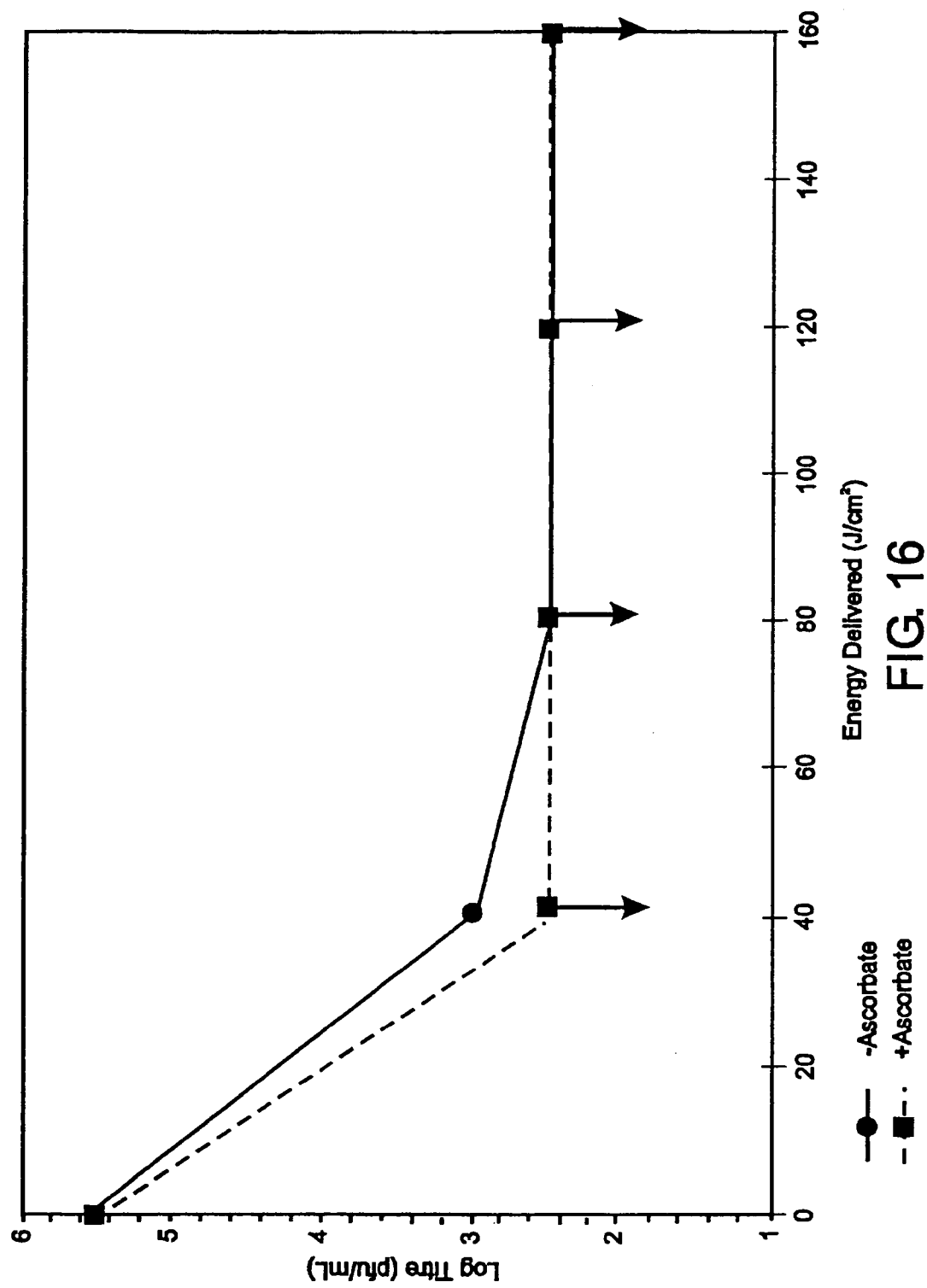
FIG. 16 shows inactivation of HSV2 virus in blood bags agitated and irradiated at varying energy levels.

To platelet concentrate of Example 8 was added 10 μM 7,8-dimethyl-10-ribityl-isoalloxazine in powdered form. Tests with and without added ascorbate were conducted. 150 ml of the test solutions were placed in a Spectra™ blood bag and shaken and exposed to varying energies of irradiation using 50:50 visible:ultraviolet light. After receiving 40 J/cm², the contents of each bag were transferred to a new bag to avoid errors due to microorganisms which may have remained in the spike port of the bag. Inactivation results are shown in FIG. 16. Downward arrows indicate inactivation to the level it was possible to detect (2.5 log titre).

Example 21

Figure 17:
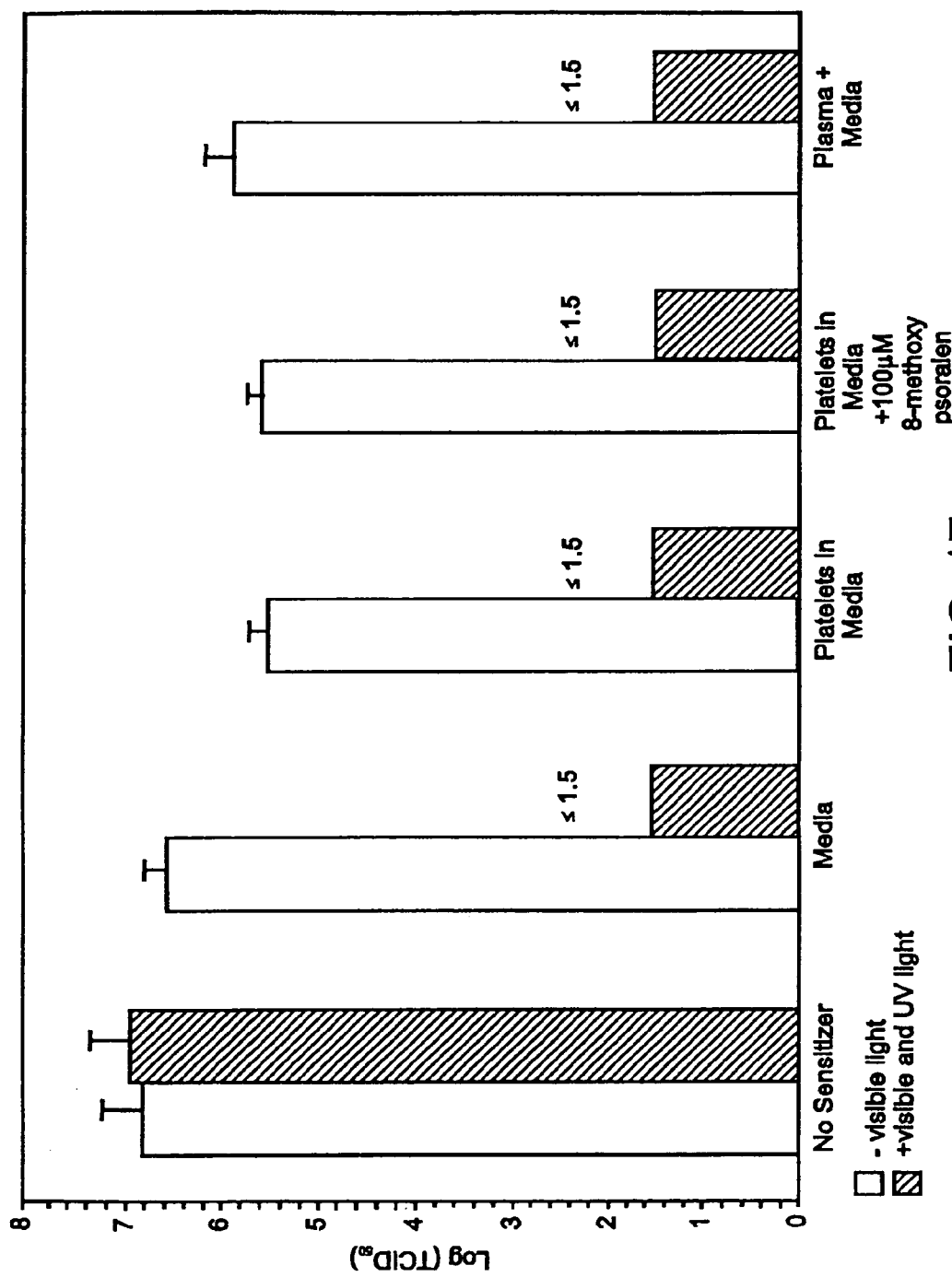
FIG. 17 compares inactivation results for vaccinia virus in various fluids using ultraviolet light alone or 50:50 visible and ultraviolet light.

To platelet concentrate of Example 8 and platelet concentrate in Isolyte S at 30:70 platelet concentrate:Isolyte S, was added 20 μM 7,8-dimethyl-10-ribityl-isoalloxazine. These were spiked with vaccinia virus, a double stranded DNA envelope virus, and exposed to 60 J/cm² visible light or mixed (50:50) visible and ultraviolet light using a DYMAX 2000 UV (Torrington, Conn.) light source for 30 minutes. The limit of detection was 1.5 logs. Inactivation results are show in FIG. 17. Comparisons were done using no photosensitizer, photosensitizer in Isolyte S media alone, platelets in Isolyte S media, platelets in Isolyte S media using 8-methoxy psoralen instead of 7,8-dimethyl-10-ribityl-isoalloxazine, and platelet concentrate in Isolyte media (30:70).

Example 22

Figure 18:
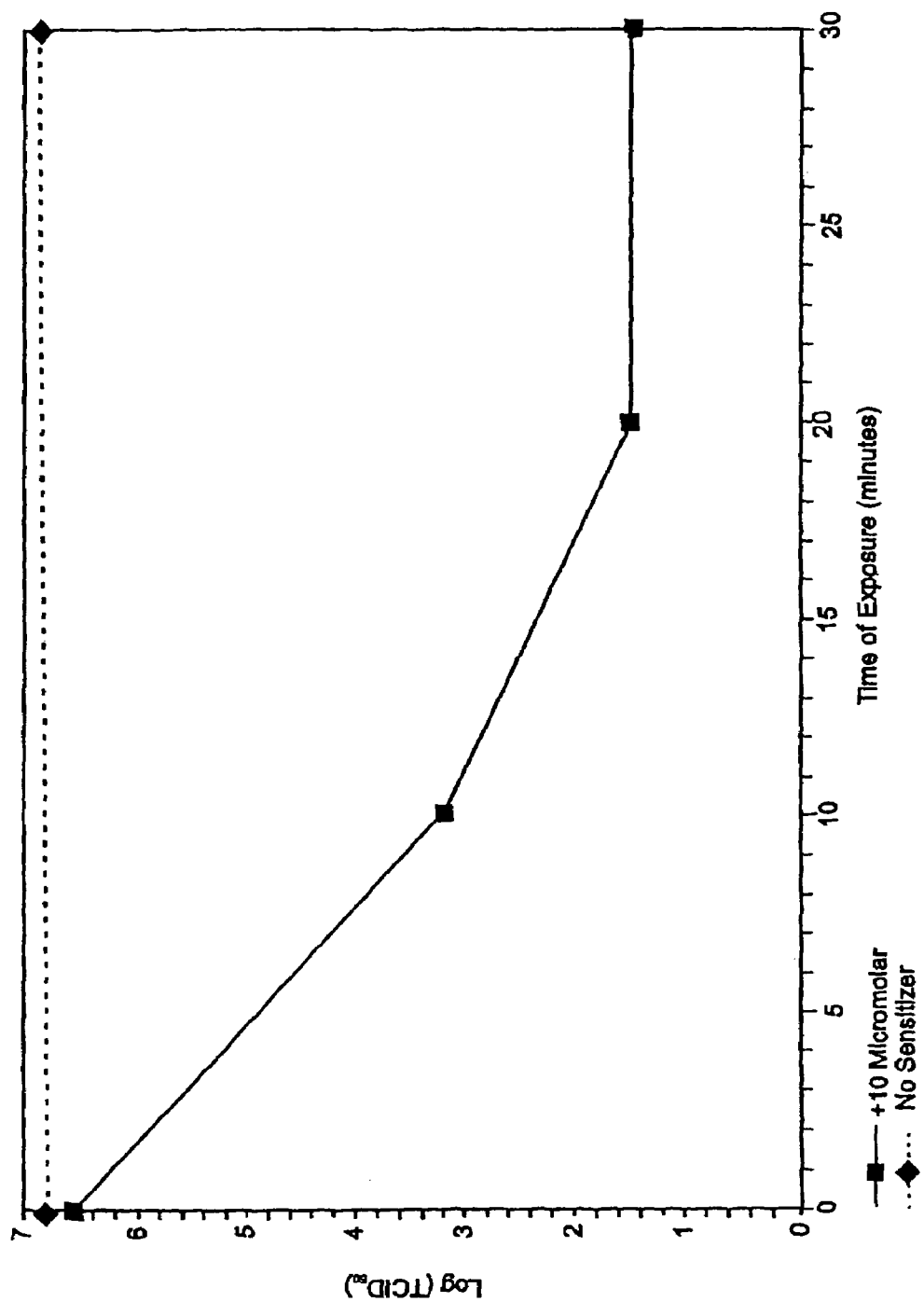
FIG. 18 compares inactivation results with and without sensitizer of vaccinia virus at varying irradiation times.

Samples of platelet concentrate in Isolyte S media 30:70, with and without 10 μM 7,8-dimethyl-10-ribityl-isoalloxazine were spiked with vaccinia virus and irradiated at 60 J/cm² with 50:50 visible:UV light for varying periods of time and inactivation results compared as shown in FIG. 18.

Example 23

To samples of platelet concentrate as described in Example 8 were added 5 μM or 50 μM 7,8-dimethyl-10-ribityl-isoalloxazine. Samples were spiked with HIV 1.

Figure 19:
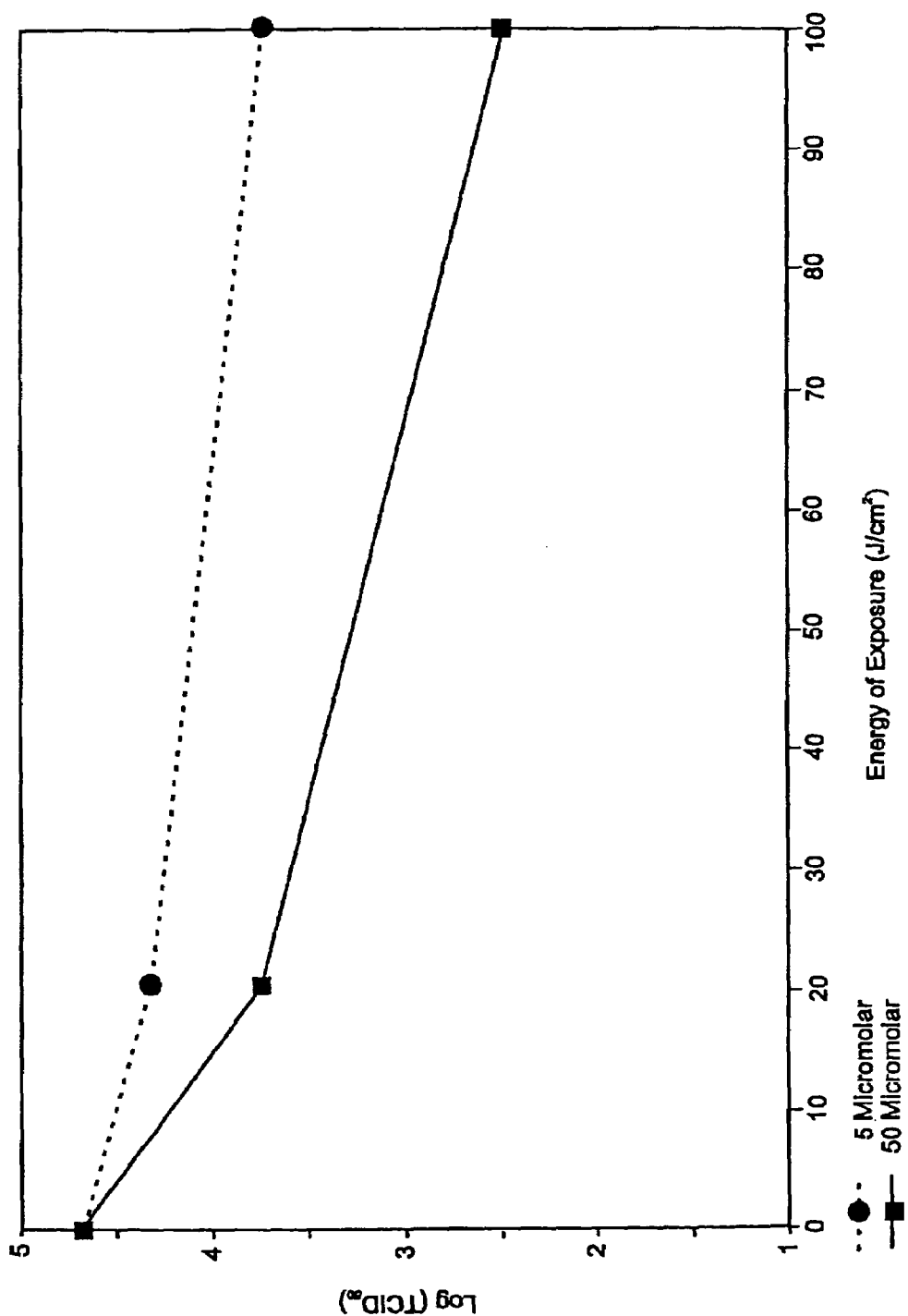
FIG. 19 compares inactivation of extracellular HIV-1 at 5 and 50 μM of photosensitizer and varying irradiation energies.

Using the cuvette flow cell shown in FIG. 7, samples were irradiated with 50:50 visible:UV light at varying energies using an EFOS light system. Inactivation results are show in FIG. 19.

Example 24

Figure 20:
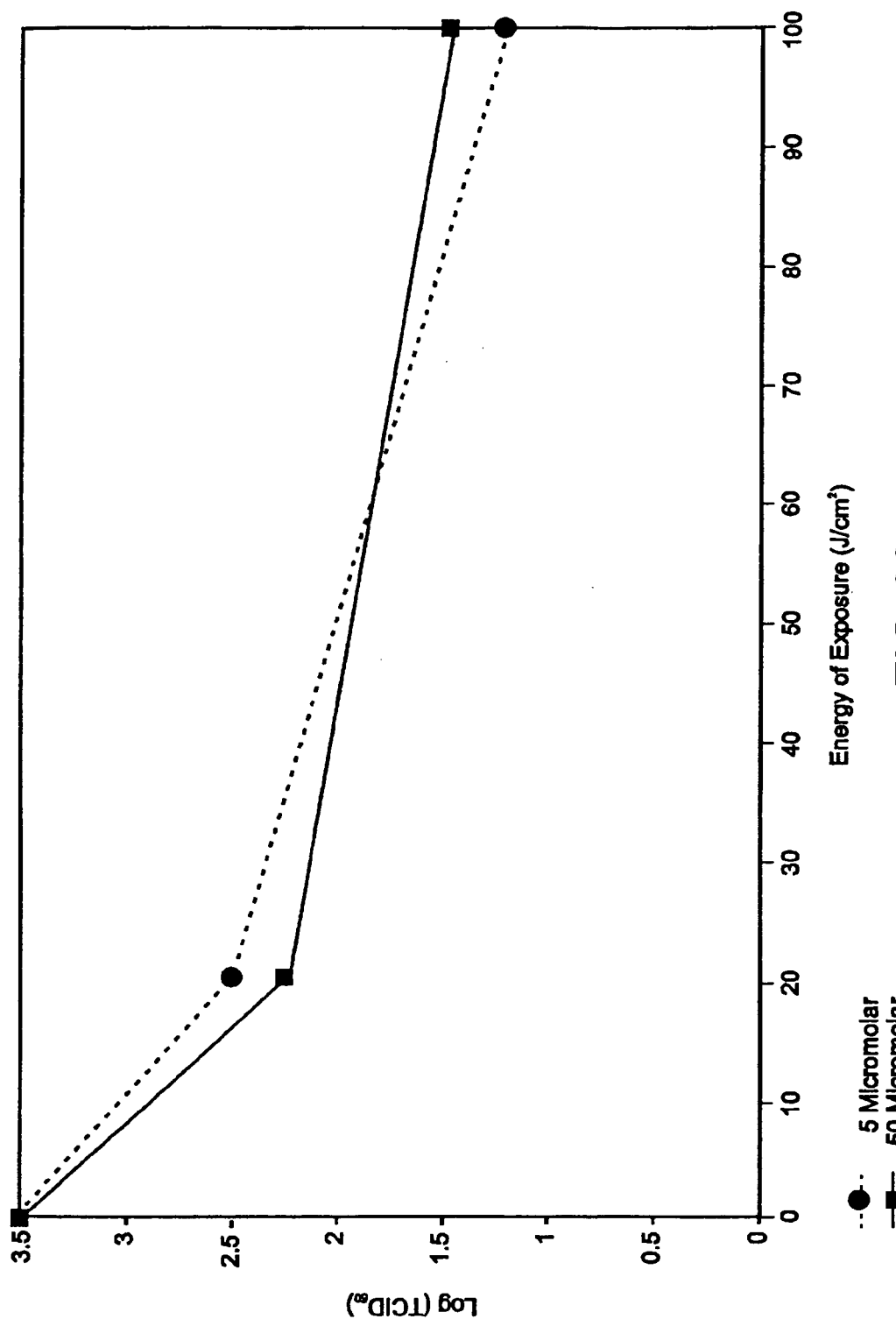
FIG. 20 compares inactivation of intracellular HIV-1 at 5 and 50 μM of photosensitizer and varying irradiation energies.

HIV-infected ACH-2 cells were added to samples of platelet concentrate described in Example 8. 5 or 50 µM of 7,8-dimethyl-10-ribityl-isoalloxazine were added to the samples. The protocol of Example 23 was followed, and inactivation results are shown in FIG. 20. The presence of HIV was assayed by its cytopathic effect on test cells.

Example 25

Figure 21:
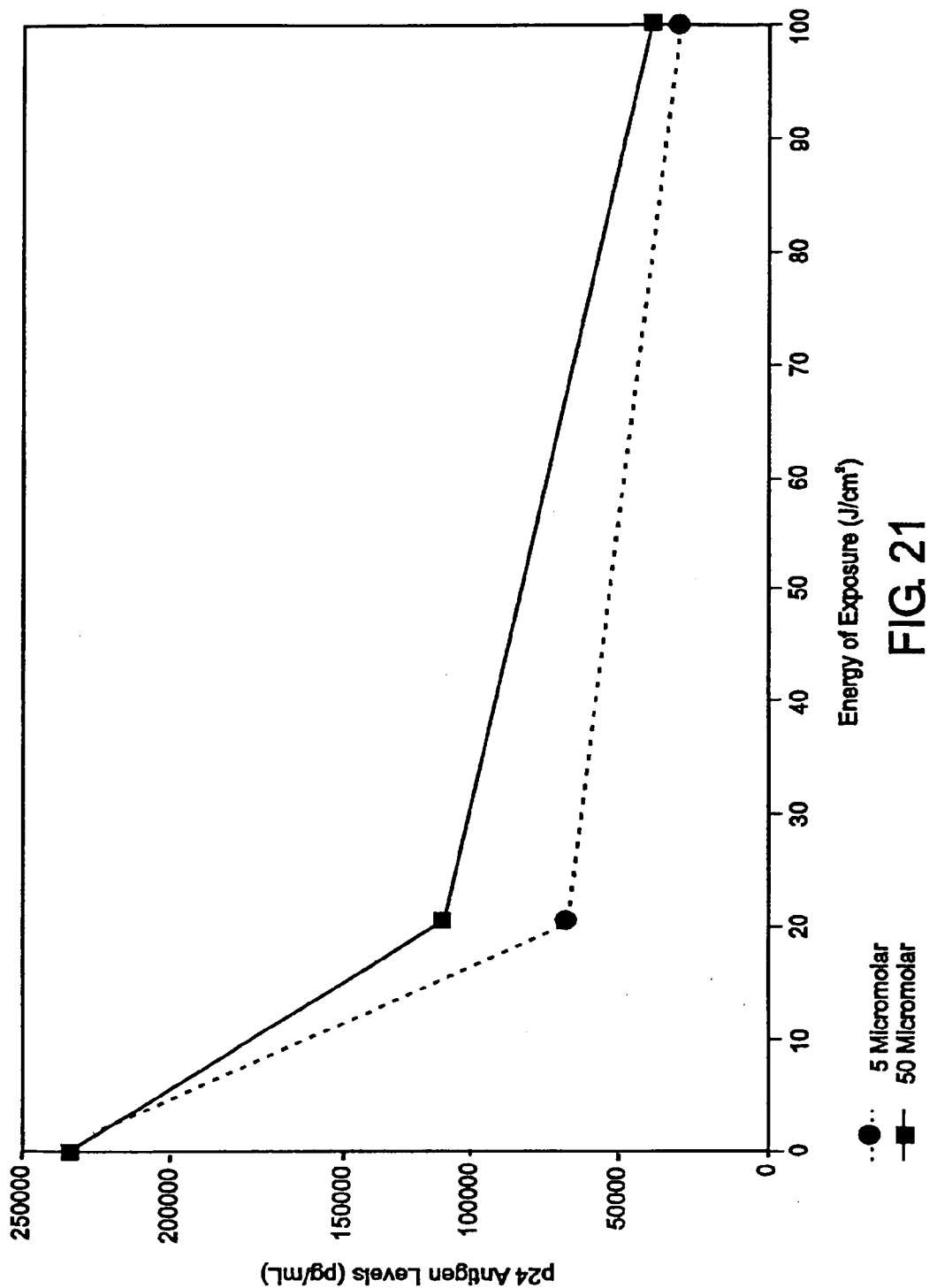
FIG. 21 compares inactivation of intracellular HIV-1 at 5 and 50 μM of photosensitizer and varying irradiation energies, using p24 antigen levels.

The protocol of Example 24 was followed and the presence of HIV assayed by quantifying the level of P24 antigen production. Inactivation results are show in FIG. 21.

Example 26

Figure 22:
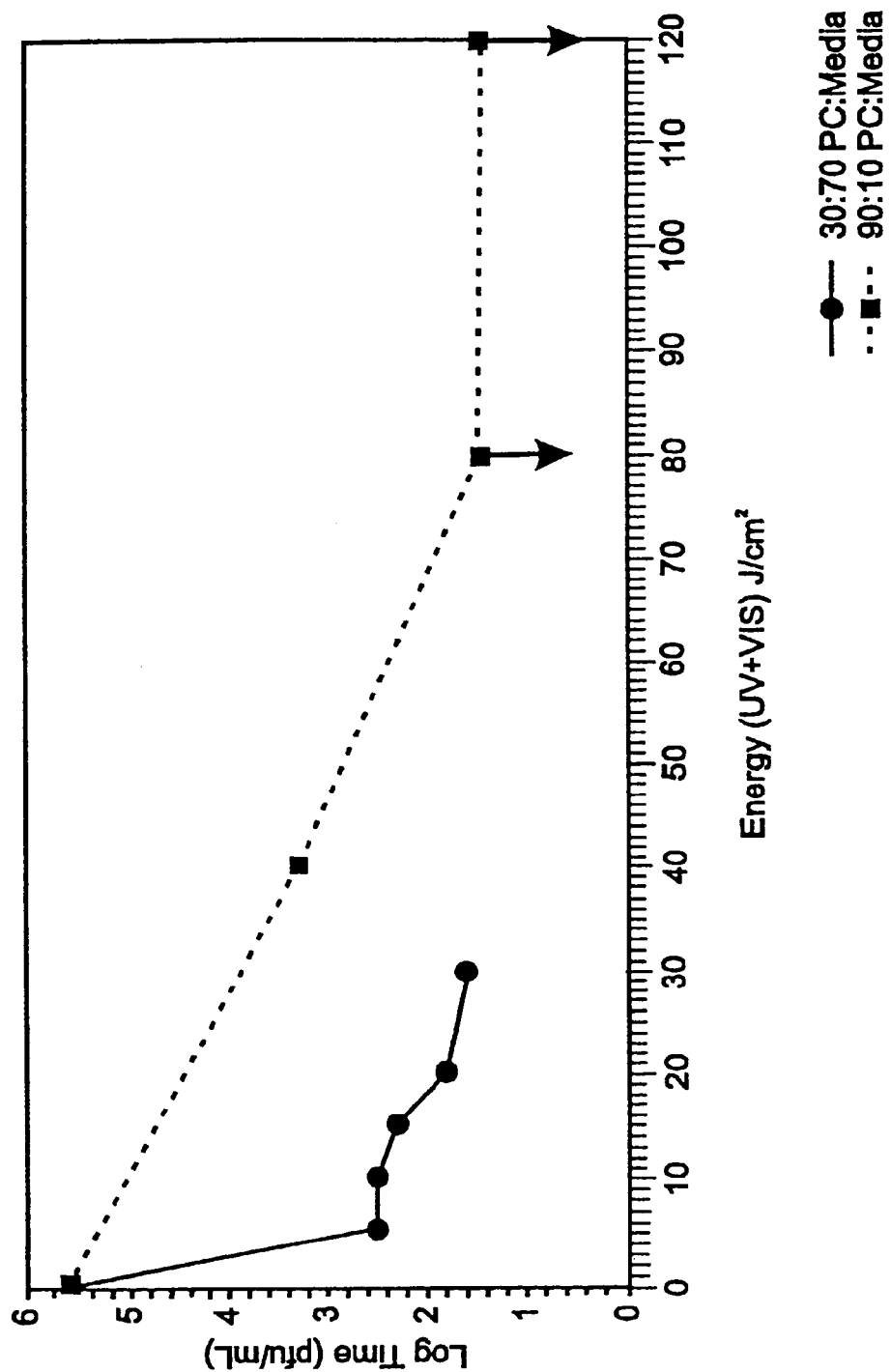
FIG. 22 shows inactivation of HSV-II at varying irradiation levels using platelet concentrate and platelet concentrate in media containing platelet additive solution with ascorbate.

To samples of platelet concentrate as described in Example 8 and media containing 30% platelet concentrate and 70% PASIII™ (Fenwal Labs., Deerfield, Ill.) media were added 6 micromolar ascorbate and 14 µM 7,8-dimethyl-10-ribityl-isoalloxazine. Samples were spiked with HSV-II. Inactivation results are show in FIG. 22 and Table 11.

TABLE 11

| Time (Minutes) | Energy (UV + VIS) J/cm² | 30:70 PC:Media log virus titre | Energy (UV + VIS) J/cm² | 90:10 PC:Media log virus titre |
|---|---|---|---|---|
| 0 | 0 | 5.6 | 0 | 5.6 |
| 1.5 | 5 | 2.5 | 40 | 3.3 |
| 3 | 10 | 2.5 | 80 | 1.5 No Detectable Virus |
| 4.5 | 15 | 2.3 | 120 | 1.5 No Detectable Virus |
| 6 | 20 | 1.8 | | |
| 9 | 30 | 1.6 | | |
| 12 | 40 | | | |
| 24 | 80 | | | |
| 36 | 120 | | | |

Example 27

Inactivation of Phi-6 at Varying Hematocrit Levels of Red Blood Cells

Figure 24:
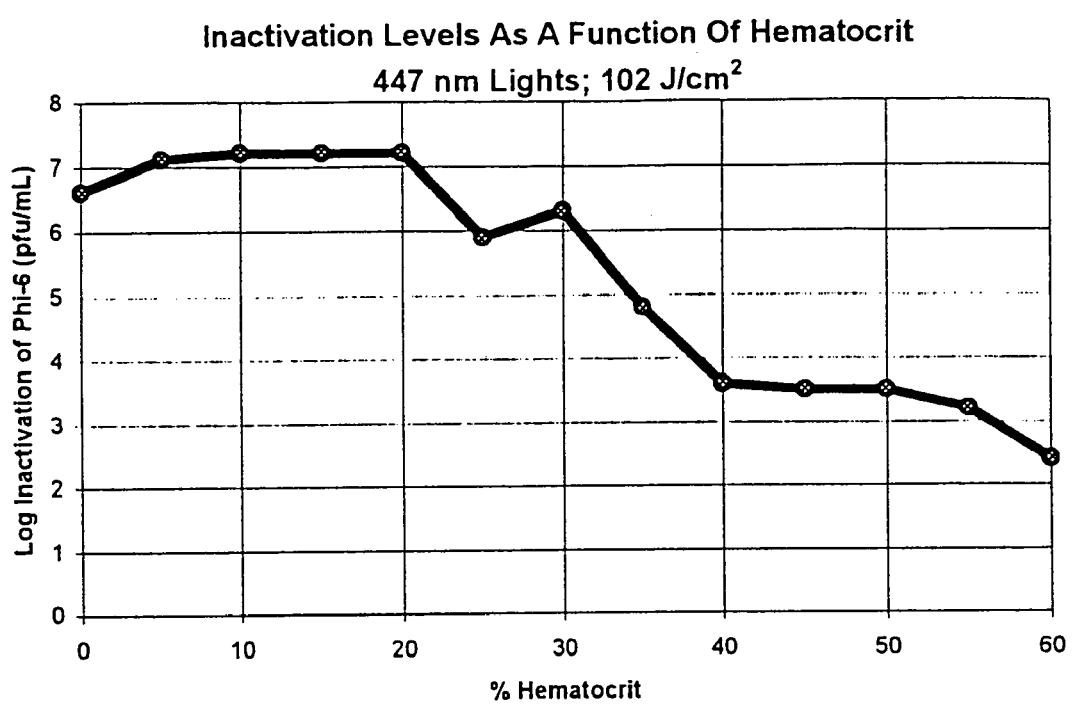
FIG. 24 shows inactivation of Phi-6 (pfu/mL) as a function of hematocrit percent using 447 nm light and 102 J/cm².

Sample Preparation:
Red blood cells were spun out from whole blood to >90% hematocrit, the plasma was removed, and the cells were diluted with 0.9% saline.
Samples of varying hematocrit levels were placed in a Charter Med PVC bag that contained riboflavin sufficient to provide a final concentration of 100 micromolar, spiked with Phi-6 (6 logs/mL or greater) and irradiated with 447 nm lights (Bililights) to provide an applied energy dose of 102 J/cm². The inactivation of Phi-6 as a function of hematocrit is shown in FIG. 24. It is seen that the hematocrit level has a significant effect on the amount of inactivation. Hematocrit levels of less than 40% provide the most inactivation of Phi-6.

Example 28

Inactivation as a Function of Plasma Content for Red Blood Cells

Figure 25:
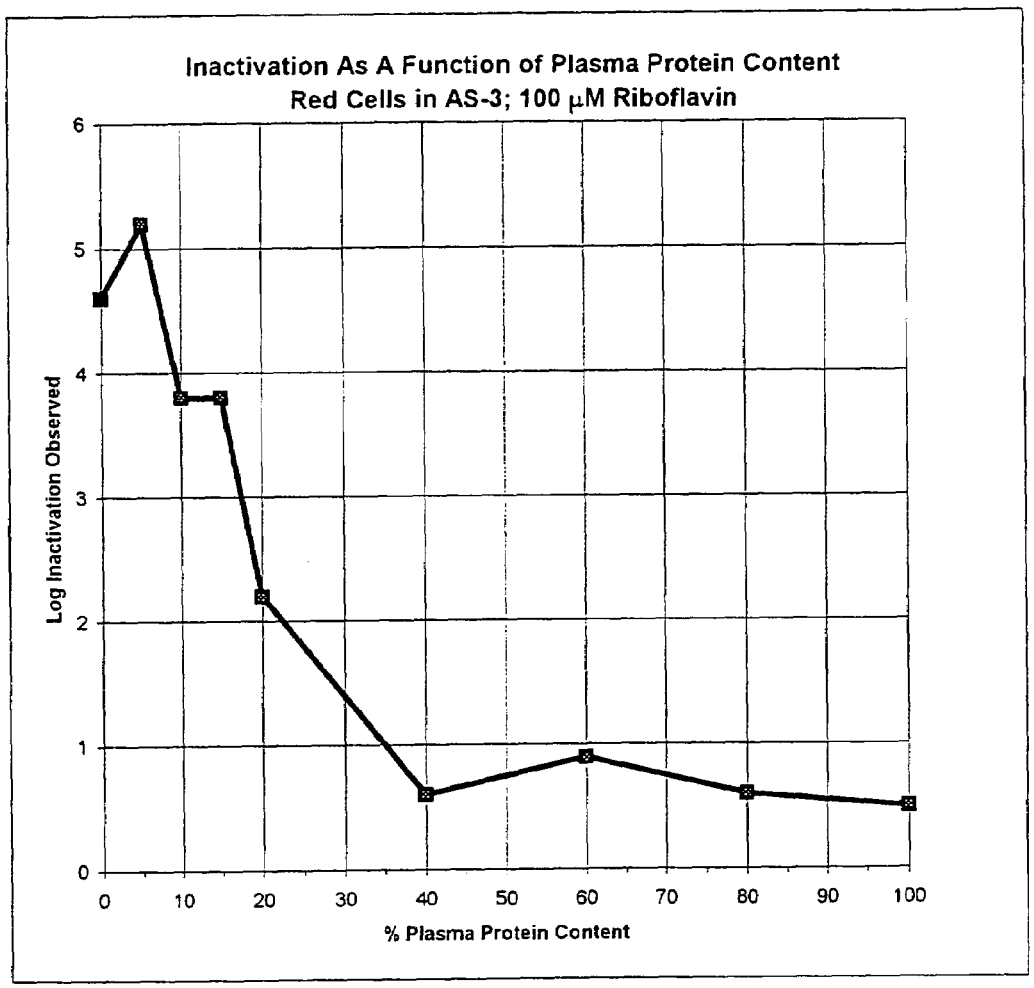
FIG. 25 shows inactivation of Phi-6 as a function of plasma content for red blood cells diluted in AS-3 with a final concentration of 100 micromolar riboflavin with 102 J/cm² 447 nm light.
Figure 26:
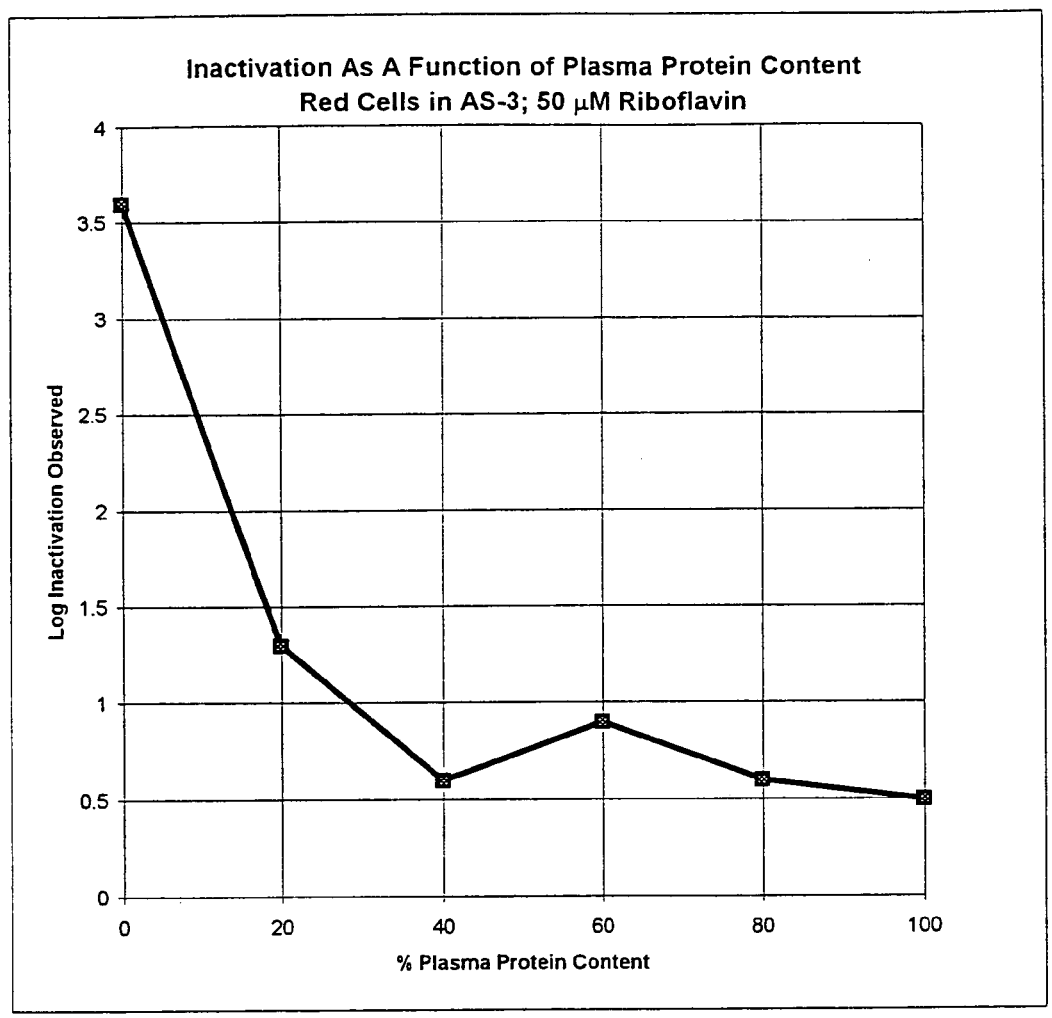
FIG. 26 shows inactivation of Phi-X174 as a function of plasma content for red blood cells diluted in AS-3 with a final concentration of 50 micromolar riboflavin with 102 J/cm² 447 nm light.

The inactivation of Phi-6 and Phi-X174 as a function of plasma content was determined as in Example 27 for red cells suspended in AS-3. 447 nm light was used (Bililights). Results are shown in FIGS. 25 (100 micromolar riboflavin, Phi-6) and 26 (50 micromolar riboflavin, Phi-X174). For both microorganisms, the level of inactivation decreased as the plasma content of the red blood cells increased. Also, a higher concentration of riboflavin increased the level of inactivation seen for all levels of plasma.

Example 29

Figure 27:
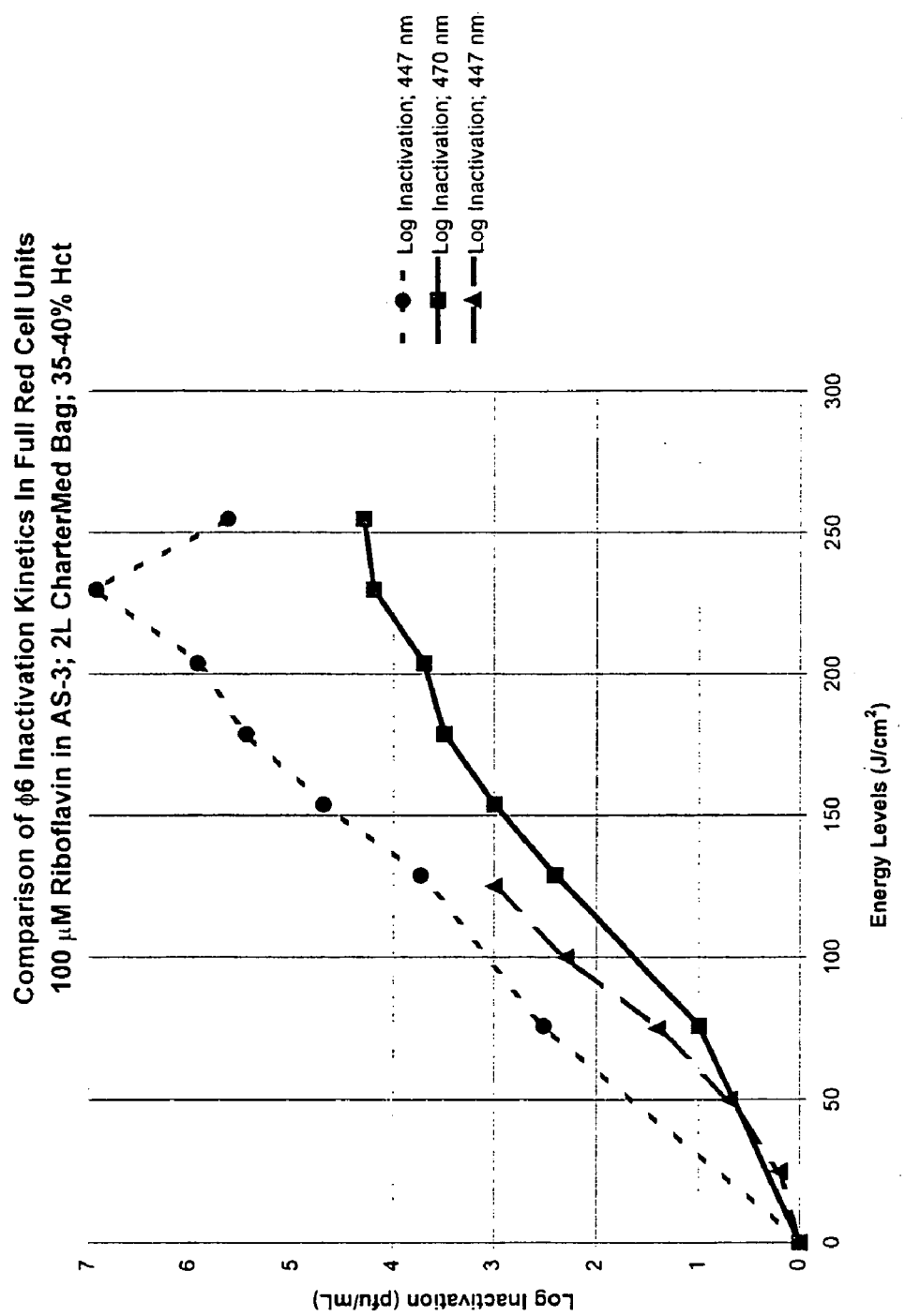
FIG. 27 shows inactivation of Phi-6 as a function of energy of light applied for full red cell units with a hematocrit of 35–40% diluted with AS-3 in a 2 L bag with a final concentration of 100 micromolar riboflavin using 447 or 470 nm light.
Figure 31:
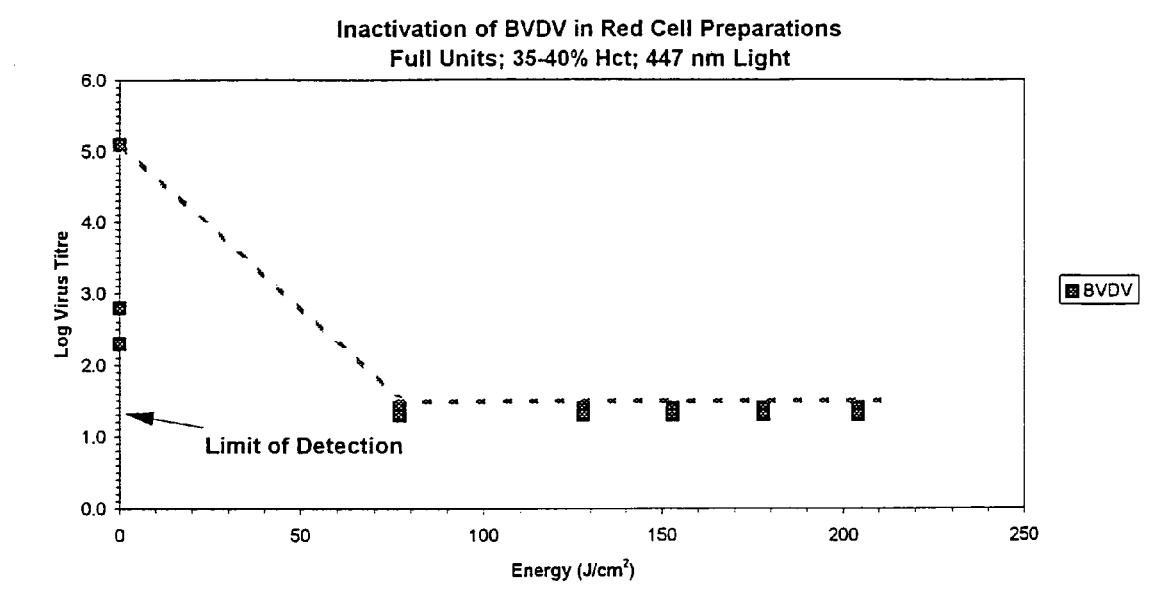

Effect of Energy Applied on the Level of Inactivation of Phi-6 and BVDV in Red Blood Cells The effect that the amount of energy applied to the sample had on the level of inactivation was studied. Samples were prepared as above. Samples were full red cell units prepared at 35–40% hematocrit in AS-3 in a 2L Charter Med Bag, using 100 micromolar riboflavin. Results of the inactivation of Phi-6 are shown in FIG. 27 using 447 (Bililights) and 470 nm (Custom Sea Life) light. Inactivation of BVDV was also studied with 447 nm light. The results for BVDV inactivation are shown in FIG. 31.

Example 30

Effect of Energy Applied at Varying Hematocrit Levels for Inactivation of Phi-6

Figure 28:
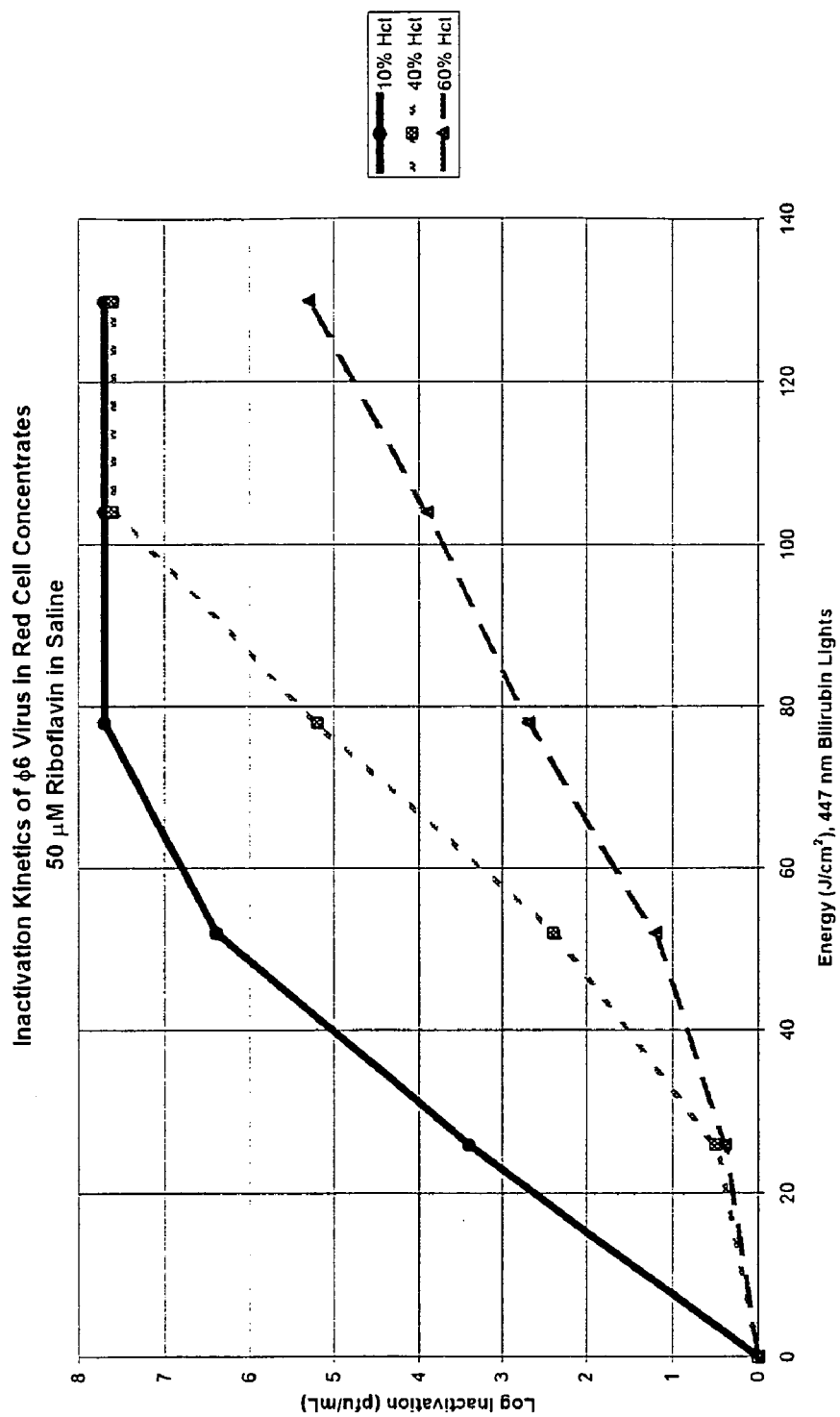
FIG. 28 shows inactivation of Phi-6 using 447 nm lights at hematocrits of 10%, 40% and 60% with increasing energy applied using 50 micromolar riboflavin.

The effect of the energy level applied at different levels of hematocrit (10%, 40% and 60%) for inactivation of Phi-6 was studied. Samples were washed three times in saline with 50 micromolar riboflavin. All samples were 20 ml and were treated in 75 cm² tissue culture flasks. Irradiation was performed from one side with sample mixing with 447 nm bilirubin lights at a flux of 7 mW/cm². Results are shown in FIG. 28. The results indicate that a lower hematocrit gives a faster inactivation at a lower energy level than a higher hematocrit.

Example 31

Kinetics of Inactivation of Phi-6 in Red Blood Cells

Figure 29:
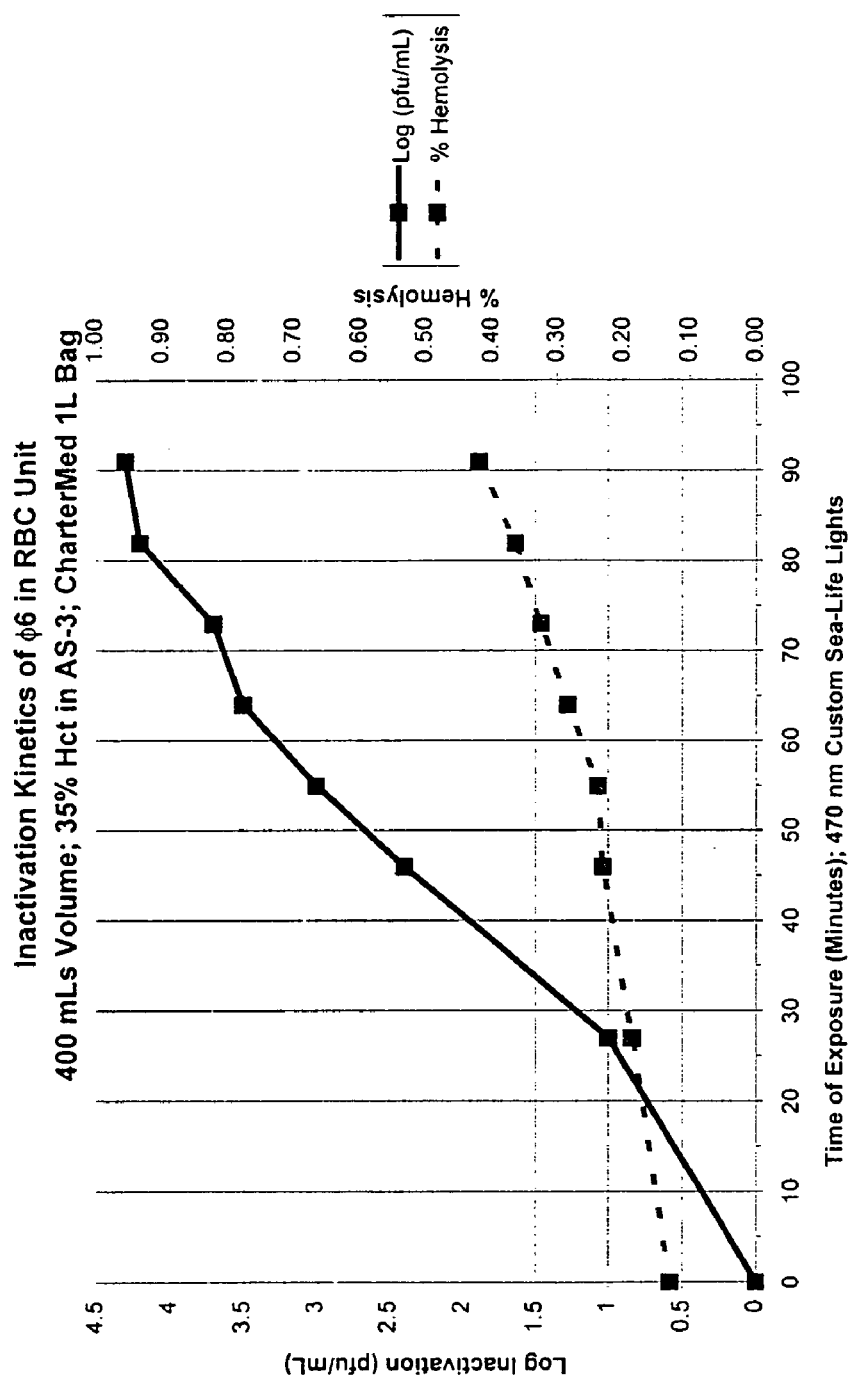
FIG. 29 shows inactivation of Phi-6 in red blood cells with 35% hematocrit diluted in AS-3 and % hemolysis as a function of time of exposure to 470 nm light and 100 micromolar riboflavin.
Figure 30:
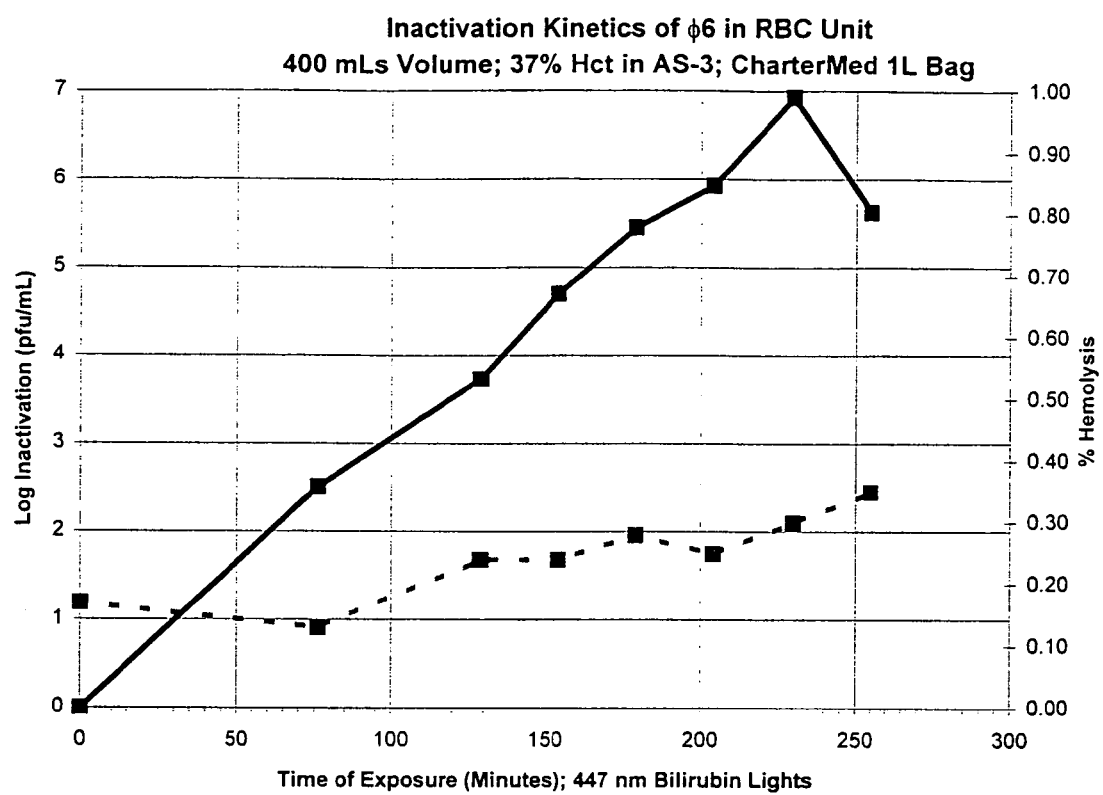
FIG. 30 shows inactivation of Phi-6 in red blood cells with 37% hematocrit diluted in AS-3 and % hemolysis as a function of time of exposure to 447 nm light and 100 micromolar riboflavin.

The kinetics of Phi-6 inactivation were studied using 470 nm and 447 nm light. 35% or 37% hematocrit samples in AS-3 with 400 ml volume were placed in a 1L CharterMed bag. Results are shown in FIGS. 29 (470 µm, 35% hematocrit) and 30 (447 nm, 37% hematocrit). FIGS. 29 and 30 also report the percent hemolysis of the samples as a function of time of exposure.

Example 32

Sample Preparation for Inactivation of Microorganisms in Platelets

Samples of 30 ml platelet volume in B6 sample bags (bags with a 53 ml total volume) were treated with 10 or 20 micromolar riboflavin and 419 nm light and then stored for 7 days. The samples were collected as hyperconcentrates on the SPECTRA™ apparatus and diluted with buffer to a final concentration of 20% of the initial plasma volume.

The buffer was used at a concentration of 20% buffer in 80% RODI water (Reverse Osmosis Deionized water) (pH 7.4) and contained the following:

78.3 mM sodium chloride
5.7 mM potassium chloride
1.7 mM magnesium chloride
34.3 mM sodium acetate
24.6 mM sodium phosphate (dibasic)
5.4 mM sodium phosphate (monobasic)

The plasma concentration may be reduced even further by the use of an appropriate storage solution, such as SETO-sol or other solutions known to those in the art, or developable by those of ordinary skill in the art without undue experimentation. These solutions contain glucose, which may be necessary to provide energy for cellular processes at low plasma concentrations. A lowered protein content would improve the kinetics and cell quality further.

Figure 36:
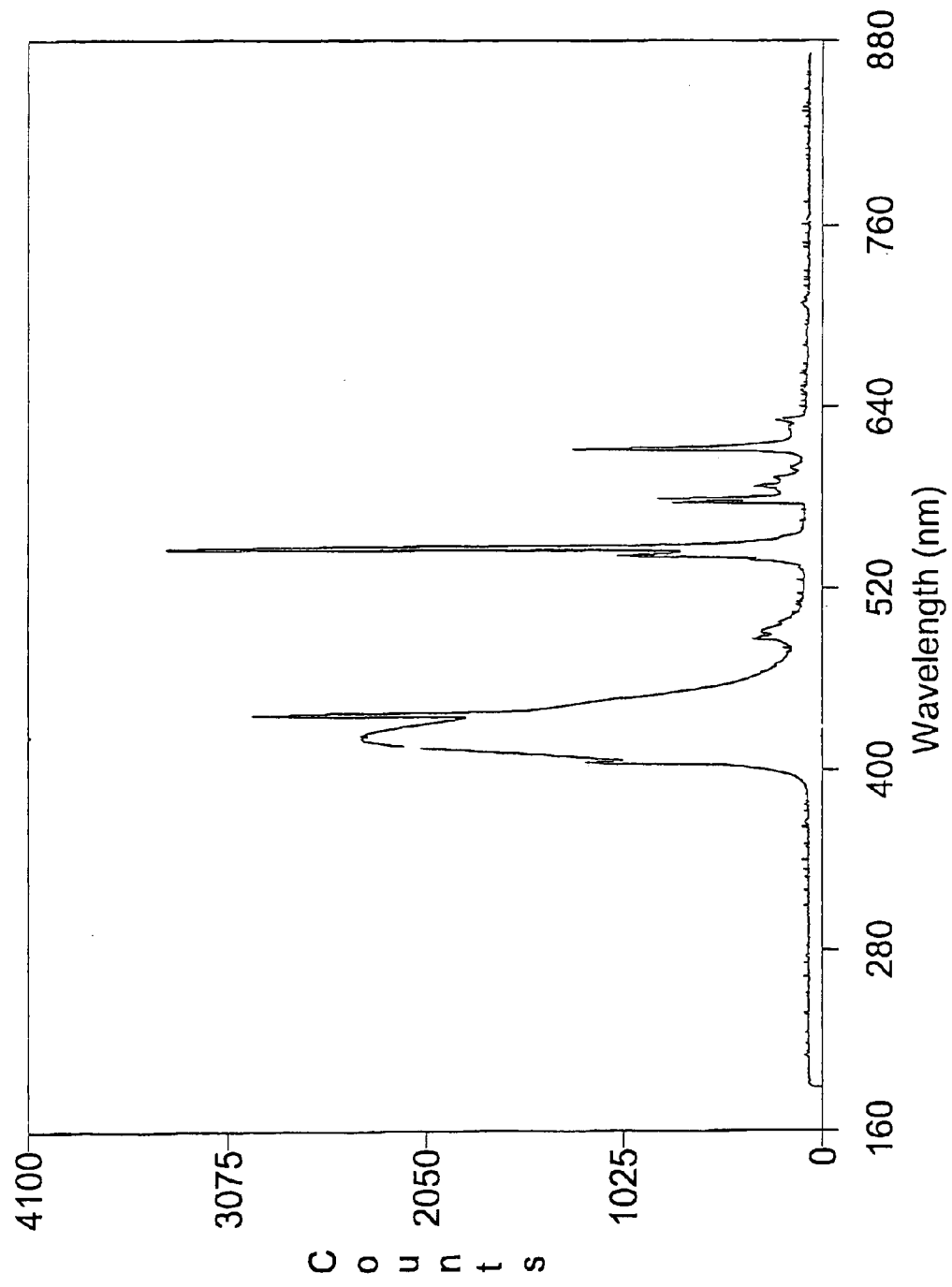
FIG. 36 shows the spectral output for the "420 nm" light used in the experiments.

Light was applied with 420 nm actinic light (output from around 400 nm to around 450 nm, peak at 420 nm, shown in FIG. 36) for 15 minutes to apply 40 J/cm$^2$ and 30 minutes to apply 80 J/cm$^2$.

Example 33

Cell Quality Data for Platelets After Treatment

The procedures described above were used to test the quality of the cells after the treatment with riboflavin and light when the cells were stored for seven days.

Table A shows the HSR (Hypotonic Shock Response) v. Storage time for a control solution (no riboflavin and no exposure to light) and the following samples:
Sample A: control
Sample B: 10 micromolar riboflavin, 40 J/cm$^2$ light
Sample C: 20 micromolar riboflavin, 40 J/cm$^2$ light
Sample D: 10 micromolar riboflavin, 80 J/cm$^2$ light
Sample E: 20 micromolar riboflavin, 80 J/cm$^2$ light Hypotonic shock response is a standard measurement which determines the effect of the treatment on platelet membrane integrity.

Three separate samples were measured for the average values shown in Table 12.

TABLE 12

Hypotonic Shock Response

| Group | Day 1 | Day 3 | Day 5 | Day 7 |
|---|---|---|---|---|
| A avg. | 87.48% | 85.91% | 81.53% | 70.65% |
| A st. dev. | 0.03% | 6.23% | 5.85% | 3.77% |
| B avg. | 84.29% | 80.74% | 77.29% | 63.29% |
| B st. dev. | 9.95% | 1.23% | 2.98% | 12.14% |
| C avg. | 81.80% | 83.45% | 66.75% | 52.38% |
| C st. dev. | 8.27% | 4.18% | 18.02% | 19.06% |
| D avg. | 83.11% | 80.55% | 72.90% | 47.92% |
| D st. dev. | 7.13% | 3.35% | 7.71% | 18.78% |
| E avg. | 77.79% | 68.77% | 51.34% | 28.06% |
| E st. dev. | 5.04% | 12.01% | 23.06% | 21.97% |

Table 12 shows that the average hypotonic shock response decreases over seven days storage time for all solutions. The HSR of samples with a higher concentration of riboflavin added (samples B and D) decreased more over seven days than the solutions with a lower concentration of riboflavin added (samples A and C).

Example 34

Change in pH of Platelet Solution During Storage

Table 13 shows the change in pH of the samples described above, after storage for seven days.

TABLE 13 pH Results

| Day 0 | Day 1 | Day 3 | Day 5 | Day 7 | Group |
|---|---|---|---|---|---|
| 7.26 | 7.22 | 7.24 | 7.28 | 7.27 | A avg. |
| 0.10 | 0.10 | 0.10 | 0.09 | 0.11 | A st. dev. |
| 7.23 | 7.17 | 7.16 | 7.14 | 7.15 | B avg. |
| 0.12 | 0.12 | 0.11 | 0.11 | 0.17 | B st. dev. |
| 7.19 | 7.11 | 7.04 | 6.98 | 7.09 | C avg. |
| 0.10 | 0.12 | 0.15 | 0.19 | 0.21 | C st. dev. |
| 7.21 | 7.16 | 7.15 | 7.04 | 7.16 | D avg. |
| 0.11 | 0.11 | 0.12 | 0.19 | 0.17 | D st. dev. |
| 7.18 | 7.12 | 7.07 | 7.00 | 7.10 | E avg. |
| 0.11 | 0.12 | 0.14 | 0.18 | 0.19 | E st. dev. |

Example 35 pCO$_2$ v. Storage Time for Platelets

Table 14 shows the pCO$_2$ results for the samples described above.

TABLE 14 pCO$_2$ (mm Hg)

| Day 0 | Day 1 | Day 3 | Day 5 | Day 7 | Group |
|---|---|---|---|---|---|
| 8.33 | 10.33 | 10.00 | 8.67 | 8.00 | A avg. |
| 0.58 | 2.08 | 2.00 | 2.08 | 1.00 | A st. DEv. |
| 8.33 | 11.00 | 10.67 | 10.00 | 7.33 | B avg. |
| 2.08 | 2.65 | 2.52 | 2.65 | 2.08 | B st. Dev. |
| 10.00 | 12.33 | 11.67 | 9.00 | 6.00 | C. avg. |
| 1.00 | 1.15 | 1.53 | 1.73 | 1.00 | C st .dev. |
| 9.33 | 11.67 | 11.67 | 13.67 | 9.67 | D avg. |
| 1.15 | 2.31 | 2.52 | 6.66 | 5.51 | D st. dev. |
| 9.67 | 12.00 | 11.67 | 9.00 | 10.00 | E. avg. |
| 1.53 | 1.73 | 2.52 | 2.00 | 8.66 | E st. dev. |

Example 36 pO$_2$ and Cell Count for Platelet Storage

Table 15 shows the pO$_2$ results and cell counts as a function of time for the samples described above. The oxygen consumption was measured using standard tests.

TABLE 15 pO$_2$ Results (mm Hg) and Cell Count Results

| PO$_2$ (mmHg) Day | | | | | | Cell Count Day | | | |
|---|---|---|---|---|---|---|---|---|---|
| 0 | 1 | 3 | 5 | 7 | Group | 1 | 3 | 5 | 7 |
| 77.33 | 73.67 | 81.33 | 98.67 | 101.33 | A av. | 1203.00 | 1214.33 | 1198.00 | 1184.67 |
| 34.27 | 25.50 | 13.80 | 10.97 | 5.86 | A st. dev. | 245.71 | 329.18 | 234.71 | 274.42 |
| 49.33 | 72.67 | 78.67 | 85.67 | 104.33 | B avg. | 1060.67 | 1130.33 | 1128.33 | 1098.00 |
| 8.50 | 24.54 | 18.50 | 23.46 | 10.21 | B st. dev. | 309.81 | 318.53 | 333.38 | 353.06 |
| 57.67 | 68.33 | 75.00 | 92.00 | 113.67 | C avg. | 1204.67 | 1231.67 | 1245.00 | 1109.00 |
| 13.58 | 17.79 | 11.53 | 9.54 | 7.23 | C st. dev. | 208.08 | 223.68 | 192.54 | 142.56 |
| 53.00 | 64.00 | 72.00 | 69.67 | 81.00 | D avg. | 1126.67 | 1150.33 | 1194.67 | 1091.00 |
| 8.72 | 19.67 | 17.35 | 41.02 | 56.31 | D st. dev. | 218.21 | 279.88 | 244.76 | 200.51 |
| 43.67 | 65.33 | 73.33 | 89.00 | 96.67 | E Avg. | 1111.33 | 1128.00 | 1057.67 | 942.33 |
| 7.51 | 22.03 | 16.20 | 20.81 | 62.95 | E st. dev. | 254.23 | 215.09 | 168.17 | 193.78 |

Example 37

GMP-140 Activation in Platelets with Reduced Plasma

Table 16 shows GMP 140 activation as a function of time for the samples described above. GMP-140 is a measure of platelet activation, and is measured by flow cytometry.

TABLE 16

GMP-140 Activation

| Day | | | | |
|---|---|---|---|---|
| 1 | 3 | 5 | 7 | Group |
| 0.18 | 0.28 | 0.29 | 0.40 | A avg. |
| 0.07 | 0.13 | 0.09 | 0.06 | A st. dev. |
| 0.34 | 0.39 | 0.45 | 0.57 | B avg. |
| 0.16 | 0.14 | 0.11 | 0.06 | B st. dev. |
| 0.36 | 0.43 | 0.53 | 0.64 | C avg. |
| 0.07 | 0.06 | 0.07 | 0.01 | C st. dev. |
| 0.33 | 0.43 | 0.51 | 0.66 | D avg. |
| 0.12 | 0.10 | 0.06 | 0.03 | D st. dev. |
| 0.43 | 0.54 | 0.65 | 0.77 | E avg. |
| 0.11 | 0.06 | 0.04 | 0.07 | E st. dev. |

Example 38

Swirl Results

The platelet swirl was also tested. Table 17 shows the change in swirl results for the samples described above. In Table 17, the swirl scale where a value of 3 indicates a ++platelet swirl, a value of 2 indicates a +platelet swirl, a value of 1 indicates a +/−platelet swirl, and a value of 0 indicates a −platelet swirl is used.

Table 17 indicates that a 10 micromolar riboflavin and 20 J/cm$^2$ treatment does not affect that platelet swirl over seven days, whereas a treatment with 20 micromolar riboflavin and 40 J/cm$^2$ decreases the platelet swirl to 2 over seven days. None of the samples experienced a decrease in platelet swirl score after three days.

TABLE 17

Swirl Results

| Day | | | | | |
|---|---|---|---|---|---|
| 0 | 1 | 3 | 5 | 7 | Group |
| 3.00 | 3.00 | 3.00 | 3.00 | 3.00 | A avg. |
| 0.00 | 0.00 | 0.00 | 0.00 | 0.00 | A st. dev. |
| 3.00 | 3.00 | 3.00 | 3.00 | 3.00 | B avg. |
| 0.00 | 0.00 | 0.00 | 0.00 | 0.00 | B st. dev. |
| 3.00 | 3.00 | 3.00 | 2.67 | 2.67 | C avg. |
| 0.00 | 0.00 | 0.00 | 0.58 | 0.58 | C st. dev. |
| 3.00 | 3.00 | 3.00 | 3.00 | 2.33 | D avg. |
| 0.00 | 0.00 | 0.00 | 0.00 | 1.15 | D st. dev. |
| 3.00 | 3.00 | 3.00 | 2.67 | 2.00 | E avg. |
| 0.00 | 0.00 | 0.00 | 0.58 | 0.00 | E st. dev. |

Example 39

Lactate Results as a Function of Time for Platelet Sample with Reduced Plasma

Table 18 shows the lactate concentration as a function of time for the samples described above. Generation of lactate is a measure of anaerobic metabolism. All samples, including the control sample, experienced an increase in the lactate concentration over seven days storage.

TABLE 18

Lactate (mmol/L)

| | Day | | | |
|---|---|---|---|---|
| Group | 1 | 3 | 5 | 7 |
| A av. | 2.00 | 3.41 | 5.30 | 7.86 |
| A st. dev. | 0.26 | 0.39 | 0.93 | 1.39 |
| B avg. | 2.55 | 4.50 | 7.19 | 9.48 |
| B st. dev. | 0.54 | 1.03 | 1.55 | 3.03 |
| C avg. | 3.80 | 7.28 | 10.90 | 11.22 |
| C st. dev. | 0.53 | 1.75 | 2.60 | 2.56 |
| D avg. | 2.58 | 4.54 | 8.78 | 10.09 |
| D st. dev. | 0.42 | 0.92 | 2.58 | 2.82 |
| E avg. | 3.21 | 5.93 | 9.46 | 9.02 |
| E st. dev. | 0.55 | 1.31 | 2.38 | 3.51 |

Example 40

Morphology of Platelets

Table 19 shows the change in morphology score as a function of time for the samples described above.

TABLE 19

| \multicolumn{4}{c|}{Morphology Score} | |
| Day | | | | |
| 1 | 3 | 5 | 7 | Group |
|---|---|---|---|---|
| 259.00 | 230.00 | 223.33 | 224.67 | A avg. |
| 3.46 | 10.58 | 2.31 | 11.93 | A st. dev. |
| 242.67 | 215.67 | 224.67 | 210.00 | B avg. |
| 26.54 | 26.31 | 6.51 | 19.47 | B st. dev. |
| 233.33 | 219.67 | 218.67 | 211.67 | C avg. |
| 11.02 | 12.06 | 20.98 | 29.84 | C st. dev. |
| 231.67 | 216.33 | 224.00 | 218.33 | D avg. |
| 20.55 | 30.27 | 3.00 | 11.93 | D st. dev. |
| 230.67 | 220.67 | 220.33 | 203.67 | E avg. |
| 5.13 | 12.34 | 20.65 | 10.97 | E st. dev. |

Example 41

Inactivation of BVDV Virus in Platelets with Reduced Plasma

To the samples described above, BVDV virus was added before addition of riboflavin and before exposure to 419 nm light. The starting titre of the BVDV was 4.3 or 3.9 (zero values). The inactivation of the virus was studied as a function of riboflavin concentration added and light applied. The BVDV virus is used as a model for Hepatitis C. At 40 J/cm$^2$, complete kill is seen (the sensitivity of the test is 1.3 logs).

The average results for three separate samples at each treatment combination are shown below.

TABLE 20

BVDV Inactivation as a function of energy for 10 and 20 micromolar riboflavin

| Energy (J/cm$^2$) | 10 micromolar riboflavin | | 20 micromolar riboflavin | |
|---|---|---|---|---|
| | Avg. | Std. Dev. | Avg. | Std. Dev. |
| 0 | 4.3 | 0.1 | 3.9 | 0.5 |
| 40 | ≦1.4 | 0.2 | ≦1.4 | 0.2 |
| 80 | ≦1.3 | 0.0 | ≦1.3 | 0.0 |

Example 42

Plasma Preparation

For studies of plasma proteins, either stericon bags, CharterMed bags, or tissue culture flasks were used. Light was delivered with a Dymax Source (365, 419, 447 nm). Plasma protein factor activity levels were determined by standard protein activity assays.

Example 43

The Effect of Air on Microorganism Inactivation in Plasma

Figure 32:
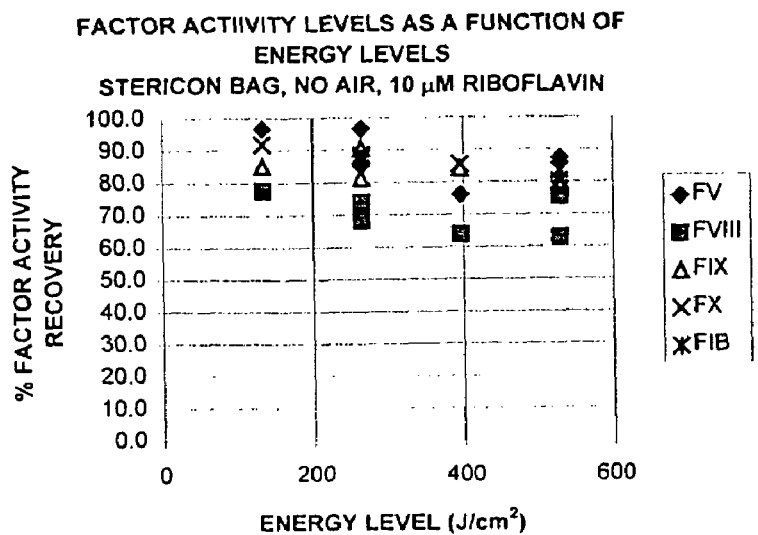
FIG. 32 shows protein factor activity levels as a function of energy levels using a stericon bag, no air, with 10 micromolar riboflavin.
Figure 33:
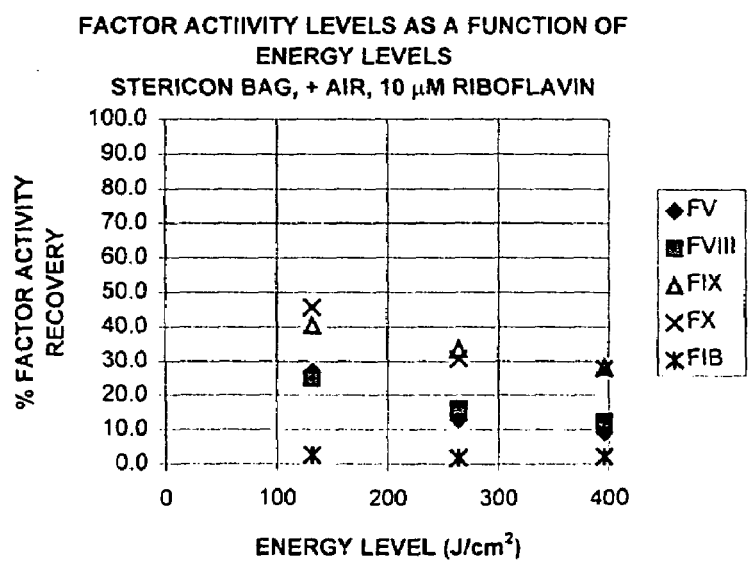
FIG. 33 shows protein factor activity levels as a function of energy levels using a stericon bag with air and 10 micromolar riboflavin.
Figure 34:
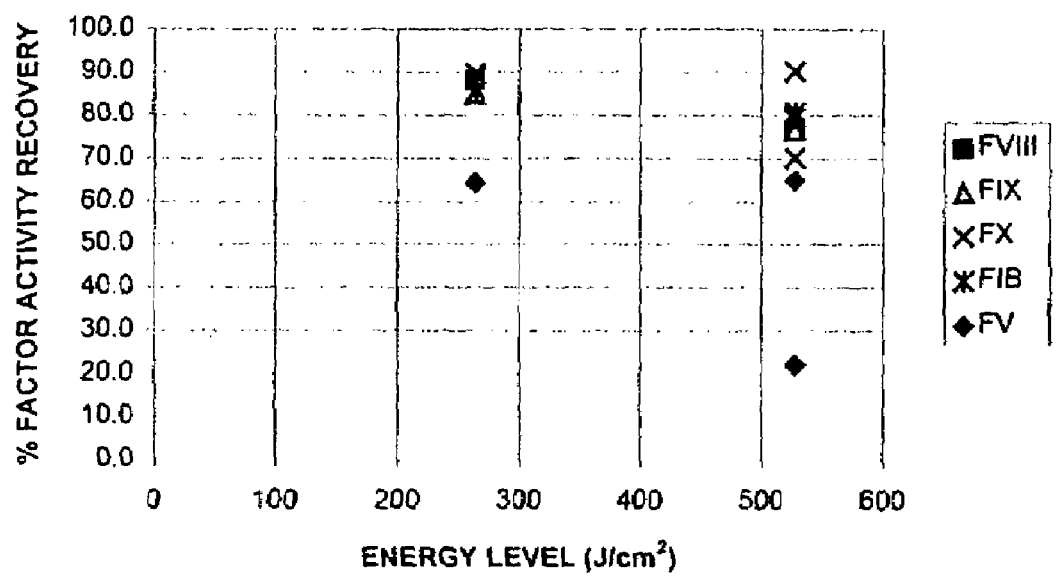
FIG. 34 shows protein factor activity levels as a function of energy levels using a stericon bag with air, 10 micromolar ascorbate and 10 micromolar riboflavin.

The amount of the inactivation of the microorganism S. epidermidis using 10 micromolar riboflavin is not dependent on the presence of air in a sample of 18 ml plasma and 2 ml riboflavin solution (unreported results), but air has a significant effect on the amount of protein damage that occurs upon irradiation. FIGS. 32 and 33 compare the protein factor activity recovery levels as a function of energy level of a sample treated in a stericon bag with 10 mm riboflavin. When ascorbate is added, the effect of air degradation is decreased (see FIG. 34).

Shown in Table 21 is the percentage recovery of various proteins treated with 3 micromolar methylene blue with 43 J/cm$^2$ light applied with a sodium arc lamp. The data is from Transfusion (1998) 38: Abstract S239.

TABLE 21

| | Methylene Blue |
|---|---|
| Protein | % Recovery |
| Factor II | 93 |
| Factor V | 88 |
| Factor VII | 98 |
| Factor VIII | 76 |
| Factor IX | 84 |
| Factor X | 93 |
| Factor XI | 69 |
| Factor XII | — |
| Protein C | 96 |
| Protein S | 117 |
| Fibrinogen | 71 |

Example 44

Plasma Protein Studies

Table 22 µsummarizes various plasma protein treatments using ascorbate in the buffer. These experiments were performed in tissue culture flasks that contain air.

Sample A was a 90% plasma/10% media formulation in CAS II-2. 80 J/cm$^2$ of light (40 J/cm$^2$ UVA) was applied to sample A with a DYMAX 2000 irradiator. Sample B was a 90% plamsa/10% media formulation in CAS II-2. 105 J/cm$^2$ of light (53 J/cm$^2$ UVA) was applied to sample B with a DYMAX 2000 irradiator.

The CAS II-2 buffer formulation used had 139 mM sodium phosphate dibasic, 43 mM sodium phosphate monobasic, 100 micromolar riboflavin and 100 mM sodium ascorbate. These values were reduced by a factor of 10 after mixing with the plasma. The pH of the buffer before mixing with plasma was 7.4. The pH of the solution after mixing the buffer and plasma was 7.2.

Samples C and D were a 90% plasma/10% media formulation. The media was 100 micromolar riboflavin in 0.9% saline with final concentration of ascorbate of 10 micromolar. The pH of the media was initially 5.0, and the pH after mixing with plasma was 7.0. After mixing the media and plasma, the riboflavin concentration was 10 micromolar. 103 J/cm$^2$ of light was applied (30 J/Cm$^2$ UVA was applied) with a UVP irradiator (365 nm and 419 nm).

TABLE 22

Plasma Protein Studies

| Protein | A<br>% Activity Pre-Treatment | B<br>% Activity Pre-Treatment | C<br>% Activity Pre-Treatment | D<br>% Activity Pre-Treatment | Average | STD DEV | Normal Adult Ranges |
|---|---|---|---|---|---|---|---|
| Factor II | 86 | 88 | 67 | 73 | 78.3 | 9.9 | 75.0–135.0 |
| Factor V | 56 | 80 | 69 | 66 | 67.8 | 9.9 | 70.0–150.0 |
| Factor VII | 81 | 49 | 57 | 73 | 65.0 | 14.6 | 50.0–155.0 |
| Factor VIII | 96 | 123 | 77 | 35 | 82.8 | 37.0 | 50.0–155.0 |
| Factor IX | 78 | 80 | 77 | 67 | 75.5 | 5.8 | 60–150.0 |
| Factor X | 83 | 71 | 71 | 67 | 73.0 | 6.9 | 65.0–135.0 |
| Factor XI | 83 | 78 | 85 | 58 | 76.0 | 12.4 | 60.0–150.0 |
| Factor XII | 81 | 38 | 50 | 41 | 52.5 | 19.7 | 50.0–150.0 |
| APTT | | | 32.4 | 40.6 | 36.5 | 5.8 | 24.0–36.0 |
| Fibrinogen | | | 227 | 212 | 219.5 | 10-.6 | 160.0–350.0 |
| Euglobulin Lysis Time | | | 5.0 | 6.5 | 5.8 | 1.1 | 2.0–10.0 |
| Plasminogen | | | 86 | 71 | 78.5 | 10.6 | 65.0–150.0 |
| Antithrombin | | | 59 | 62 | 60.5 | 2.1 | 70.0–130.0 |
| Protein C. Antigen | | | 77 | 79 | 78.0 | 1.4 | 60.0–150.0 |
| Protein C Activity | | | 58 | 68 | 63.0 | 7.1 | 55.0–140.0 |
| Protein S. Antigen | | | 81 | 83 | 82.0 | 1.4 | 60.0–150.0 |
| Protein S. Activity (Clot) | | | 82 | 85 | 83.5 | 2.1 | 50.0–140.0 |
| APC Resistance + FV Def. | | | 2.8 | 2.9 | 2.9 | 0.1 | 2.20–4.00 |

| Protein | % Activity Post-Treatment | % Activity Post-Treatment | % Activity Post-Treatment | % Activity Post-Treatment | Average | STD DEV | % Recovery |
|---|---|---|---|---|---|---|---|
| Factor II | 71 | 76 | 58 | 60 | 66.2 | 8.7 | 84.6 |
| Factor V | 49 | 61 | 49 | 49 | 52.0 | 6.0 | 76.7 |
| Factor VII | 75 | 45 | 49 | 61 | 57.5 | 13.5 | 88.4 |
| Factor VIII | 80 | 117 | 67 | 30 | 73.4 | 35.9 | 88.7 |
| Factor IX | 64 | 70 | 62 | 63 | 64.8 | 3.5 | 85.8 |
| Factor X | 78 | 64 | 60 | 56 | 64.5 | 9.6 | 88.4 |
| Factor XI | 84 | 70 | 81 | 58 | 73.3 | 11.8 | 96.4 |
| Factor XII | 76 | 34 | 49 | 43 | 50.5 | 18.1 | 96.1 |
| APTT | | | 39 | 43 | 40.8 | 2.5 | |
| Fibrinogen | | | 191 | 185 | 188.1 | 4.3 | 85.7 |
| Euglobulin Lysis Time | | | 5.8 | 5.8 | 5.8 | 0.0 | 100.0 |
| Plasminogen | | | 81 | 68 | 74.6 | 9.3 | 95.0 |
| Antithrombin | | | 56 | 65 | 60.3 | 6.7 | 99.6 |
| Protein C. Antigen | | | 78 | 65 | 71.4 | 9.0 | 91.5 |
| Protein C Activity | | | 53 | 63 | 58.2 | 6.8 | 92.3 |
| Protein S. Antigen | | | 72 | 74 | 73.1 | 1.3 | 89.2 |
| Protein S. Activity (Clot) | | | 90.0 | 96.0 | 93.0 | 4.2 | 111.4 |
| APC Resistance + FV Def. | | | 2.9 | 2.7 | 2.8 | 0.1 | 98.1 |

When ascorbate was not added to samples C and D, the percent recovery decreased (data not shown). This effect was particularly pronounced for Factors V, VIII. IX, X and Fibrinogen.

Table 23 shows plasma protein recovery in samples (in charter Med IL bags) with and without air and with and without ascorbate (ASC). The table shows that a significant amount of protein damage occurs when air is present in the samples. If air is present, the addition of ascorbate assists in minimizing the extent of protein damage.

TABLE 23

Plasma Studies

| | FV | FVIII | FIX | FX | FIB | Energy |
|---|---|---|---|---|---|---|
| No Air | 96.7 | 77.5 | 85.1 | 91.7 | 109.3 | 132 |
| No Air | 96.7 | 73.9 | 90.4 | 88.1 | 105.5 | 264 |
| No Air | 76.0 | 63.8 | 84.0 | 85.3 | 105.9 | 396 |
| No Air | 85.2 | 68.3 | 81.3 | 88.4 | 87.3 | 264 |
| No Air | 76.7 | 62.9 | 78.4 | 80.0 | 83.3 | 528 |
| No Air | 87.3 | 75.4 | 80.0 | 77.3 | 90.2 | 528 |
| +Air | 13.0 | 16.1 | 33.3 | 30.7 | 1.7 | 264 |
| +Air | 26.9 | 24.8 | 40.4 | 45.5 | 2.5 | 132 |
| +Air | 9.3 | 12.4 | 28.3 | 27.7 | 2.1 | 396 |
| Flask | 11.2 | 13.6 | 32.0 | 30.6 | 2.2 | 132 |

TABLE 23-continued

Plasma Studies

| | FV | FVIII | FIX | FX | FIB | Energy |
|---|---|---|---|---|---|---|
| +Air + 1 mM ASC | 51.5 | 14.4 | 64.6 | 64.4 | 33.4 | 132 |
| | 24.5 | 13.5 | 40.2 | 43.7 | 1.3 | 264 |
| | 18.4 | 13.5 | 34.1 | 38.8 | 1.6 | 396 |
| +Air + 10 mM ASC | 64.4 | 88.2 | 84.9 | 85.5 | 89.6 | 264 |
| | 22.2 | 76.9 | 77.0 | 80.7 | 70.2 | 528 |
| | 65.0 | 80.4 | 76.6 | 79.5 | 90.2 | 528 |

Example 45

Effect of Container Size on Inactivation of Phi-6 in Plasma

The effect of Phi-6 inactivation in different sized containers was also studied. 250 ml plasma with 10 micromolar riboflavin was added to either a 2L CharterMed, a 2L Stericon bag or a IL stericon bag. The pathogen in the IL bags was not inactivated to as great an extent as the pathogen in the 2L bags.

Example 46

Inactivation of Porcine Parvo in Plasma

Porcine parvo is similar to a human virus (parvovirus B19) that is hard to detect and remove or inactivate in blood components. Also, parvo is very hard to inactivate using existing methods of microorganism inactivation. To test the effect of removing part of the plasma on the ability of riboflavin to inactivate parvo, samples of plasma containing ≧6 logs/mL (concentration) of parvo virus were diluted in saline to a final concentration of 20% or less plasma. 10 or 50 micromolar riboflavin was added, and the samples irradiated with 365+419+447 nm (Dymax Source) light for 30 or 60 minutes. Under these conditions, 6 logs of kill were seen.

TABLE 24

| % Plasma Content | 30 Minutes | | 60 Minutes | |
|---|---|---|---|---|
| | 10 Micromolar | 50 Micromolar | 10 Micromolar | 50 Micromolar |
| 0 | 6.4 | 6.5 | 6.5 | 6.5 |
| 5 | 6.5 | 6.5 | 6.0 | 5.8 |
| 10 | 6.5 | 6.5 | 5.4 | 4.7 |
| 15 | 2.7 | 6.5 | 4.4 | 3.0 |
| 20 | 2.0 | 4.5 | 3.3 | 2.2 |

Figure 35:
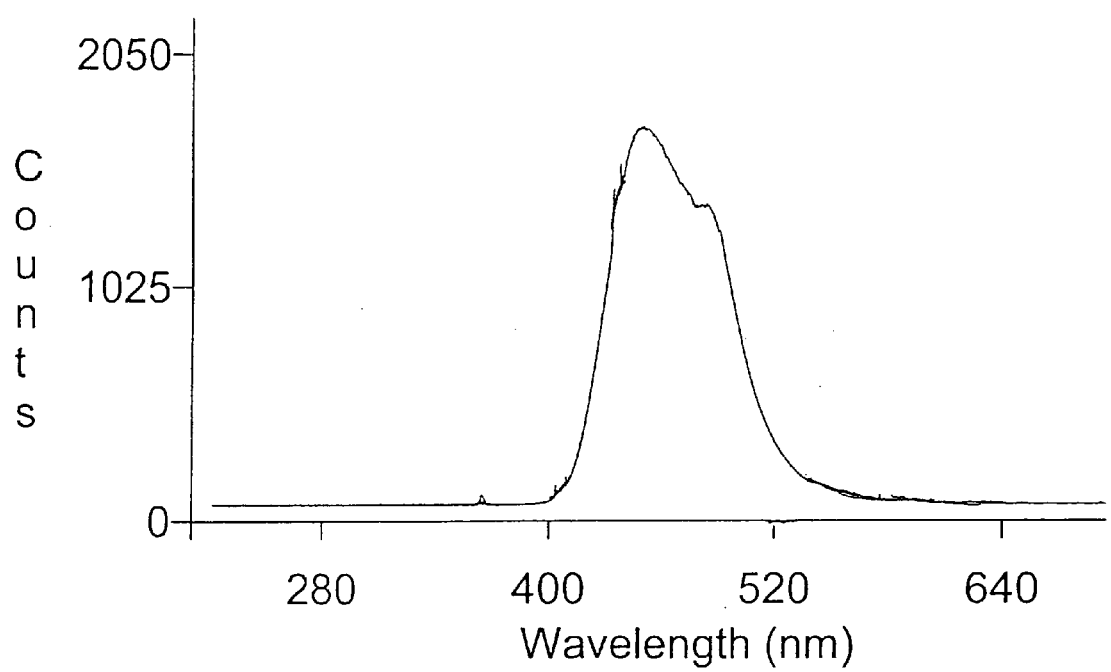
FIG. 35 shows the spectral output for the "470 nm" light used in the experiments.

It should be understood that the light source described as "470 nm" used in these experiments has a broad spectral output from around 400–520 nm. The spectral output is shown in FIG. 35. This light was from Custom Sea Life, and was a 7100 K Blue 28 watt Twin Tube. "419 nm" light was provided by Super Actinic Lights with spectral output shown in FIG. 36. "447 nm" light was typically provided from a bililight source. Other sources of radiation may be used, as long as they provide suitable wavelengths and intensities.

It will be readily understood by those skilled in the art that the foregoing description has been for purposes of illustration only and that a number of changes may be made without departing from the scope of the invention. For example, other photosensitizers than those mentioned may be used, preferably photosensitizers which bind to nucleic acid and thereby keep it from replicating, and more preferably those which are not toxic and do not have toxic degradation products. In addition, equivalent structures to those described herein for constructing a flow-through system for decontamination of fluids using photosensitizers may be readily devised without undue experimentation by those skilled in the art following the teachings hereof. In addition, the level of plasma removal in blood or a blood component to achieve the desired level of inactivation of a particular microorganism or microorganisms may be readily determined using the methods described herein, or methods known to those of ordinary skill in the art without undue experimentation.

All references cited herein are incorporated by reference to the extent not inconsistent with the disclosure herein.

What is claimed is:

1. A method for treating a fluid to inactivate microorganisms which may be present therein, said fluid containing one or more components selected from the group consisting of protein, blood and blood constituents, said method comprising:

(a) adjusting the percentage of plasma in said fluid to a desired value;
(b) mixing an inactivation-effective, substantially non-toxic amount of an endogenous photosensitizer or endogenously-based derivative photosensitizer with said fluid;
(c) exposing said fluid to photoradiation of sufficient wavelength and energy to activate the photosensitizer, whereby said microorganisms are inactivated.

2. The method of claim 1, wherein said mixing step occurs after said adjusting step.

3. The method of claim 1, wherein said adjusting step occurs after said mixing step.

4. The method of claim 1, wherein said adjusting step and said mixing step occur simultaneously.

5. The method of claim 1, wherein said adjusting step comprises adding a sufficient volume of a diluting solution to the fluid so that the percentage of plasma is at a desired value.

6. The method of claim 5, wherein said diluting solution is saline.

7. The method of claim 5, wherein said diluting solution is a buffer.

8. The method of claim 5, wherein said diluting solution includes nutrients.

9. The method of claim 8, wherein said diluting solution includes phosphate.

10. The method of claim 5, wherein said diluting solution is a cell storage solution.

11. The method of claim 5, wherein said diluting solution is an anticoagulant.

12. The method of claim 5, wherein said diluting solution is a cryopreservative solution.

13. The method of claim 1, wherein said adjusting step comprises washing the fluid.

14. The method of claim 13 including a plurality of washing steps.

15. The method of claim 1 wherein said photosensitizer is a photo-activatable compound whose photolytic products (if any) are of low or no toxicity to humans or animals.

16. The method of claim 15 wherein said photosensitizer is 7,8-dimethyl-10-ribityl isoalloxazine.

17. The method of claim 1 wherein said microorganisms are selected from the group consisting of bacteria, bacteriophages, and intracellular and extracellular viruses.

18. The method of claim 1 wherein said microorganisms are bacteria.

19. The method of claim 1 wherein said microorganisms are selected from the group consisting of HIV viruses, hepatitis viruses, sindbis virus, cytomegalovirus, vesicular stomatitis virus, herpes simplex viruses, vaccinia virus, human T-lymphotropic retroviruses, HTLV-III, lymphadenopahy virus LAV/IDAV, parvovirus, transfusion-transmitted (TT) virus, Epstein-Barr virus, bacteriophages ΦX174, Φ6, λ, R17, $T_4$, $T_2$, *P. aeruginosa, S. aureus, S. epidermidis, L. monocytogenes, E. coli K. pneumoniae* and *S. marcescens*.

20. The method of claim 1 wherein said photoradiation is light in the visible spectrum.

21. The method of claim 1, wherein said photoradiation is light in the ultraviolet spectrum.

22. The method of claim 1, wherein said photoradiation is light in both the visible and ultraviolet spectra.

23. The method of claim 22, wherein about half the light is in the visible spectrum and about half the light is in the ultraviolet spectrum.

24. The method of claim 22, wherein about one third of the light is in the visible spectrum and about two thirds of the light is in the ultraviolet spectrum.

25. The method of claim 22, wherein about two thirds of the light is in the visible spectrum and about one third of the light is in the ultraviolet spectrum.

26. The method of claim 1, wherein said photoradiation is of sufficient wavelength to activate 7,8-dimethyl-10-ribityl isoalloxazine in the fluid.

27. The method of claim 1, wherein the percentage of plasma in said fluid is adjusted to be within about 0 to about 50 percent of the total volume of said fluid when said fluid contains platelets, red blood cells, or a combination of both.

28. The method of claim 1, wherein the percentage of plasma in said fluid is adjusted to be within about 0 to about 20 percent of the total volume of said fluid when said fluid contains platelets, red blood cells, or a combination of both.

29. The method of claim 1, wherein the percentage of plasma in said fluid is adjusted to be within about 0 to about 10 percent of the total volume of said fluid when said fluid contains platelets, red blood cells, or a combination of both.

30. The method of claim 1, wherein the percentage of plasma in said fluid is adjusted to be within about 99 to about 80 percent of the total volume of said fluid.

31. The method of claim 1 wherein said photosensitizer is added to anticoagulant and said anticoagulant is added to said fluid.

32. A method of claim 1 wherein an enhancer is added to said fluid prior to exposing said fluid to photoradiation.

33. A method of claim 32 wherein said enhancer is selected from the group consisting of adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof.

34. The method of claim 1 wherein said exposing step comprises flowing the fluid containing said photosensitizer past a source of photoradiation at a rate and depth selected to ensure penetration of the photoradiation through the fluid and inactivation of the microorganisms.

35. The method of claim 1 wherein said fluid and photosensitizer are contained in a container transparent to said photoradiation.

36. The method of claim 35 further comprising agitating said container during said exposing step.

37. The method of claim 1 wherein said adding step further comprises placing said fluid in a container transparent to said photoradiation, adding said photosensitizer to said fluid in powder form, and agitating said container.

38. The method of claim 37, wherein said percentage of plasma is adjusted before placing said fluid in said container.

39. The method of claim 37, wherein said percentage of plasma is adjusted after placing said fluid in said container.

40. The method of claim 37, wherein said percentage of plasma is adjusted simultaneously with placing said fluid in said container.

41. The method of claim 37, further comprising adding nutrients in powder form to said container.

42. The method of claim 37 wherein said nutrients and photosensitizer are present in the container prior to addition of said fluid.

43. The method of claim 1 wherein said fluid comprises blood constituents.

44. The method of claim 1 wherein said fluid comprises whole blood.

45. The method of claim 1 wherein said fluid comprises a separated blood product.

46. The method of claim 1 wherein said fluid consists essentially of platelets.

47. The method of claim 1 wherein said fluid consists essentially of serum.

48. The method of claim 1 wherein said fluid consists essentially of plasma.

49. The method of claim 1 wherein said fluid consists essentially of red blood cells.

50. The method of claim 1 wherein said fluid comprises a therapeutic protein composition.

51. The method of claim 1 wherein said fluid contains a biologically-active protein selected from the group consisting of: factor VIII, Von Willebrand factor, factor IX, factor X, factor XI, Hageman factor, prothrombin, anti-thrombin III, fibronectin, plasminogen, plasma protein fraction, peritoneal dialysis solutions, immune serum globulin, modified immune globulin, albumin, plasma growth hormone, somatomedin, plasminogen streptokinase complex, ceruloplasmin, transferrin, haptoglobin, antitrypsin and prekallikrein.

52. The method of claim 1 wherein the activity of a biologically-active protein in said fluid is at a biologically-active level after said exposing step.

53. A blood product comprising inactivated microorganisms and endogenous photosensitizer or endogenously-based derivative photosensitizer and a lowered plasma content than occurs naturally, made by the method of claim 1.

54. A method for treating a fluid containing platelets to inactivate microorganisms which may be present therein, said method comprising:
(a) mixing an inactivation-effective, substantially non-toxic amount of an endogenous photosensitizer with a fluid which contains platelets and a plasma content of between about 0% to about 50% of the total volume of the fluid;
(b) exposing said fluid to photoradiation of sufficient wavelength and energy to activate the photosensitizer, whereby said microorganisms are inactivated.

55. The method of claim 54, wherein said fluid contains a plasma content between about 0 to about 25% of the total volume of said fluid.

56. The method of claim 54, wherein said fluid contains plasma at a volume of less than 25% of the total volume of said fluid.

57. The method of claim 54, wherein said method further comprises: adding sufficient additives to the fluid so that one or more proteins present in said fluid remains biologically active after said exposing step.

58. The method of claim 54, wherein said photosensitizer is 7,8-dimethyl-10-ribityl isoalloxazine.

59. The method of claim 54, wherein said photosensitizer is present at a concentration of between about 1 to about 200 micromolar.

60. The method of claim 54, wherein said photoradiation is between about 400 and about 500 nm.

61. The method of claim 54, wherein said photoradiation is between about 100 and about 500 J/cm$^2$.

62. The method of claim 54, wherein said photoradiation is between about 100 and about 200 J/cm$^2$.

63. A method for treating a fluid containing red blood cells to inactivate microorganisms which may be present therein, said method comprising:
(a) adding an inactivation-effective, substantially non-toxic amount of an endogenous photosensitizer to a fluid which contains red blood cells and a plasma content of between about 0% to about 50% of the total volume of said fluid;
(b) exposing said fluid to photoradiation of sufficient wavelength and energy to activate the photosensitizer, whereby said microorganisms are inactivated.

64. The method of claim 63, wherein said plasma content in said fluid is less than about 10% of the total volume of said fluid.

65. The method of claim 63, wherein said plasma content is less than about 5% of the total volume of said fluid.

66. The method of claim 63, wherein said photosensitizer is 7,8-dimethyl-10-ribityl isoalloxazine.

67. The method of claim 63, wherein said photosensitizer is present at a concentration of between about 1 to about 200 micromolar.

68. The method of claim 63, wherein said photosensitizer is present at a concentration of between about 50 to about 150 micromolar.

69. The method of claim 63, wherein said photoradiation is between about 420 and about 500 nm.

70. The method of claim 63, wherein said photoradiation is between about 100 and about 500 J/cm$^2$.

71. The method of claim 63, wherein said photoradiation is between about 50 and about 200 J/cm$^2$.

72. A method for treating a fluid containing plasma to inactivate microorganisms which may be present therein, said method comprising:
(a) adding an inactivation-effective, substantially non-toxic amount of an endogenous photosensitizer to a fluid having a plasma content of between about 60% to about 100% of the total volume of said fluid;
(b) exposing said fluid to photoradiation of sufficient wavelength and energy to activate the photosensitizer, whereby said microorganisms are inactivated.

73. The method of claim 72, wherein said fluid contains about 90% or less plasma by volume.

74. The method of claim 72, wherein said photosensitizer is 7,8-dimethyl-10-ribityl isoalloxazine.

75. The method of claim 72, wherein said photosensitizer is present at a concentration of between about 5 to about 15 micromolar.

76. The method of claim 72, wherein said photoradiation is between about 300 and about 500 nm.

77. The method of claim 72, wherein said photoradiation is between about 100 and about 500 J/cm$^2$.

78. The method of claim 72, wherein said photoradiation is between about 300 and about 500 J/cm$^2$.

79. An apparatus for inactivating microorganisms which may be present in a fluid, said fluid having a portion of the plasma removed, with an endogenous or endogenously-based derivative photosensitizer, comprising:
(a) a source of light that emits light of a suitable wavelength and intensity to activate the endogenous or endogenously-based derivative photosensitizer;
(b) means for maintaining the fluid and an effective amount of an endogenous or endogenously-based derivative photosensitizer in the light path for a sufficient time to achieve the desired level of inactivation.

80. The apparatus of claim 79, wherein said means for maintaining the fluid and an effective amount of an endogenous or endogenously-based derivative photosensitizer in the light path comprises a support surface substantially parallel to said source of light.

81. The apparatus of claim 79, wherein said light source comprises one or more light emitting diodes.

82. The apparatus of claim 81, wherein said light emitting diodes emit light in the visible range of the spectrum.

83. The apparatus of claim 79, wherein said fluid comprises blood or blood components.

84. The apparatus of claim 79, wherein said photosensitizer is 7,8-dimethyl-10-ribityl isoalloxazine.

85. A system for treating a fluid to inactivate microorganisms which may be present therein with an endogenous or endogenously based photosensitizer comprising:
(a) a container comprising said fluid having a reduced level of plasma, at least an effective amount of an endogenous photosensitizer or endogenously-based derivative photosensitizer, and optionally one or more additives, said container having a surface sufficiently photopermeable to allow exposure of the fluid therein to an amount of photoradiation sufficient to activate the photosensitizer;
(b) at least one photoradiation source in light communication with said container, said source capable of generating a suitable wavelength and intensity to activate the endogenous photosensitizer or endogenously-based derivative photosensitizer whereby microorganisms present are inactivated.

86. The system of claim 85, wherein said photosensitizer is 7,8-dimethyl-10-ribityl isoalloxazine.

87. The system of claim 85 wherein said photoradiation source provides light in the visible spectrum.

88. The system of claim 85, wherein said photoradiation source provides light in the ultraviolet spectrum.

89. The system of claim 85, wherein said photoradiation source provides light in both the visible and ultraviolet spectrum.

90. The system of claim 85 also comprising a photoradiation enhancer.

91. The system of claim 90 wherein said photoradiation enhancer comprises a reflective surface.

92. The system of claim 85 comprising a light guide for conducting photoradiation from said photoradiation source to said photopermeable container.

93. The system of claim 85 also comprising a temperature monitor.

94. The system of claim 85 also comprising one or more temperature controllers.

95. The system of claim 94 wherein said temperature controller is a fan directed so as to cool the light source and/or the fluid.

96. The system of claim 85 also comprising means for flowing said fluid into and out of said container.

97. The system of claim 85 also comprising means for agitating said fluid.

98. A system for inactivation of microorganisms in a fluid containing such microorganisms comprising:
(a) means for adjusting the plasma content of said fluid;
(b) means for mixing an effective amount of an endogenous photosensitizer or endogenously-based derivative photosensitizer with said fluid in fluid communication with said means for adjusting the plasma content of said fluid;
(c) a photopermeable container for said fluid in fluid communication with said means for adding photosensitizer and said means for adjusting the plasma content having a depth and length selected to allow exposure of the fluid of step (b) therein to an amount of photoradiation sufficient to activate the photosensitizer at a selected flow rate;
(d) means for producing said selected flow rate of said fluid through said container; and (e) at least one photoradiation source in light communication with said container, said source capable of providing sufficient photoradiation to the fluid in said container of a type and amount selected to activate the photosensitizer.

99. A system for treating a fluid to inactivate microorganisms which may be present therein comprising:
   (a) means for adjusting the percentage of plasma in said fluid;
   (b) means for adding an effective amount of endogenous or endogenously-based photosensitizer to said fluid;
   (c) a photopermeable container for said fluid of depth which allows exposure of the fluid to an amount of photoradiation sufficient to activate the photosensitizer;
   (d) means for agitating said container;
   (e) at least one photoradiation source for providing sufficient photoradiation to the fluid in said container of a type and amount selected to activate the photosensitizer.

100. The system of claim 99 wherein said photopermeable container is a transparent plastic bag.

101. The system of claim 100 wherein said photopermeable container is a transparent rigid plastic container.

102. The system of claim 99 wherein said means for agitating said container comprises a shaker table.

103. The system of claim 99 wherein said photopermeable container contains said photosensitizer prior to addition of said fluid.

104. The system of claim 99 wherein said means for adjusting the level of plasma in said fluid comprises a suitable amount of a solution contained in said container.

105. A method for collecting a fluid with reduced levels of microorganisms that may be present therein, said fluid containing one or more members of the group consisting of: blood and blood components, comprising:
   (a) placing said fluid in a photopermeable container;
   (b) adding an endogenous or endogenously-based derivative photoactive material to said container;
   (c) adjusting the level of plasma in said fluid to a desired level;
   (d) exposing said fluid to radiation of a sufficient wavelength and intensity to activate said photoactive material, whereby microorganisms are inactivated.

106. The method of claim 105 wherein said photoactive material is present in said container prior to placing said fluid therein.

107. An apparatus for collecting a fluid with reduced levels of microorganisms that may be present therein, said fluid containing one or more members of the group consisting of: blood and blood components, comprising:
   (a) a photopermeable container containing an endogenous or endogenously-based derivative photoactive material and a suitable volume of a solution for adjusting the level of plasma in the fluid to a desired level;
   (b) a light source in light communication with said container that emits light of a suitable wavelength and intensity to inactivate microorganisms which may be present in said fluid.

108. A method for treating a fluid to inactivate microorganisms which may be present therein, said fluid containing one or more components selected from the group consisting of protein, blood and blood constituents, said method comprising:
   (a) removing a desired amount of the bilirubin present in the fluid;
   (b) adding an inactivation-effective, substantially non-toxic amount of an endogenous photosensitizer or endogenously-based derivative photosensitizer to said fluid;
   (c) exposing said fluid to photoradiation of sufficient wavelength and energy to activate the photosensitizer, whereby said microorganisms are inactivated.

* * * * *